United States Patent
Desogere et al.

(10) Patent No.: US 10,471,162 B2
(45) Date of Patent: Nov. 12, 2019

(54) COLLAGEN TARGETED IMAGING PROBES

(71) Applicant: The General Hospital Corporation, Boston, MA (US)

(72) Inventors: Pauline Desogere, Cambridge, MA (US); Peter Caravan, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/320,112

(22) PCT Filed: Jun. 22, 2015

(86) PCT No.: PCT/US2015/037017
§ 371 (c)(1),
(2) Date: Dec. 19, 2016

(87) PCT Pub. No.: WO2015/196208
PCT Pub. Date: Dec. 23, 2015

(65) Prior Publication Data
US 2017/0360967 A1    Dec. 21, 2017

Related U.S. Application Data

(60) Provisional application No. 62/014,744, filed on Jun. 20, 2014.

(51) Int. Cl.
*A61K 51/08*    (2006.01)
*A61K 38/00*    (2006.01)
*C07K 14/00*    (2006.01)

(52) U.S. Cl.
CPC .............. *A61K 51/08* (2013.01); *A61K 38/00* (2013.01); *C07K 14/00* (2013.01)

(58) Field of Classification Search
CPC ...... A61K 51/00; A61K 51/08; A61K 51/088; A61K 38/00; C07K 14/00
USPC ........ 424/1.11, 1.65, 1.69, 9.1, 9.2, 9.3, 9.4, 424/9.5, 9.6; 514/1, 1.1, 21.4; 530/300, 530/326
See application file for complete search history.

(56) References Cited

U.S. PATENT DOCUMENTS

| | | | |
|---|---|---|---|
| 4,899,755 A | 2/1990 | Lauffer et al. | |
| 6,984,373 B2 | 1/2006 | Wescott et al. | |
| 6,991,775 B2 | 1/2006 | Koerner et al. | |
| 8,034,898 B2 * | 10/2011 | Caravan .................. | A61B 5/055 530/317 |
| 9,386,938 B2 * | 7/2016 | Caravan .................. | A61B 5/055 |
| 2005/0261472 A1 | 11/2005 | Wescott et al. | |
| 2013/0172270 A1 | 4/2013 | Lam et al. | |

FOREIGN PATENT DOCUMENTS

| | | |
|---|---|---|
| WO | WO 86/06605 | 11/1986 |
| WO | WO 91/03200 | 3/1991 |
| WO | WO 95/28179 | 10/1995 |
| WO | WO 96/23526 | 8/1996 |
| WO | WO 97/36619 | 10/1997 |
| WO | WO 98/18496 | 5/1998 |
| WO | WO 1998/046612 | 10/1998 |
| WO | WO 1999/017809 | 4/1999 |
| WO | WO 2012/095347 | 7/2012 |

OTHER PUBLICATIONS

Caravan et al, Angew. Chem. Int. Ed, vol. 46, pp. 8171-8173. (Year: 2007).*
Cai et al., "Evaluation of Copper-64 Labeled AmBaSar Conjugated Cyclic RGD Peptide for Improved MicroPET Imaging of Integrin αvβ3 Expression," Bioconjugate Chem, Jul. 2010, 21: 1417-1424.
Caravan et. al. "Collagen-targeted MRI contrast agent for molecular imaging of fibrosis." Angew Chem Int Ed Engl., 2007, 46(43):8171-3.
Helm et al. "Postinfarction myocardial scarring in mice: molecular magnetic resonance (MR) imaging with use of a collagentargeting contrast agent." Radiology, Jun. 2008, 247(3):788-96.
Hutson et al., "Liquid chromatographic determination of hydroxyproline in tissue samples," Journal of Chromatography B, 2003, 791(1): 427-430.
International Preliminary Report on Patentability in International Application No. PCT/US2015/037017, dated Dec. 20, 2016, 9 pages.
Kolodziej et al., "Peptide optimization and conjugation strategies in the development of molecularly targeted magnetic resonance imaging contrast agents," Methods Mo/ Biol., 2014, 1088:185-211.
Lattuada et al., "The synthesis and application of polyamino polycarboxylic bifunctional chelating agents," Chem. Soc. Rev., 2011, 40: 3019-3049.
Levy et al., "Development of a Multigram Asymmetric Synthesis of 2-(R)-2-(4,7,10-Tris tert-Butylcarboxymethyl-1,4,7,10-tetraazacyclododec-1-yl)-pentanedioic Acid, 1-tert-Butyl Ester, (R)-tert-Bu4-DOTAGA," Org. Process Res. Dev., 2009, 13: 535-542.
Loening and Gambhir, "AMIDE: a free software tool for multimodality medical image analysis," Mol. Imaging, 2003, 2: 131-137.
Merrifield, "Solid-Phase peptide Synthesis. I. The Synthesis of a Tetrapeptide," J. Am. Chem. Soc, 1963, 85:2149-2145.
Notni et al., "TRAP, a Powerful and Versatile Framework for Gallium-68 Radiopharmaceuticals," Chem. Eur. J., Dec. 2011, 17: 14718-14722.
Schibli and Schubiger, "Current use and future potential of organometallic radiopharmaceuticals," Eur J Nucl Med Mol Imaging, Nov. 2002, 29:1529-1542.

(Continued)

*Primary Examiner* — D. L. Jones
(74) *Attorney, Agent, or Firm* — Fish & Richardson P.C.

(57) ABSTRACT

Disclosed herein are collagen-targeted imaging agents for positron emission tomography and related imaging methods using the collagen-targeted imaging agents. The collagen-targeted imaging agent is a cyclic polypeptide comprising a cyclic main body, wherein the cyclic main body comprises at least one S—S bond; at least two branches, wherein each of the at least two branches comprises at least three amino acids; and a linker, wherein the linker is capable of linking an imaging reporter.

31 Claims, 16 Drawing Sheets

(56) References Cited

OTHER PUBLICATIONS

Shea et al., "Prolonged Exposure to Sphingosine 1—Phosphate Receptor-1 Agonists Exacerbates Vascular Leak, Fibrosis, and Mortality after Lung Injury," Am J Respir Cell Mo/ Biol, 2010, 43: 662-673.
Simecek et al., "A Monoreactive Bifunctional Triazacyclononane Phosphinate Chelator with High Selectivity for Gallium-68," ChemMedChem, Aug. 2012, 7: 1375-1378.
Tircso et al., "(S)-5-(p-Nitrobenzyl)-PCTA, a Promising Bifunctional Ligand with Advantageous Metal Ion Complexation Kinetics," Bioconjugate Chem., Feb. 2009, 20: 565-575.
Wadas et al., "Coordinating Radiometals of Copper, Gallium, Indium, Yttrium, and Zirconium for PET and SPECT Imaging of Disease," Chem. Rev., 2010, 110: 2858-2902.
Zeglis and Lewis, A practical guide to the construction of radiometallated bioconjugates for positron emission tomography, Dalton Trans., Jun. 2011, 40: 6168-6195.
Zhang et al., "Effect of Peptide-Chelate Architecture on Metabolic Stability of Peptide-based MRI Imaging reporters", New Journal of Chemistry, 2010, 34, 611-616.
International Search Report and Written Opinion dated Dec. 31, 2015 in international application No. PCT/US2015/37017, 12 pgs.
Caravan et al. "A lysine walk to high relaxivity collagen-targeted MRI contrast agents", Chem. Commun. 2009. p. 430-432, entire document, especially: p. 430, col. 1, para 1; p. 431, Figure 2; p. 431, Table 1; see also supplementary material attached separately, p. S10, Figure S2; p. S11, Figure S3.
Ramogida et al. "Tumour targeting with radiometals for diagnosis and therapy", Chem. Commun. 2013. vol. 49, pp. 4720-4739, entire document, especially: 4722, col. 2, para 4; p. 4724, col. 2, para 3; p. 4724, col. 1, para 4; p. 4725, col. 2, para 2; p. 4726, Table 5; p. 4729, Table 6.

\* cited by examiner

COLLAGEN TARGETED IMAGING PROBES

CROSS-REFERENCES TO RELATED APPLICATIONS

This application is a § 371 National Stage Application of PCT/US2015/037017, filed Jun. 22, 2015, which claims priority from U.S. Patent Application No. 62/014,744, filed Jun. 20, 2014. The entire contents of the foregoing are hereby incorporated by reference.

STATEMENT REGARDING FEDERALLY SPONSORED RESEARCH

This invention was made with government support under grant number NIH HL116315 awarded by National Institutes of Health. The government has certain rights in the invention.

BACKGROUND OF THE INVENTION

1. Field of the Invention

The invention relates to collagen targeted imaging agents for positron emission tomography.

2. Description of the Related Art

There is a major unmet medical need to noninvasively quantify fibrosis. Fibrosis quantification would enable early diagnosis of many chronic diseases and provide a means to monitor response to therapy, thus speeding evaluation of novel treatments. Noninvasive identification and staging of fibrosis would impact tens of millions of Americans with some form of chronic liver (e.g., hepatitis C), lung (e.g., idiopathic pulmonary fibrosis), or renal disease and hundreds of millions worldwide.

Fibrosis is a ubiquitous reactive response to tissue injury. Scar tissue as a result of wound healing is a positive example of fibrosis. However in chronic tissue injury, ongoing cycles of injury and repair lead to accumulation of scar tissue and disruption of normal tissue architecture and function, which ultimately can result in organ failure. The cellular and molecular biology of fibrosis is similar whether it occurs in kidney, liver, lung or elsewhere and whether its cause is viral, chemical, physical or inflammatory. Fibrosis results from the excessive activity of fibroblasts and involves upregulation of a number of extracellular matrix proteins, chiefly type I collagen. Many therapeutic interventions can reverse fibrosis if detected early; however, current radiological techniques only detect later stage disease where tissue damage may be irreversible.

The gold standard in assessing fibrosis is biopsy. However, depending on the organ of interest this can be challenging. For example, significant complications following liver biopsy, defined as requiring hospital admission or prolonged hospital stay, occur in 1 to 5% of patients and mortality has been reported between 0.01 and 0.1%. Similar rates arise with renal biopsy, and the risk of complications is much higher in lung biopsies. In addition, biopsy can suffer from sampling error, inter-observer variability, and does not sample differences in fibrosis across the organ. Of note, even for advanced stages of liver fibrosis such as cirrhosis, error rates in diagnosis of 33% have been reported. Repeated biopsies to evaluate disease progression or response to treatment are unattractive due to patient compliance and the increased risk of complications.

There is a clear and unmet medical need for safe, noninvasive means to diagnose and stage fibrotic diseases and to monitor response to treatment. Fibrosis, regardless of its cause or location, is characterized by excess deposition of collagens, primarily type I collagen, and other extracellular matrix proteins in the parenchyma. Indeed, histological proof of fibrosis is predicated on collagen staining. Type I collagen is an attractive target because of its presence in all forms of fibrosis and because its concentration increases as fibrosis progresses. Collagen is extracellular and readily accessible to the probe (cf. intracellular targets). Unlike certain cell surface receptors, there is no temporal aspect to collagen expression in fibrosis; there is turnover, but collagen levels are high and increase with increasing fibrosis.

Collagens are a class of extracellular matrix proteins that represent 30% of total body protein and shape the structure of tendons, bones, and connective tissues. Abnormal or excessive accumulation of collagen in organs such as the liver, lungs, kidneys, or breasts, and vasculature can lead to fibrosis of such organs (e.g., myocardial fibrosis, heart failure, nonalcoholic steatohepatitis of the liver (also known as NASH), cirrhosis of the liver, primary biliary cirrhosis), lesions in the vasculature or breasts, collagen-induced arthritis, Muscular dystrophy, scleroderma, Dupuytren's disease, rheumatoid arthritis, and other collagen vascular diseases. It would be useful to have diagnostic agents that could assist in the treatment or diagnosis of such disorders.

Compounds and pharmaceutical compositions for collagen imaging have been previously disclosed in U.S. Pat. No. 8,034,898 and various publications, including Kolodziej et al., "Peptide optimization and conjugation strategies in the development of molecularly targeted magnetic resonance imaging contrast agents." *Methods Mol Biol.* 2014; 1088: 185-211; Helm et al. "Postinfarction myocardial scarring in mice: molecular magnetic resonance (MR) imaging with use of a collagen-targeting contrast agent." *Radiology.* 2008 June; 247(3):788-96; and Caravan et. al. "Collagen-targeted MRI contrast agent for molecular imaging of fibrosis." *Angew Chem Int Ed Engl.* 2007; 46(43):8171-3".

However, MRI contrast agents require a high mass dose in order to be detected by MRI, typically grams per subject. On the other hand, nuclear imaging techniques have very high detection sensitivity and the mass dose per subject is typically less than 1 milligram. The lower dose used in nuclear imaging should result in imaging probes that are much safer. Thus, improved collagen-targeting compounds that can be used with positron emission tomography (PET) or other gamma ray imaging techniques are needed.

SUMMARY OF THE INVENTION

The disclosure is based on collagen-targeting probes for positron emission tomography (PET) imaging.

The disclosure is based on imaging probes that can include a collagen-binding peptide, wherein the peptide can function both as a targeting group and a point of attachment for one or more imaging reporters at one or more of the internal amino acids and N-termini, either directly or via an optional intervening linker.

Peptides described herein exhibit an affinity for collagen, and can be used to evaluate physiologic functions, manifestations, or disorders where collagens are present in either normal or atypically high concentrations. In some embodiments, the peptide has affinity for collagen type I.

In one aspect, the collagen-targeting peptide may comprise: (a) a cyclic main body, wherein the cyclic main body comprises at least one S—S bond; (b) at least two branches, wherein each of the at least two branches comprises at least three amino acids; and (c) a functional group selected capable of attaching an imaging reporter. The functional group can be selected from the group consisting of amine, aldehyde, ketone, carboxylic acid, azide, alkyne. In a preferred embodiment, the functional group is an amine.

In one embodiment, the collagen-targeting probes comprise a radionuclide to make the probe detectable by PET. The radionuclide can be selected from the group consisting of copper-64 (Cu-64, $^{64}$Cu), gallium-68 (Ga-68, $^{68}$Ga) or fluorine-18 (F-18, $^{18}$F).

In some embodiments, the radionuclide is a radioactive metal that can be complexed to a metal chelating group. The metal chelating group can include a cyclic or acyclic organic chelating agent. In some cases, the cyclic or acyclic organic chelating agent can be selected from the group consisting of DTPA (diethylenetriaminepentaacetic acid), DOTA (1,4,7,10-tetraazacyclododecane-1,4,7,10-tetraacetic acid), DOTAGA (1,4,7,10-tetraazacyclododececane, 1-(glutaric acid)-4,7,10-triacetic acid), NOTA (1,4,7-triazacyclononane-triacetic acid), and NODAGA (1,4,7-triazacyclononane, 1-glutaric acid-4,7-acetic acid).

In one embodiment, the imaging reporter can be a radionuclide selected from the group consisting of $^{11}$C, $^{13}$N, $^{15}$O and $^{18}$F. In one specific case, the radionuclide can be directly attached to the peptide by a covalent bond via an intervening linker or prosthetic group. In some embodiments, a peptide and one or more imaging reporters are covalently bound through a linker. A linker can be on the C-terminus, the N-terminus, or both, of a peptide. Additionally, a linker can be bound to the side chain of a peptide. If a peptide is bound to multiple linkers, each linker can be different. A linker can be covalently linked to a side chain of an amino acid. In some embodiments, an amino acid side chain can serve as the linker.

The linker can be a small cyclic or acyclic organic molecule that can include at least one functional group selected from the group consisting of ketones, amides, alkyne, azide, amine, and isothiocyanate. In a specific embodiment, the linker can be linked to a metal complex formed by a chelating agent labeled with a metal such as Al (III). The chelating agent can be selected from the group consisting of NOTA and NODAGA.

In some embodiments, the collagen-targeting probes comprise more than one chelating agent.

In one embodiment, the cyclic polypeptide comprises two branches. Preferably, one of the two branches comprises three amino acids. In one embodiment, the three amino acids are leucine (L), tyrosine (Y) and glycine (G). In one embodiment, the three amino acids are phenylalanine (F), tyrosine (Y) and glycine (G). In one embodiment, one of the two branches comprises leucine (L), 2-Nal (2-naphthylalanine) and glycine (G). In one embodiment, one of the two branches comprises leucine (L), tyrosine (Y) and BIP (L-4,4'-biphenylalanine).

In one embodiment, one of the least two branches comprises at least four amino acids. In one embodiment, the at least four amino acids comprise histidine (H), tryptophan (W), glutamine (Q) and glycine (G). In one embodiment, the branch having at least four amino acids further comprises at least one chelating group.

In one embodiment, one of the least two branches comprises at least five amino acids. In one embodiment, the at least five amino acids comprise histidine (H), tryptophan (W), lysine (K), glycine (G and glycine (G).

In one embodiment, the branch having at least five amino acids further comprises at least one chelating group. In one embodiment, the chelating group is NODAGA. In one embodiment, the chelating group is NOTA.

In one aspect, the present invention discloses a compound of formula (I)

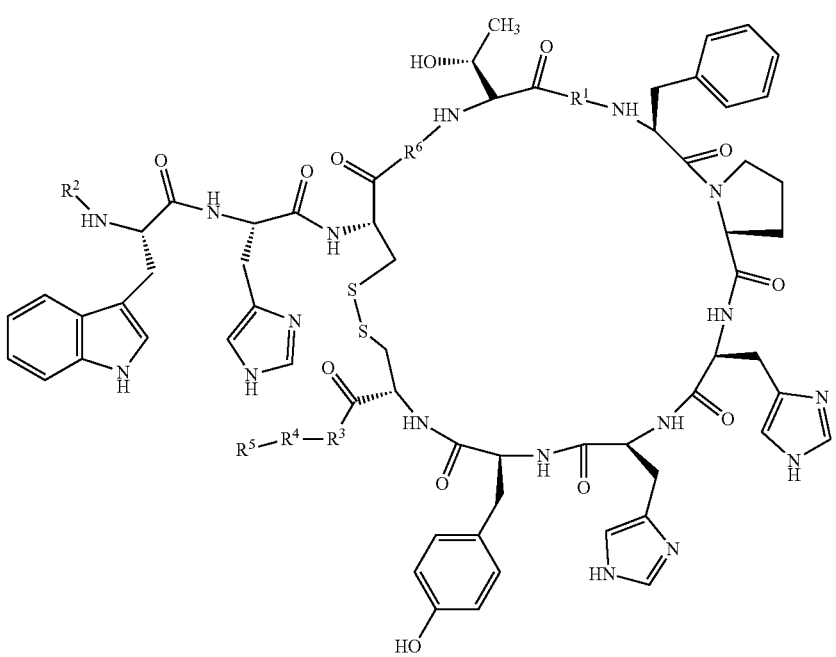

wherein $R^1$ comprises at least one amino acid;
wherein $R^2$ comprises at least one amino acid;
wherein $R^3$ comprises at least one amino acid;
wherein $R^4$ comprises at least one amino acid;
wherein $R^5$ comprises at least one amino acid;
wherein $R^6$ comprises at least one amino acid and
wherein the cyclic polypeptide further comprises a metal chelating group (e.g., NODAGA or NOTA) capable of binding an imaging reporter, the metal chelating group being covalently linked directly to a cyclic body or a branch of the cyclic polypeptide, or the metal chelating group being linked to the body or a branch of the cyclic polypeptide via a linker.

In one embodiment, $R^1$ is selected from the group consisting of tyrosine (Y), aspartic acid (D), arginine (R), leucine (L), glutamic acid (E), and lysine (K)-(NODAGA). In one embodiment, $R^1$ is selected from the group consisting of tyrosine (Y), aspartic acid (D), arginine (R), leucine (L), glutamic acid (E), and lysine (K) (NOTA-amide).

In one embodiment, $R^2$ is selected from the group consisting of NODAGA-glycine (G)-tryptophan (W) and NODAGA-glycine (G)-lysine (K)[glycine (G)-NODAGA]. In one embodiment, $R^2$ is selected from the group consisting of (NOTA-amide)-glycine (G)-tryptophan (W) and (NOTA-amide)-glycine (G)-lysine (K)[glycine (G)-(NOTA-amide].

In one embodiment, $R^3$ is selected from the group consisting of leucine (L) and phenylalanine (F).

In one embodiment, $R^4$ is selected from the group consisting of tyrosine (Y) and 2-Nal (2-naphthylalanine).

In one embodiment, $R^5$ is selected from the group consisting of glycine (G) and BIP (L-4,4'-biphenylalanine).

In one embodiment, $R^6$ is selected from the group consisting of threonine (T) and tyrosine (Y).

In one aspect, the present invention provides a method of distinguishing fibrotic from non-fibrotic pathologies in mammals in vivo by using a collagen-binding PET probe. In some cases, the method includes: (a) administering to the mammal an imaging agent comprising a collagen-targeting peptide having at least one chelator and a radioactive element, (b) acquiring an image of the newly formed and still disorganized collagen using PET imaging, (c) acquiring an anatomical image of the mammal using computed tomography (CT), and (d) overlaying the images of step (b) and (c) to localize the image of collagen within the anatomical image of the mammal. A fibrotic pathology exhibits higher uptake as compared to a non-fibrotic pathology.

In the above methods, the pathology can be selected from liver fibrosis, kidney fibrosis, myocardial infarction, and lung fibrosis.

These and other features, aspects, and advantages of the present invention will become better understood upon consideration of the following detailed description, drawings, and appended claims.

DETAILED DESCRIPTION OF THE INVENTION

Figure 1:
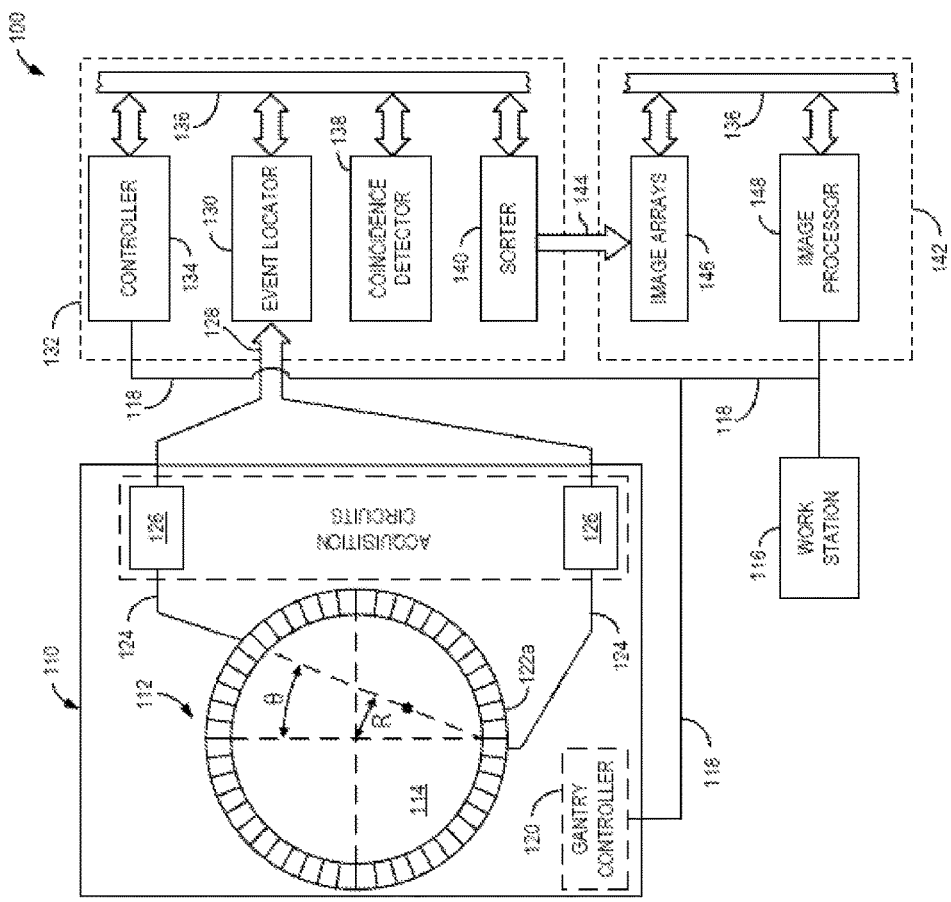
FIG. 1 is a schematic view of an emission tomography system suitable for use with the present invention.

Commonly used chemical abbreviations that are not explicitly defined in this disclosure may be found in The American Chemical Society Style Guide, Second Edition; American Chemical Society, Washington, D.C. (1997), "2001 Guidelines for Authors" *J. Org. Chem.* 66(1), 24A (2001), "A Short Guide to Abbreviations and Their Use in Peptide Science" *J. Peptide. Sci.* 5, 465-471 (1999).

As used herein, the term "peptide" may comprise a chain of amino acids that is 16 or 17 amino acids in length. All peptide sequences herein are written from the N to C terminus. Additionally, the peptides described herein contain two or more cysteine residues that can form one or more disulfide bonds under non-reducing conditions. Formation of a disulfide bond can result in the formation of a cyclic peptide.

The term "amino acid," as used herein, refers to naturally occurring and non-natural amino acids, as well as amino acid analogs and amino acid mimetics that function in a manner similar to the naturally occurring amino acids. Naturally encoded amino acids are the 20 common amino acids (and their corresponding one-letter symbols) [alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), and valine (V)] and pyrrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In one preferred embodiment, the amino acids in the present invention are all naturally occurring amino acids.

The term "non-naturally occurring amino acid," refers to an amino acid that is not one of the 20 common amino acids or pyrrolysine or selenocysteine; other terms that may be used synonymously with the term "non-natural amino acid" is "non-naturally encoded amino acid", "unnatural amino acid", "non-naturally-occurring amino acid", and variously hyphenated and non-hyphenated versions thereof. The term "non-natural amino acid" includes, but is not limited to, amino acids that occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine.

The term "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins, wherein the amino acid residues are linked by covalent peptide bonds. In one embodiment, polypeptides of the present invention are made of all naturally occurring amino acids. Applicants envision that polypeptides of the present invention may also include non-natural amino acids.

The term "cyclic polypeptide" as used herein, refers to a type of conformationally restrained polypeptide that, as its name suggests, contains a cyclic polymer of amino acids. The term "cyclic polypeptide" is also used to describe a polypeptide (including a cyclic peptide) that is circularized via a peptide bond between the N and C terminal amino acids of a linear polypeptide. In one embodiment, cyclic polypeptides of the present invention are made of all naturally occurring amino acids. Applicants envision that cyclic polypeptides of the present invention may also include non-natural amino acids.

As used herein, the terms "administer" when used to describe the dosage of a compound, means a single dose or multiple doses of the compound.

The term "subject" as used herein, refers to an animal, in some embodiments a mammal, and in other embodiments a human, who is the object of treatment, observation or experiment. The term "individual" as used herein refers to any body, living or dead, of any species.

The term "imaging reporter" as used herein, refers to a group that makes the probe visible in a particular imaging modality. For instance, an imaging reporter can be a radionuclide to make the probe detectable by PET or SPECT, or it can be a complex of Gd(III) to make the probe detectable by MRI. The term as used herein is synonymous with "labeling agent". The term "imaging reporter" comprises both forms. In one example embodiment, the imaging reporter is a positron emitter.

The term "chelating group" or "chelating agent" as used herein, refers to one or more molecules, or chemical radicals, or moieties, which provide a favorable environment for linking a cation. Dissociation of the cation from the environment is hindered due to kinetic or/and thermodynamic stability of linking to the chelating group.

The term "positron" as used herein refers to the antiparticle or the antimatter counterpart of the electron. The positron has an electric charge of +1, a spin of ½, and the same mass as an electron. When a low-energy positron collides with a low-energy electron, annihilation occurs, resulting in the production of two or more gamma ray photons. Positrons may be generated by positron emission radioactive decay (through weak interactions), or by pair production from a sufficiently energetic photon.

The term "positron emitter" as used herein, refers to any molecule or substance that is capable of emitting positron(s).

The term "positron emission tomography" or "PET" as used herein, refers to a nuclear medicine imaging technique which produces a three-dimensional image or picture of functional processes in the body. The PET scanner detects pairs of gamma rays emitted indirectly by a positron-emitting radionuclide (tracer), which is introduced into the body on a molecule. Images of tracer concentration in three-dimensional space within the body are then reconstructed by computer analysis.

The term "positron emission tomography imaging" or "PET imaging" as used herein, refers to the use of PET to capture images, particularly of a living body. It is to be understood that the term includes both dynamic and static images received as a result of the technique.

The term "magnetic resonance imaging" or "MRI" as used herein, refers to the use of magnetic resonance to capture images, particularly of a living body. It is to be understood that the term includes both dynamic and static images received as a result of the technique.

The term "single-photon emission computed tomography" or "SPECT" as used herein, refers to a nuclear medicine tomographic imaging technique using a gamma-emitting radioisotope and a gamma camera for detecting gamma radiation emitted by the radioisotope.

The term "computed tomography" or "CT" as used herein, refers to a medical imaging method employing tomography where digital geometry processing is used to generate a three-dimensional image of the internals of an object from a large series of two-dimensional X-ray images taken around a single axis of rotation. The term as used herein is non-exclusive, and includes CT-based methods and combination methods, such as PET/CT.

The term "target compartment" as used herein, refers to any location in an individual. Examples of target compartments may be an organ, e.g., the heart, lung, liver, vessels, bone marrow, and others; a tissue (e.g. the cortex of the kidney), a compartment (e.g., the lumen of an artery). In one embodiment, a target compartment may be a lung.

The term "probe" or "imaging probe" as used herein, refers to a molecule suitable for use in positron-emission tomography, SPECT or any other imaging technique, which can be administered to a patient, for example, by injection, and which accumulates in a tissue of interest. The location and local concentration of the probe can then be deduced using PET scanning and tomography, SPECT or another type of imaging technique. A "PET probe" is suitable for use in PET.

The term "radionuclide" or "radioactive nuclide" as used herein, refers to a nuclide that is radioactive. Also referred to as a radioisotope or radioactive isotope, it is an isotope with an unstable nucleus, characterized by excess energy available to be imparted either to a newly created radiation particle within the nucleus or via internal conversion. During this process, the radionuclide is said to undergo radioactive decay, resulting in the emission of gamma ray(s) and/or subatomic particles such as alpha or beta particles. These emissions constitute ionizing radiation. Many radionuclides occur naturally, and others are produced artificially, for example in nuclear reactors and cyclotrons.

The term "radioactive tracer," or "radioactive label," as used herein, refers to a chemical compound in which one or more atoms have been replaced by a radioisotope or where a radioisotope is incorporated to the molecule via a linker or linker and chelating group (e.g., by formation of a metal complex) so by virtue of its radioactive decay it can be used to explore the mechanism of chemical reactions by tracing the path that the radioisotope follows from reactants to products. Radiolabeling is thus the radioactive form of isotopic labeling.

The term "collagen-targeted" or "collagen-binding" as used herein, refers to an imaging probe that can specifically bind collagen, therefore specifically suitable for imaging collagen.

The term "systemic delivery", as used herein, refers to any suitable administration methods which may deliver the compounds in the present invention systemically. In one embodiment, systemic delivery may be selected from the group consisting of oral, parenteral, intranasal, inhaler, sublingual, rectal, and transdermal administrations.

Any route of administration may be suitable for the present invention. In one embodiment, the compound of the present invention may be administered to the subject via intravenous injection. In another embodiment, the compounds of the present invention may be administered to the subject via any other suitable systemic deliveries, such as oral, parenteral, intranasal, sublingual, rectal, or transdermal administrations. In another embodiment, the compounds of the present invention may be administered to the subject via nasal systems or mouth through, e.g., inhalation. In another embodiment, the compounds of the present invention may be administered to the subject via intraperitoneal injection.

Referring to FIG. 1, an example PET system 100 that can be used in the method of present invention includes an imaging hardware system 110 that includes a detector ring assembly 112 about a central axis, or bore 114. An operator work station 116 including a commercially-available processor running a commercially-available operating system communicates through a communications link 118 with a gantry controller 120 to control operation of the imaging hardware system 110.

The detector ring assembly 112 is formed of a multitude of radiation detector units 122 that produce a signal responsive to detection of a photon on communications line 124 when an event occurs. A set of acquisition circuits 126 receive the signals and produce signals indicating the event coordinates (x, y) and the total energy associated with the photons that caused the event. These signals are sent through a cable 128 to an event locator circuit 130. Each acquisition circuit 126 also produces an event detection pulse that indicates the exact moment the interaction took place. Other systems utilize sophisticated digital electronics that can also obtain this information regarding the precise instant in which the event occurred from the same signals used to obtain energy and event coordinates.

The event locator circuits 130 in some implementations, form part of a data acquisition processing system 132 that periodically samples the signals produced by the acquisition circuits 126. The data acquisition processing system 132 includes a general controller 134 that controls communications on a backplane bus 136 and on the general communications network 118. The event locator circuits 130 assemble the information regarding each valid event into a set of numbers that indicate precisely when the event took place and the position in which the event was detected. This event data packet is conveyed to a coincidence detector 138 that is also part of the data acquisition processing system 132.

The coincidence detector 138 accepts the event data packets from the event locator circuit 130 and determines if any two of them are in coincidence. Coincidence is determined by a number of factors. First, the time markers in each event data packet must be within a predetermined time window, for example, 0.5 nanoseconds or even down to picoseconds. Second, the locations indicated by the two event data packets must lie on a straight line that passes through the field of view in the scanner bore 114. Events that cannot be paired are discarded from consideration by the coincidence detector 138, but coincident event pairs are located and recorded as a coincidence data packet. These coincidence data packets are provided to a sorter 140. The function of the sorter in many traditional PET imaging systems is to receive the coincidence data packets and generate memory addresses from the coincidence data packets for the efficient storage of the coincidence data. In that context, the set of all projection rays that point in the same direction (θ) and pass through the scanner's field of view (FOV) is a complete projection, or "view". The distance (R) between a particular projection ray and the center of the FOV locates that projection ray within the FOV. The sorter 140 counts all of the events that occur on a given projection ray (R, θ) during the scan by sorting out the coincidence data packets that indicate an event at the two detectors lying on this projection ray. The coincidence counts are organized, for example, as a set of two-dimensional arrays, one for each axial image plane, and each having as one of its dimensions the projection angle θ and the other dimension the distance R. This θ by R map of the measured events is call a histogram or, more commonly, a sinogram array. It is these sinograms that are processed to reconstruct images that indicate the number of events that took place at each image pixel location during the scan. The sorter 140 counts all events occurring along each projection ray (R, θ) and organizes them into an image data array.

The sorter 140 provides image datasets to an image processing/reconstruction system 142, for example, by way of a communications link 144 to be stored in an image array 146. The image arrays 146 hold the respective datasets for access by an image processor 148 that reconstructs images. The image processing/reconstruction system 142 may communicate with and/or be integrated with the work station 116 or other remote work stations.

In one aspect, the present invention discloses a cyclic polypeptide. In one embodiment, the cyclic polypeptide may be made of all naturally existing amino acids. In another embodiment, the cyclic polypeptide may also comprise non-naturally existing amino acids.

This disclosure provides peptide-targeted imaging probes that contain a nuclear imaging reporter. A nuclear imaging reporter is a group that can makes the probe visible in this particular PET or SPECT imaging. It can be a positron emitter to be detected by PET imaging or a photon emitter to be detected by SPECT imaging.

The peptide-targeted nuclear imaging probes can be used to image collagen. For example, a collagen-specific agent that contains a radioactive element can be prepared. After administering this radio-labeled collagen-binding agent, an image can be obtained using a nuclear imaging technique like PET or SPECT that detects the imaging agent directly. A second image can then be obtained to acquire a high resolution anatomical map using either MRI or CT. The images can be overlaid to localize the collagen-targeted image within the high resolution anatomical image.

An imaging agent, as provided herein, incorporates a collagen binding peptide to allow for specific imaging of collagen within a subject. Any peptide capable of binding collagen may be used. For example, the peptides disclosed in U.S. Pat. No. 8,034,898 may be used.

In one embodiment, this disclosure provides a cyclic polypeptide of formula (I):

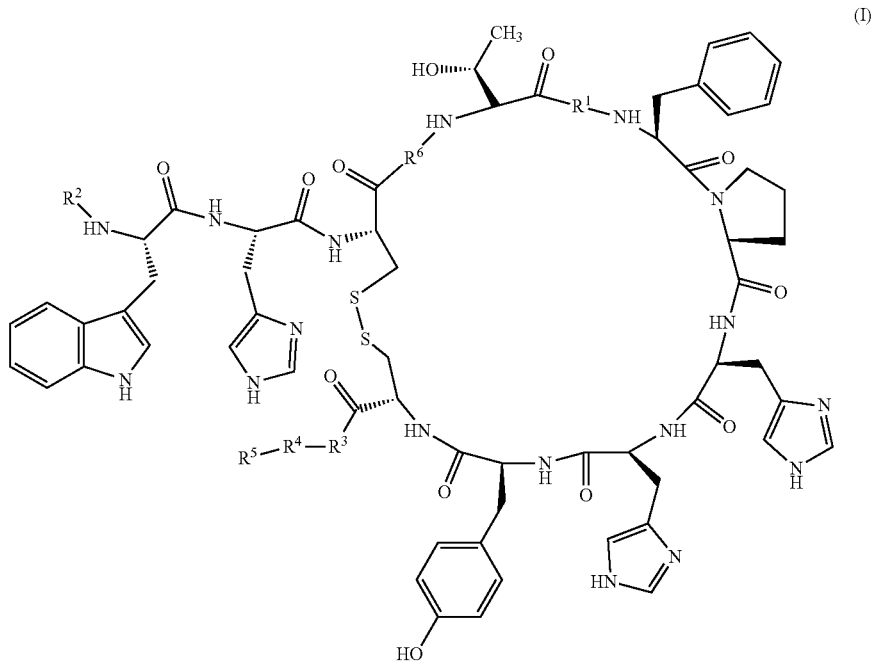

wherein R¹ comprises at least one amino acid;
wherein R² comprises at least one amino acid;
wherein R³ comprises at least one amino acid;
wherein R⁴ comprises at least one amino acid;
wherein R⁵ comprises at least one amino acid;
wherein R⁶ comprises at least one amino acid;
wherein the cyclic polypeptide further comprises a linker that is capable of linking an imaging reporter, and
wherein R¹ includes at least one amino acid selected from the group consisting of lysine (K), tyrosine (Y), glutamic acid (E), aspartic acid (D), arginine (R) and leucine (L).

In another embodiment, this disclosure provides a cyclic polypeptide of formula (I):

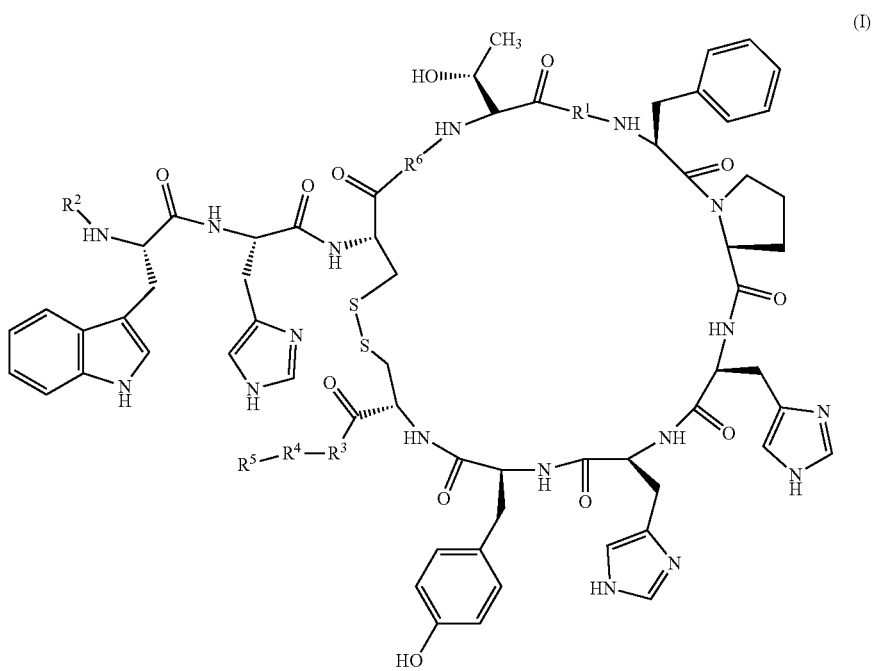

wherein:

R¹ is lysine (K)-NODAGA,

R² is NODAGA-glycine (G)-lysine (K)[glycine (G)-NODAGA],

R³ is leucine (L),

R⁴ is tyrosine (Y),

R⁵ is 4,4-biphenylalanine (BIP) and

R⁶ is threonine (T), and wherein the cyclic polypeptide comprises an imaging reporter. In one non-limiting example, the imaging reporter can be $^{68}$Ga.

In another embodiment, this disclosure provides a cyclic polypeptide of formula (I):

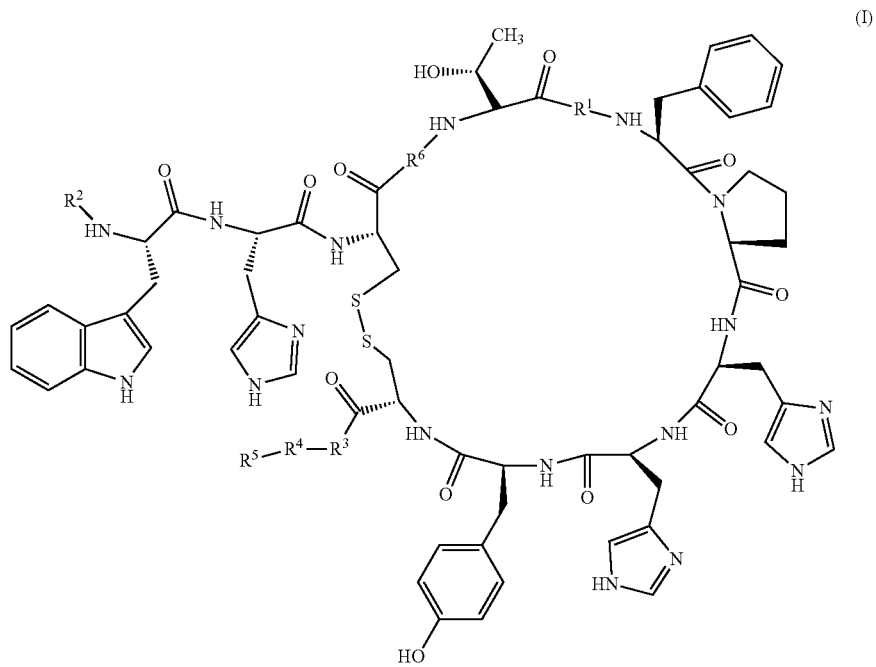
wherein:
R¹ is tyrosine (Y),
R² is NODAGA-glycine (G)-glutamine(Q),
R³ is leucine (L),
R⁴ is tyrosine (Y),
R⁵ is glycine (G),
R⁶ is threonine (T), and
wherein the cyclic polypeptide comprises an imaging reporter.
In another embodiment, this disclosure provides a cyclic polypeptide of formula (I):
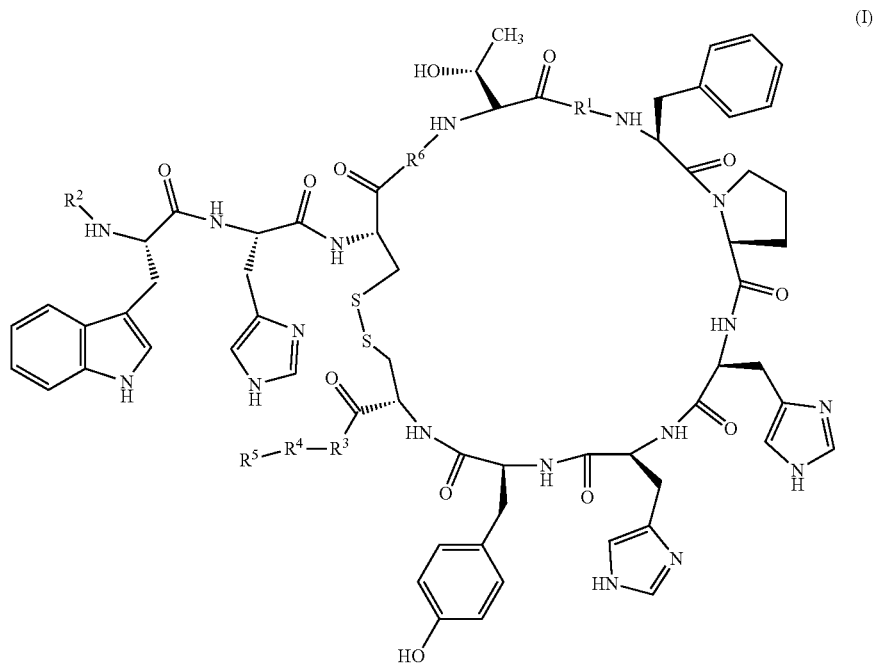

wherein:
R¹ is aspartic acid (D),
R² is NODAGA-glycine (G)-glutamine(Q),
R³ is leucine (L),
R⁴ is 2-naphthylalanine (2-Nal),
R⁵ is glycine (G),
R⁶ is threonine (T), and
wherein the cyclic polypeptide comprises an imaging reporter.

In another embodiment, this disclosure provides a cyclic polypeptide of formula (I):

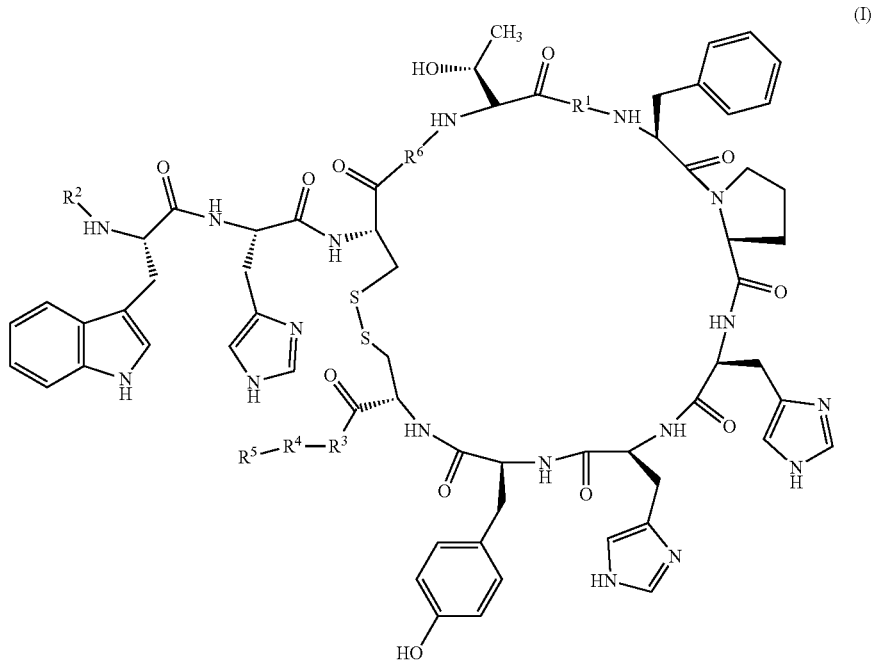

(I)

wherein:
R¹ is arginine (R),
R² is NODAGA-glycine (G)-glutamine(Q),
R³ is phenylalanine (F),
R⁴ is tyrosine (Y),
R⁵ is glycine (G) and
R⁶ is threonine (T), and
wherein the cyclic polypeptide comprises an imaging reporter.

In another embodiment, this disclosure provides a cyclic polypeptide of formula (I):

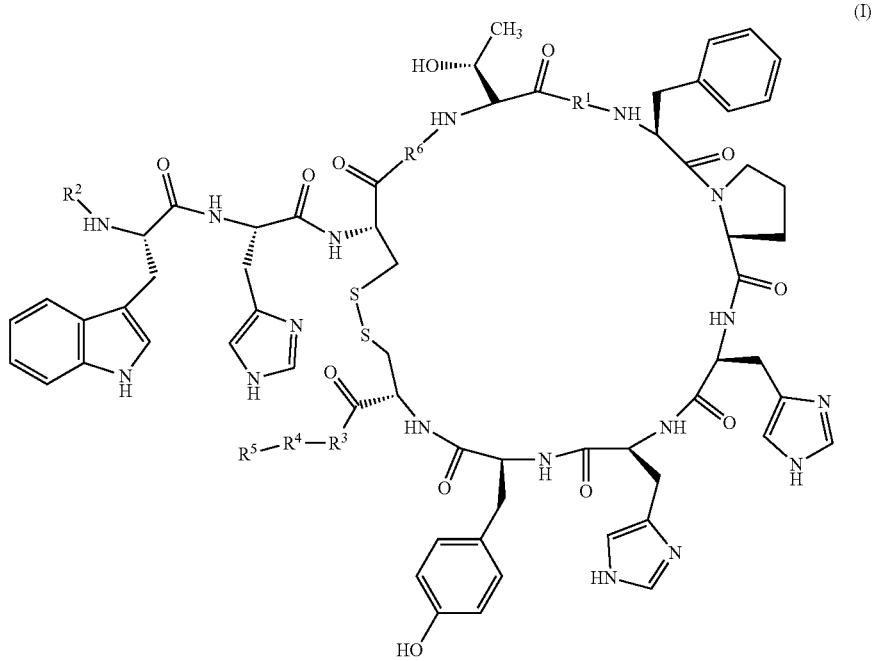

(I)

wherein:

R¹ is leucine (L),
R² is NODAGA-glycine (G)-glutamine(Q),
R³ is leucine (L),
R⁴ is tyrosine (Y),
R⁵ is glycine (G),
R⁶ is tyrosine (Y), and
wherein the cyclic polypeptide comprises an imaging reporter.

In another embodiment, this disclosure provides a cyclic polypeptide of formula (I):

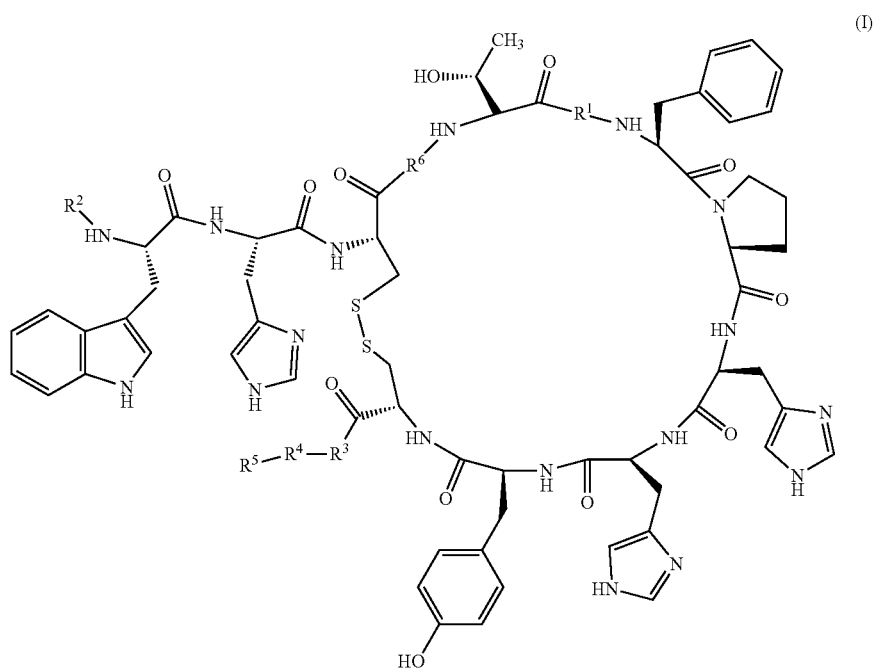

(I)

wherein:

R¹ is glutamic acid (E),
R² is NODAGA-glycine (G)-glutamine(Q),
R³ is leucine (L),
R⁴ is tyrosine (Y),
R⁵ is 4,4-biphenylalanine (BIP),
R⁶ is threonine (T), and
wherein the cyclic polypeptide comprises an imaging reporter.

In non-limiting examples of any of the above embodiments, the imaging reporter may be $^{64}$Cu.

In another embodiment, this disclosure provides a compound having the following structure:

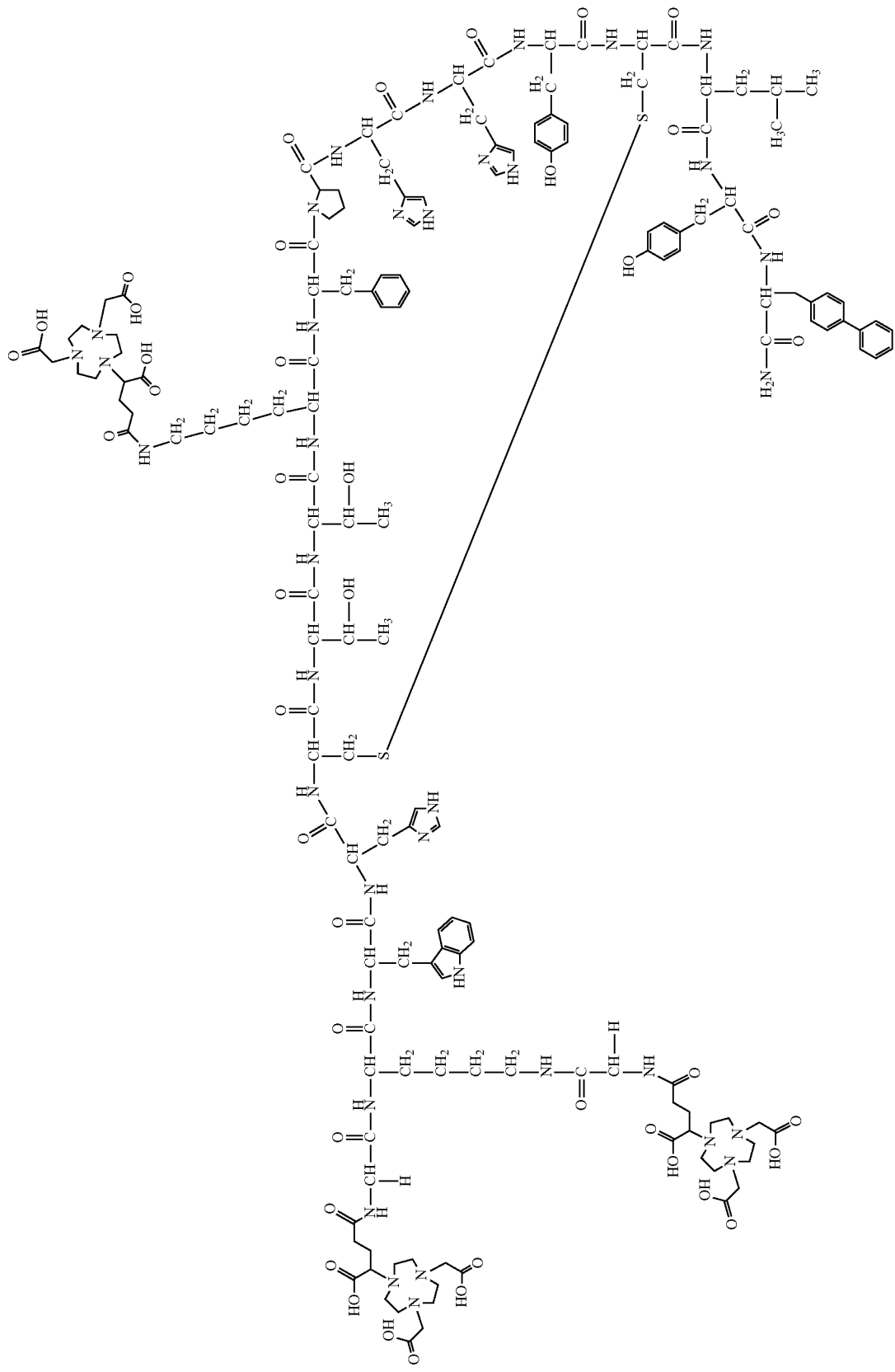

or a pharmaceutically acceptable salt thereof. The compound may be complexed to one or more positron emitting metal ion isotopes selected from the group consisting of: $^{44}$Sc, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{86}$Y, $^{89}$Zr, $^{94}$Tc. The compound may be complexed to one or more gamma-ray emitting metal ion isotopes selected from the group consisting of: $^{67}$Ga, $^{99m}$Tc, $^{111}$In, $^{201}$Tl. The compound may be complexed to one or more aluminum [18F]fluoride ions ($[Al^{18}F]^{2+}$). The compound may be complexed to one or more $^{64}$Cu ions. The compound may be complexed to one or more $^{68}$Ga ions.

In another embodiment, this disclosure provides a cyclic polypeptide comprising: (a) a cyclic main body, wherein the cyclic main body comprises at least one S—S bond; (b) at least two branches, wherein each of the at least two branches comprises at least three amino acids; and (c) a metal chelating group capable of binding an imaging reporter, the metal chelating group being covalently linked directly to the body or at least one of the branches, or the metal chelating group being linked to In another embodiment, this disclosure provides a cyclic polypeptide of formula (I):

of $^{11}$C, $^{13}$N, $^{15}$O, $^{18}$F, $^{34m}$Cl, $^{38}$K, $^{44}$Sc, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{110m}$In, $^{118}$Sb, $^{120}$I, $^{121}$I, $^{122}$I, and $^{124}$I. Preferably, the positron emitter is $^{67}$Ga, $^{99m}$Tc, $^{111}$In, $^{123}$I, $^{125}$I, $^{131}$I, $^{201}$Tl, or $^{64}$Cu. Most preferably, the positron emitter is $^{68}$Ga or $^{64}$Cu.

In any of the above embodiments, the imaging reporter may be a photon emitter selected from the group consisting of $^{67}$Ga, $^{99m}$Tc, $^{111}$In, $^{123}$I, $^{125}$I, $^{131}$I, $^{64}$Cu and In any of the above embodiments including a metal chelating group, the metal chelating group may include at least one group selected from the group consisting of methylene phosponic acid groups, methylene phospinic acid groups, methylene carbohydroxamine acid groups, carboxyethylidene groups, and carboxymethylene groups. In non-limiting example embodiments, the metal chelating group is 1,4,7-triazacyclononane, 1-glutaric acid-4,7-acetic acid (NODAGA) or 1,4,7-triazacyclononane-triacetic acid (NOTA).

When the metal chelating group is linked to the body or a branch of the cyclic polypeptide via a linker, the linker may attached to the cyclic main body. When the metal

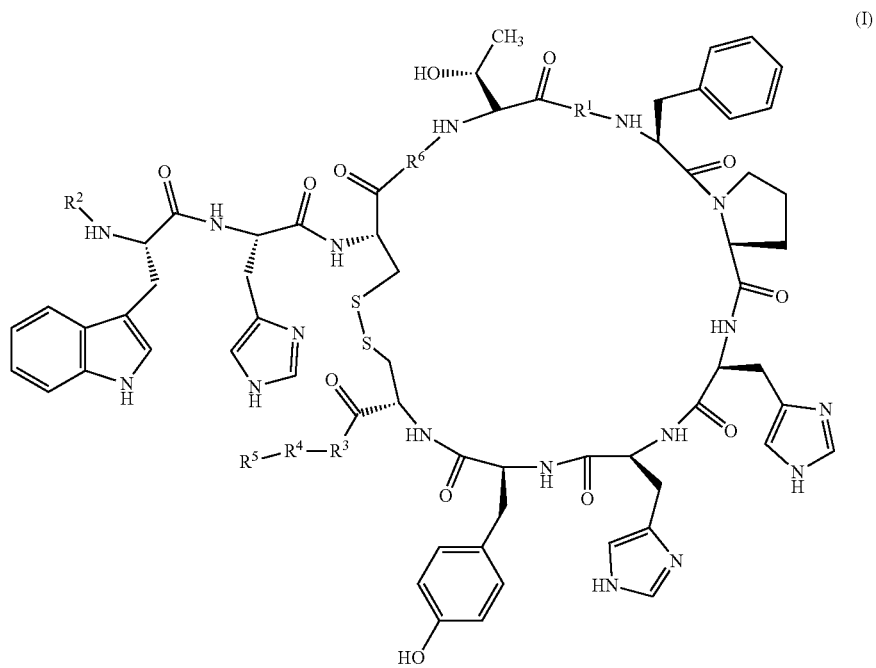

(I)

wherein R$^1$ comprises at least one amino acid;
wherein R$^2$ comprises at least one amino acid;
wherein R$^3$ comprises at least one amino acid;
wherein R$^4$ comprises at least one amino acid;
wherein R$^5$ comprises at least one amino acid;
wherein R$^6$ comprises at least one amino acid;
wherein the cyclic polypeptide further comprises a metal chelating group capable of binding an imaging reporter, the metal chelating group being covalently linked directly to a cyclic body or a branch of the cyclic polypeptide, or the metal chelating group being linked to the body or a branch of the cyclic polypeptide via a linker.

In any of the above embodiments, the cyclic main body of the cyclic polypeptide may comprise ten amino acids.

In any of the above embodiments, the imaging reporter may be a positron emitter selected from the group consisting chelating group is linked to the body or a branch of the cyclic polypeptide via a linker, the linker may attached to a lysine of the main body.

In any of the above embodiments, the cyclic polypeptide may comprise two branches. In one embodiment, one of the two branches comprises three amino acids, such as leucine (L), tyrosine (Y) and glycine (G) in any order, or leucine (L), 2-naphthylalanine (2-Nal) and glycine (G) in any order, or phenylalanine (F), tyrosine (Y) and glycine (G) in any order, or leucine (L), tyrosine (Y) and 4,4-biphenylalanine (BIP) in any order. In one embodiment, one of the least two branches comprises at least four amino acids, such as histidine (H), tryptophan (W), glutamine (Q) and glycine (G) in any order, or histidine (H)-tryptophan (W)-glutamine (Q)-glycine (G) in sequence. The branch having at least four amino acids may further comprise at least one chelating group. In one embodiment, one of the least two branches comprises at least five amino acids, such as histidine (H), tryptophan (W), lysine (K), glycine (G) and glycine (G) in any order, or histidine (H)-tryptophan (W)-lysine (K)-glycine (G)-glycine (G) in sequence. The branch having at least five amino acids may further comprise at least one chelating group, such as 1,4,7-triazacyclononane, 1-glutaric acid-4,7-acetic acid (NODAGA) or 1,4,7-triazacyclononane-triacetic acid (NOTA).

In some embodiments, $R^1$ may be selected from the group consisting of tyrosine (Y), aspartic acid (D), arginine (R), glutamic acid (E), leucine (L) and lysine (K)-(NODAGA). In some embodiments, $R^2$ may be selected from the group consisting of NODAGA-glycine (G)-glutamine(Q) and NODAGA-glycine (G)-lysine (K)[glycine (G)-NODAGA]. In some embodiments, $R^3$ may be selected from the group consisting of leucine (L) and phenylalanine (F). In some embodiments, $R^4$ may be selected from the group consisting of tyrosine (Y) and 2-naphthylalanine (2-Nal). In some embodiments, $R^5$ may be selected from the group consisting of glycine (G) and 4,4-biphenylalanine (BIP). In some embodiments, $R^6$ may be selected from the group consisting of threonine (T) and tyrosine (Y). The cyclic polypeptide may comprises a plurality of chelating groups, such as 1,4,7-triazacyclononane, 1-glutaric acid-4,7-acetic acid (NODAGA) or 1,4,7-triazacyclononane-triacetic acid (NOTA).

A collagen-binding peptide can have the general formula:

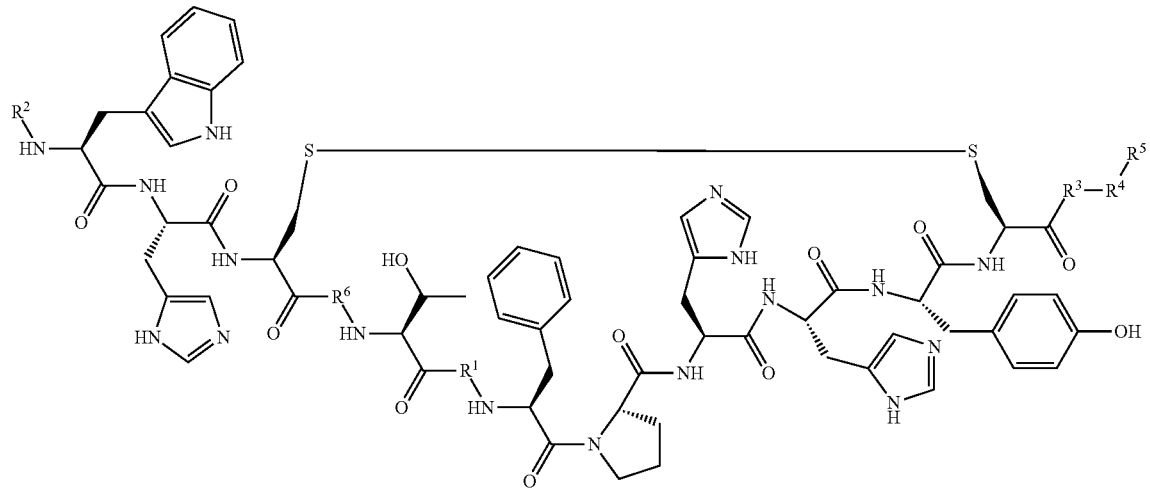

wherein $R^1$ comprises at least one amino acid;
wherein $R^2$ comprises at least two amino acids;
wherein $R^3$ comprises at least one amino acid;
wherein $R^4$ comprises at least one amino acid;
wherein $R^5$ comprises at least one amino acid;
wherein $R^6$ comprises at least one amino acid and
wherein the compound further comprises a linker that is capable of linking an imaging reporter.

In one embodiment, $R^1$ is selected from the group consisting of tyrosine (Y), aspartic acid (D), arginine (R), leucine (L), glutamic acid (E), and lysine (K). In one embodiment, $R^1$ is selected from the group consisting of tyrosine (Y), aspartic acid (D), arginine (R), leucine (L), glutamic acid (E), and lysine (K).

In one embodiment, $R^2$ is selected from the group consisting of -glycine (G)-tryptophan (W) and -glycine (G)-lysine (K)[glycine (G)].

In one embodiment, $R^3$ is selected from the group consisting of leucine (L) and phenylalanine (F).

In one embodiment, $R^4$ is selected from the group consisting of tyrosine (Y) and 2-Nal (2-naphthylalanine).

In one embodiment, $R^5$ is selected from the group consisting of glycine (G) and BIP (L-4,4'-biphenylalanine).

In one embodiment, $R^6$ is selected from the group consisting of threonine (T) and tyrosine (Y).

Peptides may be synthesized directly using conventional techniques, including solid-phase peptide synthesis, solution-phase synthesis, etc. See, for example, Stewart et al., Solid-Phase peptide Synthesis (1989), W.H. Freeman Co., San Francisco; Merrifield, J. Am. Chem. Soc, 1963 85:2149-2145; Bodanszky and Bodanszky, *The Practice of Peptide Synthesis* (1984), Springer-Verlag, New York. Peptides may also be prepared or purchased commercially. Automated peptide synthesis machines, such as manufactured by OEM Corporation, may also be used.

The collagen-binding peptide is preferably purified once it has been isolated or synthesized by either chemical or recombinant techniques. For purification purposes, there are many standard methods including reversed-phase high pressure (RPLC) using an alkylated silica column such as a $C_4$-, $C_5$-, $C_8$-, or $C_{18}$-silica. A gradient mobile phase of increasing organic content is usually used to achieve purification, for example, acetonitrile in an aqueous buffer, usually containing a small amount of trifluoroacetic acid. Ion-exchange chromatography can also be used to separate peptides based on their charge. The degree of purity of the collagen-binding peptide may be determined by various methods, including identification of a major large peak on HPLC. A peptide that produces a single peak that is at least 95% of the input material on an HPLC column is preferred. Even more preferable is a peptide that produces a single peak this is at least 97%, at least 98%, at least 99% or even 99.5% of the input material on an HPLC column.

To facilitate imaging of collagen, the collagen-binding peptide is detectably labeled with a radionuclide.

In one embodiment, the radionuclide can be selected from the group consisting of $^{11}C$, $^{13}N$, $^{15}O$ and $^{18}F$. In one specific case, the radionuclide can be directly attached to the peptide by a covalent bond via an intervening linker or prosthetic group. In some embodiments, a peptide and one or more imaging reporters are covalently bound through a linker, see below.

In some embodiments, the radionuclide is a radioactive metal that can be complexed to a chelator. The metal chelating group can include a cyclic or acyclic organic chelating agent. Suitable chelators are known in the art and include acids with methylene phosponic acid groups, methylene phospinic acid groups, methylene carbohydroxamine acid groups, carboxyethylidene groups or carboxymethylene groups. Examples of chelators include, but are not limited to diethylenetriaminepentaacetic acid (DTPA), 1,4,7,10-tetraazacyclododecane-1,4,7,10-tetraacetic acid (DOTA), 1,4,7,10-tetraazacyclododececane, 1-(glutaric acid)-4,7,10-triacetic acid (DOTAGA), ethylenediaminetetraacetic acid (EDTA), 1,4,7-triazacyclononane-triacetic acid (NOTA), 1,4,7-triazacyclononane, 1-glutaric acid-4,7-acetic acid (NODAGA) and 1,4,8,11-tetraazacyclotetradecane-1,4,8,11-tetraacetic acid (TETA). Additional chelating agents are dibenzo-DTPA, phenyl-DTPA, diphenyl-DTPA, benzyl-DTPA, and dibenzyl DTPA and derivatives thereof, the class of macrocyclic compounds which contains at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, amd benzo-NOTA, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid).

Additional chelating agents are 2,2'-(1,4,8,11-tetraazabicyclo[6.6.2]hexadecane-4,11-diyl)diacetic acid (CB-TE2A), SD-TE1A, 4-((8-amino-3,6,10,13,16,19-hexaazabicyclo[6.6.6]icosane-1-ylamino)methyl)benzoic acid (sar-CO2H) as described in *Chem. Rev.* 2010, 110, 2858-2902, *Bioconjugate Chem.* 2010, 21, 1417-1424, *Dalton Trans.*, 2011, 40, 6168, *Chem. Soc. Rev.*, 2011, 40, 3019-3049.

Additional chelating agents are 3,6,9,15-tetraazabicyclo[9.3.1]pentadeca-1,11,13-triene-3,6,9,-triacetic acid (PCTA), 3,6,9,15-tetraaza-bicyclo[9.3.1]-pentadeca-1(15),11,13-triene-4-S-(4-isothiocya-natobenzyl)-3,6,9-triacetic acid (p-SCN-Bn-PCTA), 1,4,7-Triazacyclononane Phosphinic Acid (TRAP), MA-NOTMP as described in *Bioconjugate Chem.* 2009, 20, 565-575, *Chem Med Chem*, 2012, 7, 1375-1378, *Chem. Eur. J.* 2011, 17, 14718-14722. Examples of other representatives chelators are described in WO 2012/095347 A1.

Additional chelating agents are EHIDA, methylenediphosphonate (MDP), MAG3, (1-hydroxyethylenediphosphonate) (EHDP), 1-hydroxy-4-aminobutylidene-1,1-diphosphonate (ABP), 6-hydrazinonicotinic acid (HYNIC) as described in Eur J Nucl Med Mol Imaging. 2002, 29(11): 1529-1542, J. Braz. Chem. Soc., 2006, 17(8).

Additional examples of representative chelators and chelating groups are described in WO 98/18496, WO 86/06605, WO 91/03200, WO 95/28179, WO 96/23526, WO 97/36619, PCT/US98/01473, PCT/US98/20182, U.S. Pat. Nos. 4,899,755 and 6,991,775, and U.S. Patent Application Publication No. 2005/0261472.

Additional examples of representative chelating groups are shown in the structures below:

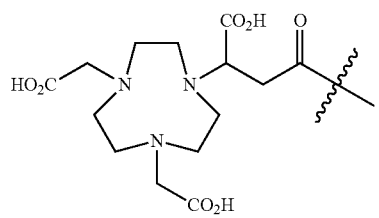

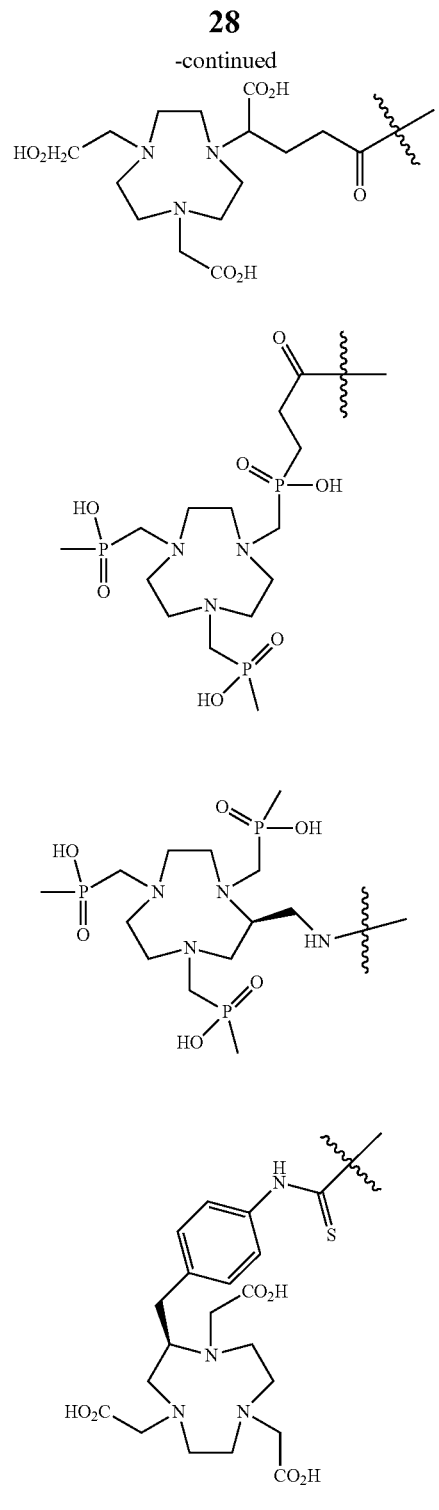

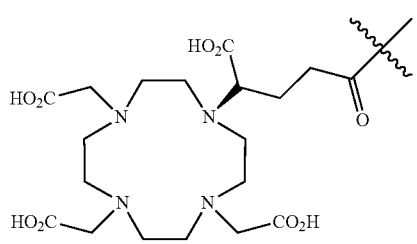

29
-continued
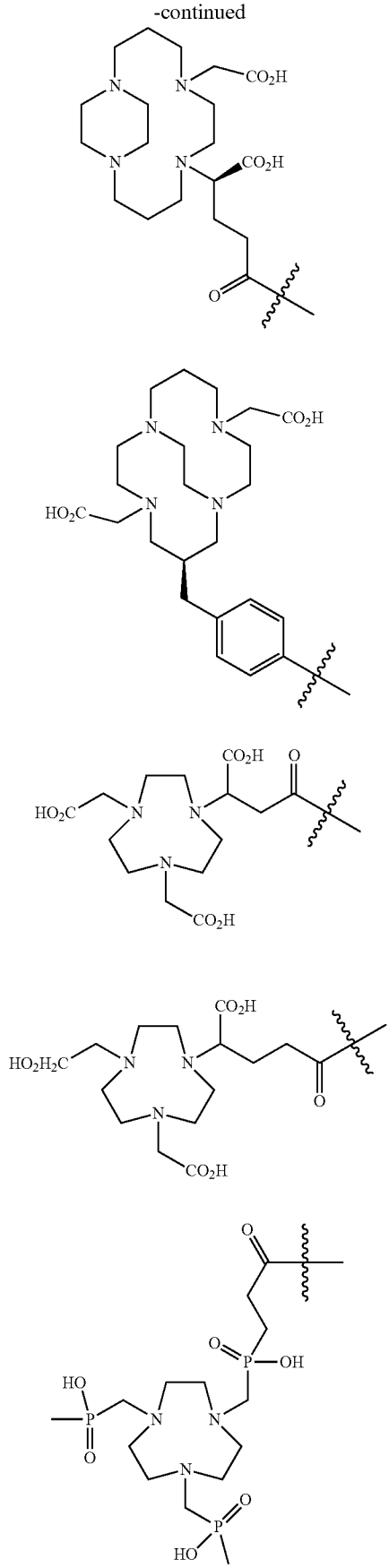
30
-continued
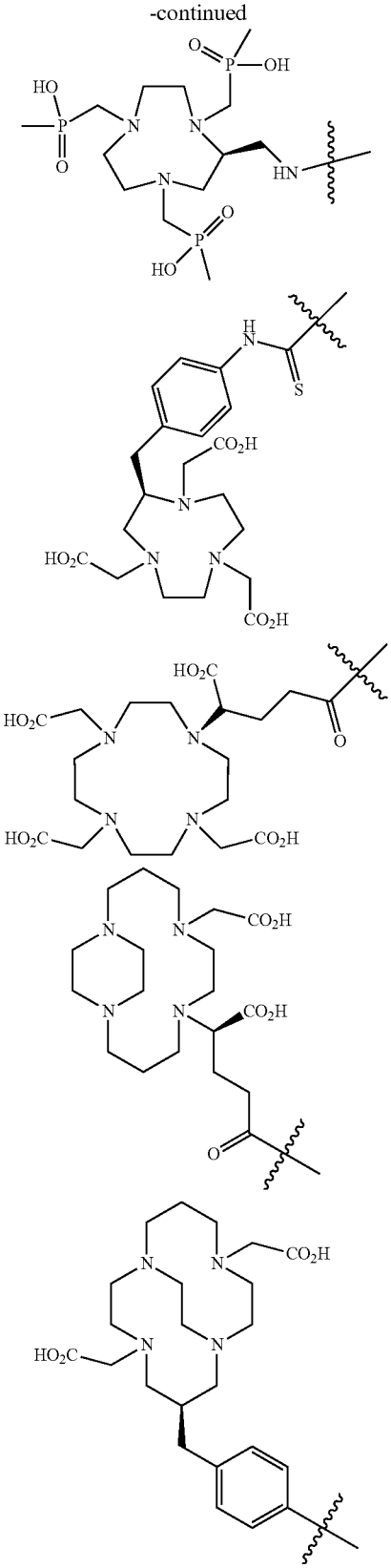
The chelator may be covalently linked directly to the collagen-binding moiety or linked to the collagen binding moiety via a linker, as described below.

The collagen-binding peptide may be conjugated with an imaging reporter agent comprising a positron emitter. The positron emitter can be selected from the group consisting of $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{110m}$In, $^{118}$Sb, $^{120}$I, $^{121}$I, $^{122}$I, and $^{124}$I. Preferably, the positron emitter is $^{18}$F, $^{68}$Ga, or $^{64}$Cu.

The imaging reporter may be a photon emitter. The photon emitter can be selected from the group consisting of $^{67}$Ga, $^{99m}$Tc, $^{111}$In, $^{123}$I, $^{125}$I, $^{131}$, and $^{201}$Tl.

In one specific embodiment, Applicants note that it is not obvious that any combination of collagen-targeted peptide and any imaging reporter would work. The number of chelators and their position on the peptide and the choice of radiolabel strongly affect in vivo efficacy in a manner not previously anticipated.

In some embodiments, the radioactive metal ion is $^{64}$Cu. Copper-64 ($t_{1/2}$=12.7 hours) is a useful radionuclide for PET applications. The longer half-life of $^{64}$Cu relative to other positron emitting radioisotopes like $^{11}$C (20 minutes) means no onsite cyclotron is required for production. Thus $^{64}$Cu can be shipped to users all over the country. An additional benefit to $^{64}$Cu is that the $^{64}$Cu label is introduced in the ultimate synthetic step via a highly thermodynamically favored chelation reaction which leads to higher specific activity and potentially no requirement for final HPLC purification. The long half-life and potential ease of preparation means that $^{64}$Cu-based molecular imaging probes have the potential to be more widely available to the nuclear medicine community, either in a kit form where the end user mixes the $^{64}$Cu with a probe precursor to formulate the probe or if the formulated probe is delivered by a centralized supplier.

In some embodiments, the radioactive metal ion is $^{68}$Ga. Gallium-68 ($t_{1/2}$=68 minutes) is a useful radionuclide for PET applications because it can be produced using an on-site Ge-68/Ga-68 generator.

The Examples show exemplary radiolabeling procedures according to one embodiment of the present invention. Applicants envision that any method appreciated by one skilled in the art may be used to radiolabel the compound of formula (I) with a positron emitter.

The imaging reporters described herein may be directly bound to the collagen binding peptide or conjugated through a linker moiety.

A linker can be on the C-terminus, the N-terminus, or both, of a peptide. Additionally, a linker can be bound to the side chain of a peptide. If a peptide is bound to multiple linkers, each linker can be different. A linker can be covalently linked to a side chain of an amino acid. In some embodiments, an amino acid side chain can serve as the linker.

A linker can be used to covalently attach one or more imaging reporters to the peptide terminus or to one internal amino acid. The linker may be branched or unbranched and may comprise multiple functional groups for imaging reporter attachment.

Linkers if present, typically are relatively small and rigid for the imaging agents described herein. For example, a linker can have a molecular weight less than about 350 (e.g., less than about 200).

The linker can be a small cyclic or acyclic organic molecule that can include at least one functional group selected from the group consisting of ketones, amides, alkyne, azide, amine, and isothiocyanate. In a specific embodiment, the linker can be linked to a metal complex formed by a chelating agent labeled with a metal such as Al (III). The chelating agent can be selected from the group consisting of NOTA and NODAGA.

In some embodiments, a linker is independently selected from the group consisting of
—NHCH(R)C(O)—, wherein R is any natural amino acid side chain;
—NH(CH$_2$)$_n$—C(O)—, wherein n is an integer from 1-6;
—NHCH$_2$CH$_2$OCH$_2$CH$_2$C(O)—;
—NHCH$_2$CH$_2$OCH$_2$CH$_2$OCH$_2$CH$_2$C(O)—;
—NH(CH$_2$)$_m$NH—, wherein m is an integer from 2-6;
NHCH$_2$OCH$_2$NH—;
NHCH$_2$CH$_2$OCH$_2$CH$_2$NH—; and
—NHCH$_2$CH$_2$OCH$_2$CH$_2$OCH$_2$CH$_2$NH—.

In one preferred embodiment, a collagen-binding nuclear imaging agent comprises a collagen-binding peptide bound optionally through one or more linkers to two or more imaging reporters.

For example, an unexpected finding in this work was that the compound of formula (I) with three NODAGA chelators were much more effective than those with one NODAGA chelator. Applicants envision that this is due to greater in vivo metabolic stability associated with those probes. The large hydrophilic chelators appear to block peptidase activity. Previous work with an unrelated peptide showed that it was necessary to block both the C- and N-termini with chelators to prevent metabolism. Here, Applicants found that it was not necessary to block the C-terminus.

The collagen-binding imaging agents described herein can be prepared using conventional synthetic methods known to those of skill in the art. See, for example, U.S. Pat. Nos. 6,984,373; 6,991,775; and U.S. Patent Application Publication No. 2005/0261472, as the well as the examples detailed below. The specific parameters included in the examples are intended to illustrate and are not presented to in any way limit the disclosure.

In one aspect, the present invention discloses any of the compounds as discussed above as examples of tool compounds suitable for development as therapeutic leads such that the radiolabeled imaging agents can be used in the method of the invention with a PET system such as that shown in FIG. 1 to assess the tissue- and region-specific target engagement of the tool compound via blocked linking of the imaging agent.

The linker can include a chelating agent for chelating a positron emitter, such as $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{75}$Br, $^{76}$Br, $^{82}$Rb, $^{86}$Y, $^{89}$Zr, $^{90}$Nb, $^{94m}$Tc, $^{110m}$In, $^{118}$Sb, $^{120}$I, $^{121}$I, $^{122}$I, and $^{124}$I. Preferably, the positron emitter is $^{68}$Ga, $^{64}$Cu, $^{11}$C or $^{18}$F. More preferably, the positron emitter is $^{18}$F, $^{68}$Ga, or $^{64}$Cu. In one preferred embodiment, the positron emitter is $^{68}$Ga or $^{64}$Cu.

In one preferred embodiment, any of the compounds as discussed above or the compound of formula (I) is targeted to collagen in the subject. Administration to the patient of a detectable amount of a pharmaceutical composition including the compound of formula (I) or any of the compound as discussed above for in vivo detection of collagen may be accomplished intravenously, intraarterially, intrathecally, intramuscularly, intradermally, subcutaneously, or intracavitary. Dosage can vary from 0.001 μg/kg to 10 μg/kg. In the method of the invention, sufficient time is allowed after administration such that the compound of formula (I) or any of the compounds as discussed above can bind collagen in the subject. A "detectable amount" means that the amount of the detectable compound that is administered is sufficient to enable detection of the compound in the subject by a medical imaging technique.

It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

In one aspect, the present invention discloses a method for in vivo imaging a subject by using any of the compounds as discussed above or any of the compounds of formula (I) as probes.

In one embodiment, the imaging technology may be positron emission tomography imaging, positron emission tomography with computed tomography imaging, or positron emission tomography with magnetic resonance imaging.

In one preferred embodiment, the imaging technology may be positron emission tomography imaging or positron emission tomography with computed tomography imaging.

In one embodiment of the present imaging method, the imaging probes may specifically target certain structural substances in the subject. In one preferred embodiment, the structural substances in the subject may be collagen.

As used herein, the term "collagen" refers to the main structural protein of the various connective tissues in animals. As the main component of connective tissue, it is the most abundant protein in mammals, making up from 25% to 35% of the whole-body protein content. Collagen, in the form of elongated fibrils, is mostly found in fibrous tissues such as tendons, ligaments and skin. It is also abundant in corneas, cartilage, bones, blood vessels, the gut, intervertebral discs and the dentin in teeth. In muscle tissue, it serves as a major component of the endomysium. Collagen constitutes one to two percent of muscle tissue, and accounts for 6% of the weight of strong, tendinous muscles. The fibroblast is the most common cell that creates collagen.

The five most common types of collagen include Type I: skin, tendon, vascular ligature, organs, bone (main component of the organic part of bone); Type II: cartilage (main collagenous component of cartilage); Type III: reticulate (main component of reticular fibers), commonly found alongside type I; Type IV: forms basal lamina, the epithelium-secreted layer of the basement membrane; and Type V: cell surfaces, hair and placenta.

In one embodiment, the present imaging method may be applicable to any tissues, organisms, or cells of a subject. In one non-limiting embodiment, the present imaging method may be applicable to for detection and staging of fibrosis in any part of a subject. In one preferred embodiment, the present imaging method may be applicable to for detection and staging of fibrosis in the lung, heart, liver, vessels, and bone marrow. We envision that we can image the newly formed-disorganized collagen in fibrotic tissues compared to really organized collagen that is naturally present in organs.

In one embodiment, the present invention discloses a method for in vivo imaging of a subject. The method comprises the steps of (a) administering to the subject any of the compounds as discussed above or any of the compounds of formula (I); (b) waiting a time sufficient to allow the compound to accumulate at a tissue site to be imaged; and (c) imaging the tissue with a non-invasive imaging technique.

After administration of the compound, one may wait a sufficient time (e.g., 30 minutes, 1 hour, 2 hours, 4 hours, 8 hours) so that the compound to accumulate at a tissue site to be imaged. In one embodiment, the tissue site to be imaged may include lung, heart, liver, vessels, bone marrow, etc.

In one embodiment, the tissues may be imaged with a non-invasive imaging technique.

In one embodiment, the non-invasive imaging technique may be selected from positron emission tomography imaging, positron emission tomography with computed tomography imaging, or positron emission tomography with magnetic resonance imaging.

In one example practice, one obtains two images or more, e.g., (i) one PET image, and (ii) one CT or MR image. The PET image showing the distribution of the tracer is then fused with the anatomical image provided by the MR or CT image, and in this way, the PET signal is localized to specific anatomical regions.

The Examples show the imaging results of collagen binding probes (CBP) in a mouse model of pulmonary fibrosis. Specifically, Applicants found that the CBP probes had significantly higher uptake in fibrotic lung than in normal lung after systemic administration of the probe, while distribution in other organs was similar.

In another specific embodiment, Applicants found that CBP7 among the Cu-64 labeled probes had greater uptake in fibrotic lung and a greater difference in uptake between fibrotic and normal lung than the other probes from ex-vivo analysis and PET imaging analysis.

In one embodiment, Applicants hypothesize that the difference in performance may be traced to in vivo stability of the probes. For example, the probe with greater in vivo stability may have better imaging performance than others.

In one aspect, the present invention discloses a method of imaging a subject by emission tomography. The method comprises the steps of (a) administering any of the compounds as discussed above that emit a gamma ray to the subject; (b) using a plurality of detectors to detect gamma rays emitted from the subject and to communicate signals corresponding to the detected gamma rays; and (c) reconstructing from the signals a series of medical images of a region of interest of the subject.

In one embodiment, the present imaging method may comprise the step of acquiring an image of a human patient to whom a detectable amount of any compound as discussed above has been administered.

In one embodiment, the present imaging method may comprise the step of acquiring a lung image of the patient.

In one embodiment, the present imaging method may comprise the step of acquiring the image using positron emission tomography imaging, positron emission tomography with computed tomography imaging, or positron emission tomography with magnetic resonance imaging.

In one embodiment, the detectable amount of the compound is an amount of the compound that is sufficient to enable detection of accumulation of the compound in tissue by a medical imaging technique.

In one embodiment, the present imaging method may comprise the step of acquiring the image using positron emission tomography imaging.

In one aspect, the present invention discloses a method for evaluating pulmonary fibrosis in a subject. The method comprises the steps of (a) administering to the subject any of the compounds disclosed herein; (b) waiting a time sufficient to allow the compound to accumulate at a tissue site to be imaged; and (c) imaging the tissue with a non-invasive imaging technique.

In one embodiment of the present imaging method, the tissue site is in the lung.

In one embodiment of the present imaging method, the non-invasive imaging technique is selected from positron emission tomography imaging, positron emission tomography with computed tomography imaging, or positron emission tomography with magnetic resonance imaging.

In one embodiment, the non-invasive imaging technique is positron emission tomography imaging, In another aspect, this disclosure provides a method for in vivo imaging of a subject. The method includes the steps of: (a) administering to the subject the cyclic polypeptide of any of above embodiments; (b) waiting a time sufficient to allow the cyclic polypeptide to accumulate at a tissue site to be imaged; and (c) imaging tissues with a non-invasive imaging technique. The non-invasive imaging technique may be selected from positron emission tomography imaging, single-photon emission computed tomography imaging, computed tomography imaging, magnetic resonance imaging, and any combination thereof. The non-invasive imaging technique may be positron emission tomography imaging.

In another aspect, this disclosure provides a method of imaging a subject by emission tomography. The method includes the steps of: (a) administering the cyclic polypeptide of any of the above embodiments to the subject, wherein the cyclic polypeptide includes an imaging reporter that emits gamma rays; (b) using a plurality of detectors to detect gamma rays emitted from the subject and to communicate signals corresponding to the detected gamma rays; and (c) reconstructing from the signals a series of medical images of a region of interest of the subject.

In another aspect, this disclosure provides an imaging method comprising acquiring an image of a human patient to whom a detectable amount of the cyclic polypeptide of any of the above embodiments has been administered. The method may comprise acquiring a lung image of the patient using a non-invasive imaging technique selected from positron emission tomography imaging, single-photon emission computed tomography imaging, computed tomography imaging, magnetic resonance imaging, and any combination thereof. The detectable amount of the cyclic polypeptide may be an amount of the cyclic polypeptide that is sufficient to enable detection of accumulation of the cyclic polypeptide in tissue by a medical imaging technique. The method may comprise acquiring the image using positron emission tomography imaging.

In another aspect, this disclosure provides a method for diagnosing a fibrotic disease in a subject. The method includes the steps of: (a) administering the cyclic polypeptide of any of the above embodiments to the subject; (b) waiting a time sufficient to allow the cyclic polypeptide to accumulate at a tissue site to be imaged; and (c) imaging tissues with a non-invasive imaging technique. The tissue site may be in the lung. The non-invasive imaging technique may be selected from positron emission tomography imaging, single-photon emission computed tomography imaging, computed tomography imaging, magnetic resonance imaging, and any combination thereof. The non-invasive imaging technique may be positron emission tomography imaging.

In another aspect, this disclosure provides a method for staging a fibrotic disease in a subject. The method includes the steps of: (a) administering the cyclic polypeptide of any of the above embodiments to the subject; (b) waiting a time sufficient to allow the cyclic polypeptide to accumulate at a tissue site to be imaged; (c) imaging tissues with a non-invasive imaging technique; and (d) comparing an amount of an imaging signal to a threshold. The tissue site may be in the lung. The non-invasive imaging technique may be selected from positron emission tomography imaging, single-photon emission computed tomography imaging, computed tomography imaging, magnetic resonance imaging, and any combination thereof. The non-invasive imaging technique may be positron emission tomography imaging.

In another aspect, this disclosure provides a method for monitoring treatment of a fibrotic disease in a subject. The method includes the steps of: (a) administering the cyclic polypeptide of any of the above embodiments to the subject; (b) waiting a time sufficient to allow the cyclic polypeptide to accumulate at a tissue site to be imaged; (c) imaging tissues with a non-invasive imaging technique to create a first image; (d) waiting a period of time after a therapeutic treatment; (e) repeating steps (a) and (b); (f) imaging tissues with the non-invasive imaging technique to create a second image; and (g) comparing the first image and the second image. The tissue site may be in the lung. The non-invasive imaging technique may be selected from positron emission tomography imaging, single-photon emission computed tomography imaging, computed tomography imaging, magnetic resonance imaging, and any combination thereof. The non-invasive imaging technique may be positron emission tomography imaging.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

The invention is further illustrated in the following Examples which are presented for purposes of illustration and not of limitation. The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Summary

In this disclosure, Applicants have proposed a set of compounds and have prepared a plurality of examples of collagen targeted peptides derivatized with a PET reporter (either F-18, Cu-64, or Ga-68). Applicants evaluated these collagen binding probes (CBP) in a mouse model of pulmonary fibrosis. In that model, mice were administered bleomycin or underwent a sham procedure. The bleomycin injured mice developed fibrosis in the lungs while the sham mice have normal lungs. Applicants found that CBP probes had significantly higher uptake in fibrotic lung than in normal lung after systemic administration of the probe, while distribution in other organs was similar. When Applicants used an isomeric compound that did not bind collagen, there was no difference in lung uptake between bleomycin injured and sham treated mice. Among the Cu-64 labeled probes, applicants found that CBP7 had greater uptake in fibrotic lung and a greater difference in uptake between fibrotic and normal lung than the other probes. This difference was traced to greater in vivo stability of this probe. In summary, Applicants have identified new example chemical entities and present in vivo data that these probes can be used for the noninvasive detection of pulmonary fibrosis.

Embodiments include positron emission tomographic probes that noninvasively detect and stage pulmonary fibrosis.

Embodiments also include targeted molecular imaging probes for positron emission tomography, single photon emission computed tomography for detection and staging of fibrosis in the lung, heart, liver, vessels, bone marrow, etc.

General Materials and Methods

All chemicals were purchased commercially and used without further purification. The ($^t$Bu)$_2$NOTA-NHS was purchased from Chematech (Dijon, France). The 1,4,7-triazacyclononane (TACN) was purchased from Chematech (Dijon, France). ($^t$Bu)$_3$NODAGA-COOH was synthesized in-house following a published procedure. (Levy, S. G.; Jacques, V.; Zhou, K. L.; Kalogeropoulos, S.; Schumacher, K.; Amedio, J. C.; Scherer, J. E.; Witowski, S. R.; Lombardy, R.; Koppetsch, K. Org. Process Res. Dev. 2009, 13, 535.).

($^t$Bu)NODAGA-NHS Ester.

4-(4,7-bis(2-(tert-butoxy)-2-oxoethyl)-1,4,7-triazacy-clononan-1-yl)-5-(tert-butoxy)-5-oxopentanoic acid (($^t$Bu)NODAGA-OH, 141 mg, 0.26 mmol, 1 equiv.), N,N,N',N'-tetramethyl-O-(1H-benzotriazol-1-yl)uronium hexafluorophosphate, O-(benzotriazol-1-yl)-N,N,N',N'-tetramethyluronium hexa-fluorophosphate (HBTU, 118 mg, 0.31 mmol, 1.2 equiv.) and N-hydrosuccinimide (NHS, 36 mg, 0.32 mmol, 1.2 equiv.) were dissolved in 15 mL of CH$_3$CN and stirred at room temperature for 24 hours. After removal of the solvent under reduced pressure, the resulting residue was redissolved in dichloromethane (DCM) and then promptly washed with water (3×4 mL). The organic layer was dried over magnesium sulfate, filtered and evaporated to give the product as a white foam (135 mg, 0.21 mmol, yield: 81%).

High Performance Liquid Chromatography (HPLC) Methods.

High performance liquid chromatography (HPLC) electrospray mass spectrometry (LC-MS) was performed using an Agilent 1260 Series HPLC unit with an Agilent diode array detector (using UV detection at 220, 254, and 280 nm) employing a Phenomenex Kinetex C18 column (100 mm×4.6 mm×2.6 µm). Reverse-phase semi-preparative purification was performed on a Dynamax HPLC system with a Dynamax absorbance detector using a Phenomenex Luna C18 column (250 mm×21.2 mm×5 µm). Analytical HPLC and radio-HPLC analyses were performed using Agilent 1100 Series HPLC units with an Agilent diode array detector employing a Phenomenex Kinetex C18 column (150 mm×4.6 mm×5 µm) and a Phenomenex Luna C18 column (150 mm×4.6 mm×5 µm) respectively. Different HPLC methods were used depending on whether HPLC was being used for either purification or to assess purity. Method 1 used a flow rate of 15 mL/min; mobile phase A was 0.1% trifluoroacetic acid (TFA) in H$_2$O; and mobile phase B was 0.1% TFA in CH$_3$CN; 0-7 min: 5% B, 7-30 min: 5-40% B, 30-40 min: 40-45%. Method 2 used a flow rate of 15 mL/min; mobile phase A was 0.1% TFA in H$_2$O; and mobile phase B was 0.1% TFA in CH$_3$CN; 0-15 min: 15-35% B, 15-35 min: 35-55%. Method 3 used a flow rate of 0.7 mL/min; mobile phase A was 0.1% Formic acid (FA) in H$_2$O; and mobile phase B was 0.1% FA in CH$_3$CN; 0-10 min: 5-95% B, 10-12 min: 95% B, 12-12.5 min: 95-5% B, 12.5-15 min: 5% B. Method 4 used a flow rate of 1 mL/min; mobile phase A was 0.1% TFA in H$_2$O; and mobile phase B was 0.1% TFA in CH$_3$CN; 0-13 min: 5-95% B, 13-16 min: 95% B, 16-16.5 min: 95-5% B, 16-18 min: 5% B. Method 5 used a flow rate of 1 mL/min; mobile phase A was 0.1% TFA in H$_2$O; and mobile phase B was 0.1% TFA in CH$_3$CN; 0-15 min: 32% B, 15-15.5 min: 32-95% B, 15.5-19 min: 95% B, 19-19.5 min: 95-32% B, 19.5-23 min: 32% B.

Example 1

Synthesis of $^{64}$Cu-CBP1

Pep(1).

Figure 2A:
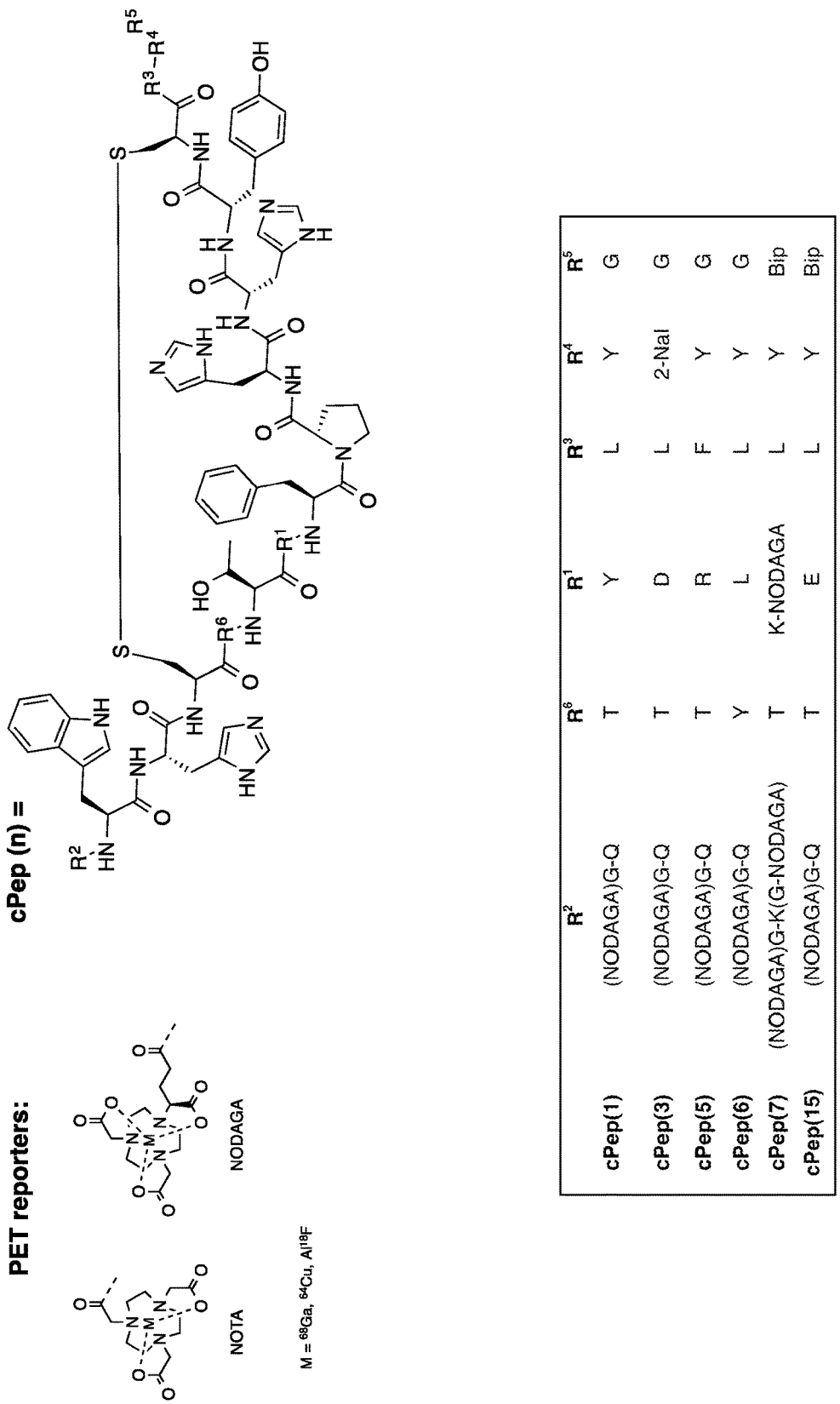
FIG. 2A is a set of diagrams and table showing general structures of collagen-binding peptides cPep(n) and PET reporters suitable for use in the invention.
Figure 2B:
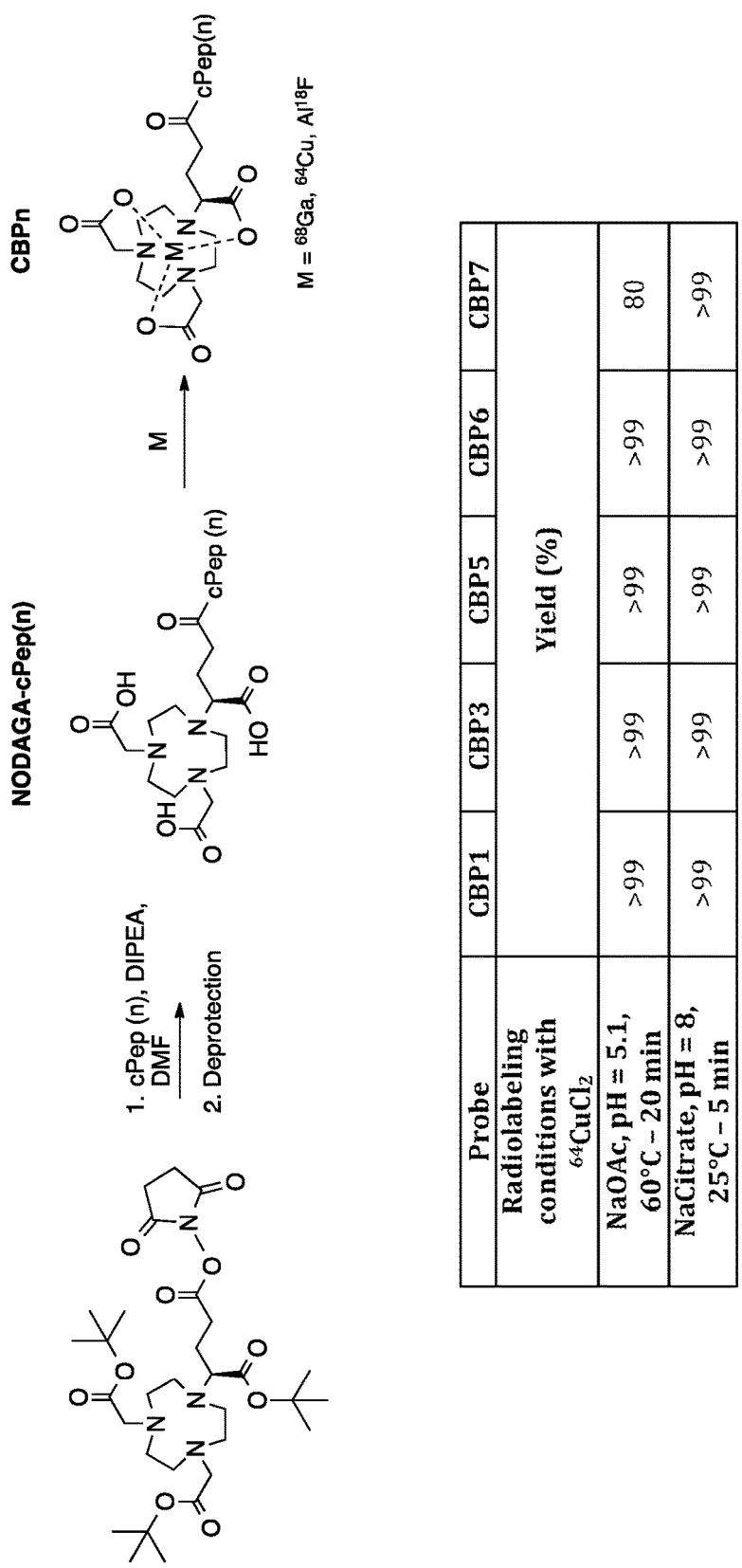
FIG. 2B is a set of diagrams and table showing general synthetic protocol for synthesizing copper-labeled PET probes—$CBP_n$ (n=1, 3, 5, 6, 7), suitable for use in the invention.
Figure 2C:
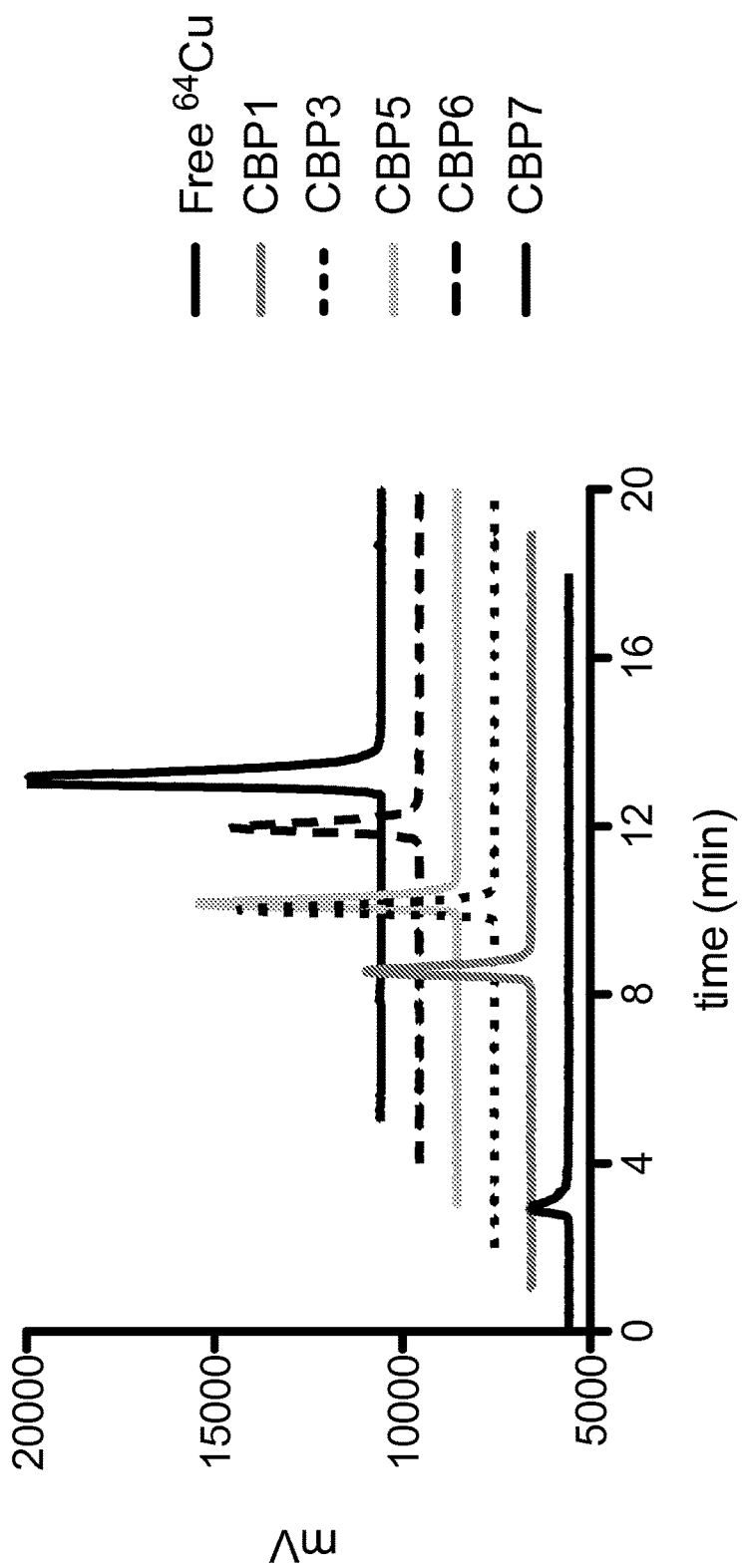
FIG. 2C is a set of graphs showing radio-HPLC analysis of copper-labeled PET probes—$CBP_n$ (n=1, 3, 5, 6, 7).
Figure 3A:
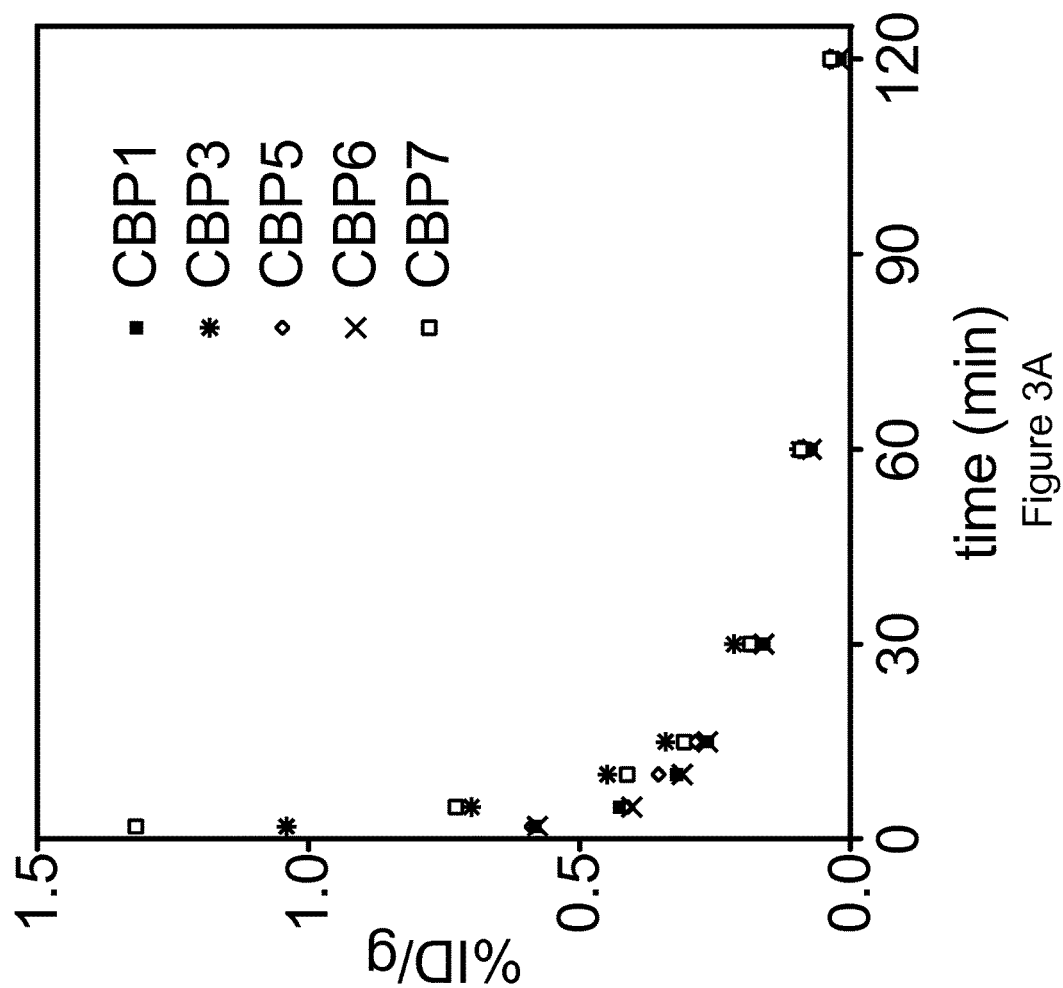
FIG. 3A is a graph showing pharmacokinetic data from ex-vivo blood analysis indicating the total $Cu^{64}$ activity in the blood (n=1/probe) after serial blood draws were taken from 0 to 120 minutes post probe injection.
Figure 3B:
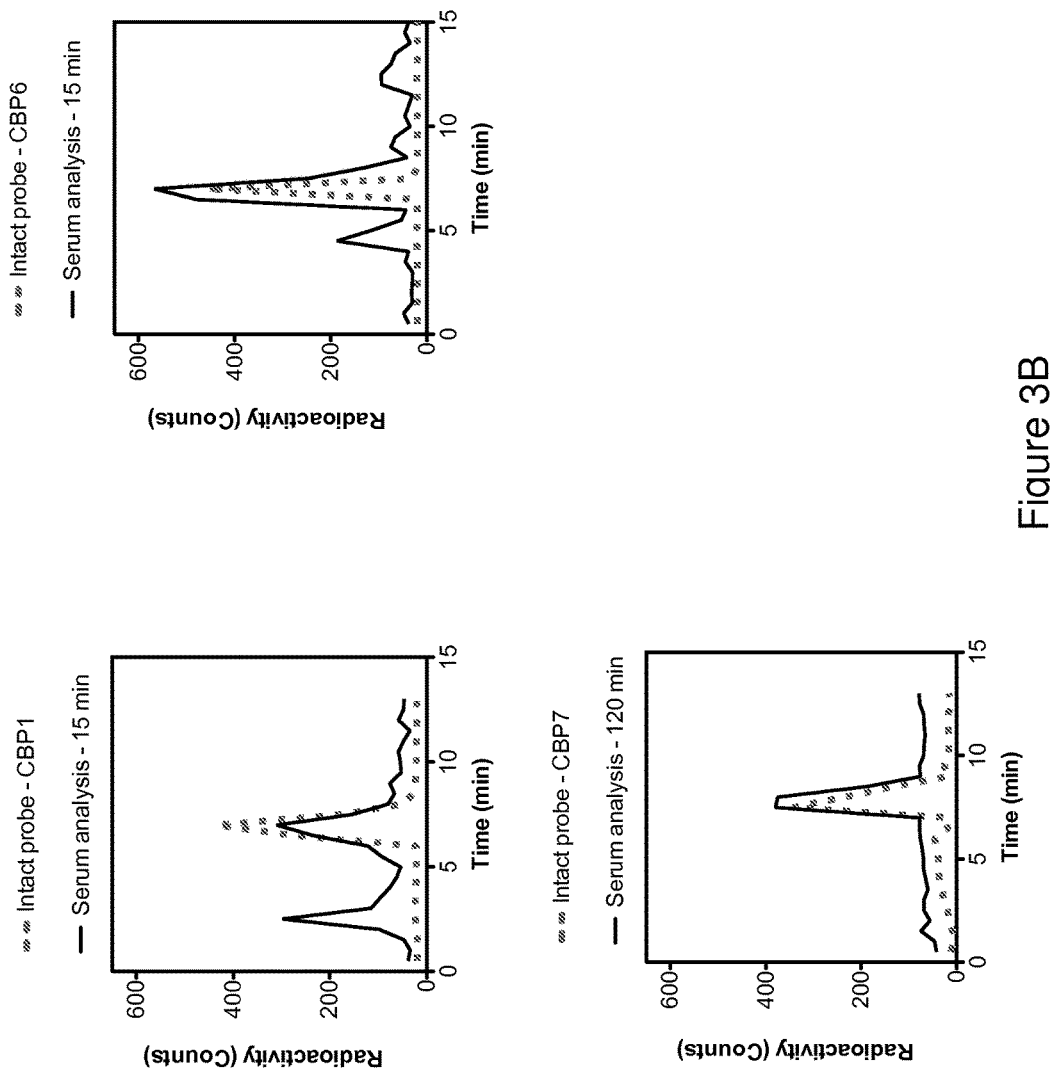
FIG. 3B is a set of graphs showing representative radio-HPLC traces of intact probe (dash line) and that from blood collected at 15 post CBP1 or CBP6 injection and from blood collected at 120 minutes post CBP7 injection and CBP7 respectively (solid line).
Figure 3C:
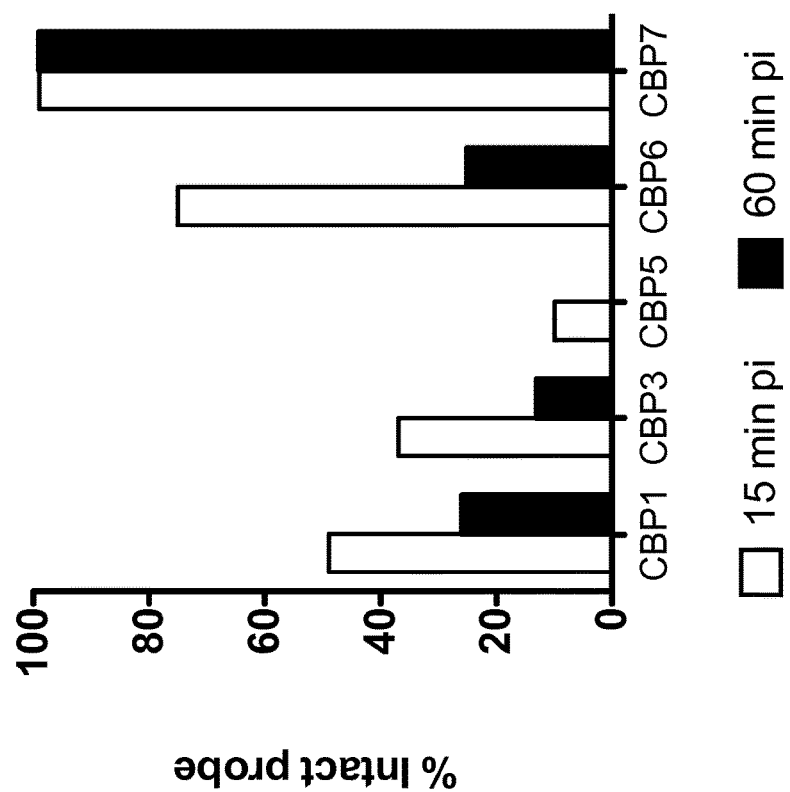
FIG. 3C is a graph showing examples of metabolic stability of copper-labeled collagen-binding probes estimated from HPLC analysis of blood samples at 15 minutes and 60 minutes post probe injection.
Figure 4A:
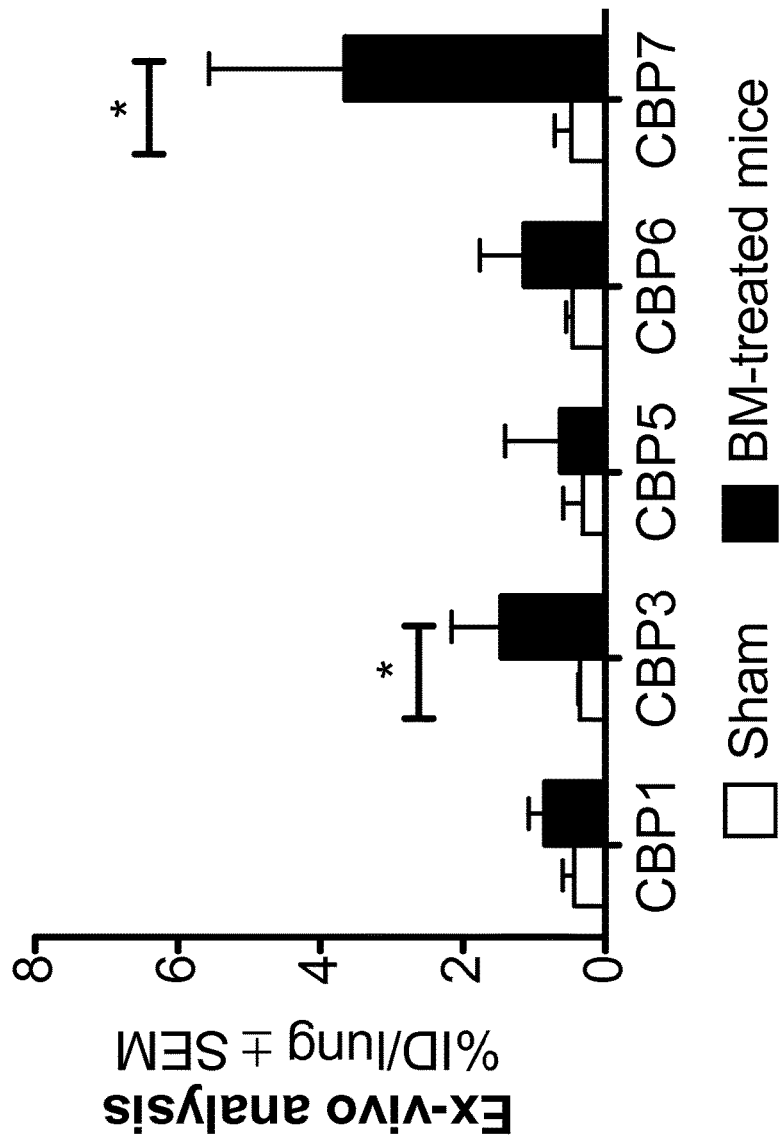
FIG. 4A is a graph showing the ex-vivo lung uptake of CBP1, CBP3, CBP5, CBP6 and CBP7 at 150 minutes post probe injection in the mouse model of pulmonary fibrosis (injection of bleomycin, 2.5 U/kg in PBS 13 days before imaging, sham received only PBS). Error bars=standard error of the mean (SEM).
Figure 4B:
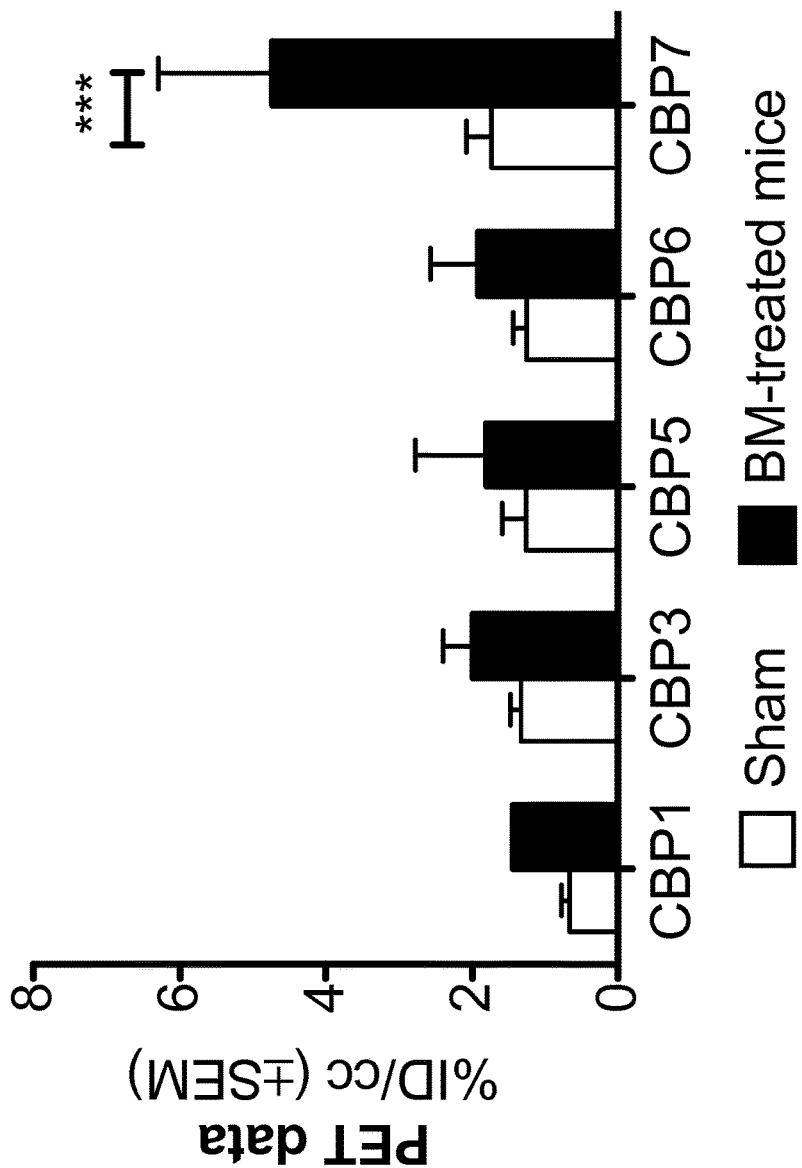
FIG. 4B is a graph showing mean lung PET activity values of CBP1, CBP3, CBP5, CBP6 and CBP7 from data 100-120 minutes post probe injection in the mouse model of pulmonary fibrosis (injection of bleomycin, 2.5 U/kg in PBS 13 days before imaging, sham received only PBS). Error bars=standard error of the mean (SEM).
Figure 4C:
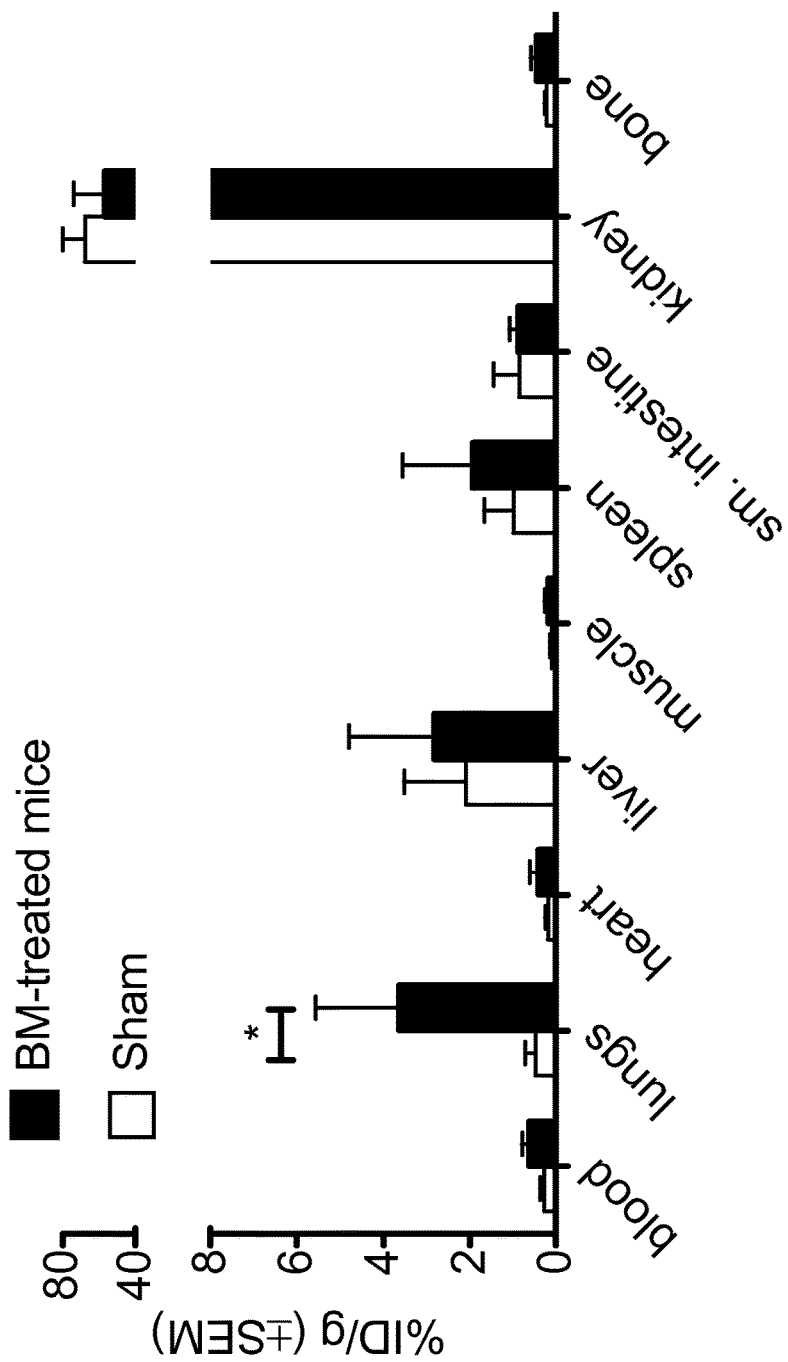
FIG. 4C is a graph showing full biodistribution of CBP7 at 120 minutes post probe injection. Error bars=standard error of the mean (SEM).
Figure 4D:
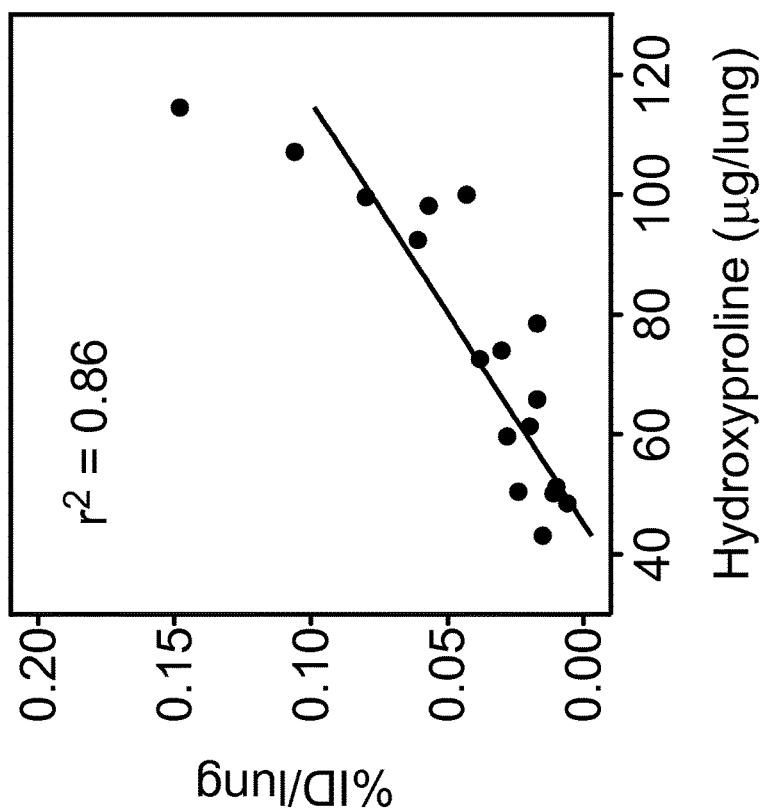
FIG. 4D is a graph showing ex vivo analysis of CBP7 (AD/lung) and hydroxyproline (collagen) content in the bleomycin model of pulmonary fibrosis.
Figure 4E:
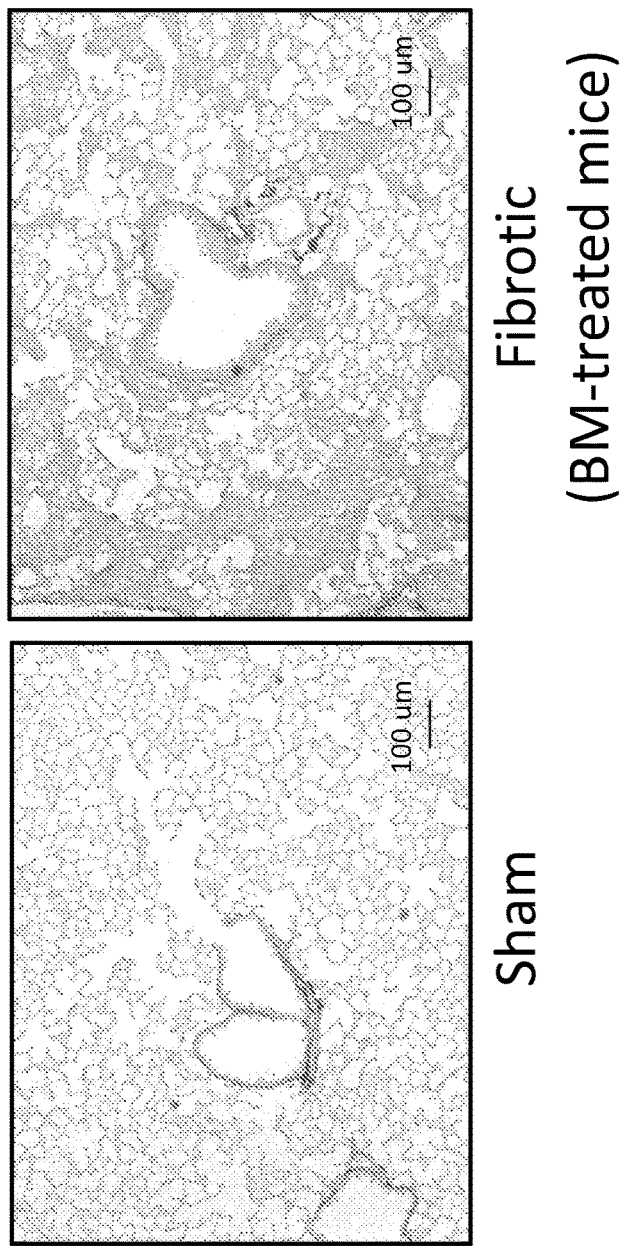
FIG. 4E is a set of images showing data of Sirius red staining of a sham and a bleomycin-treated mouse (injection of bleomycin, 2.5 U/kg in PBS 13 days before imaging, sham received only PBS).
Figure 4F:
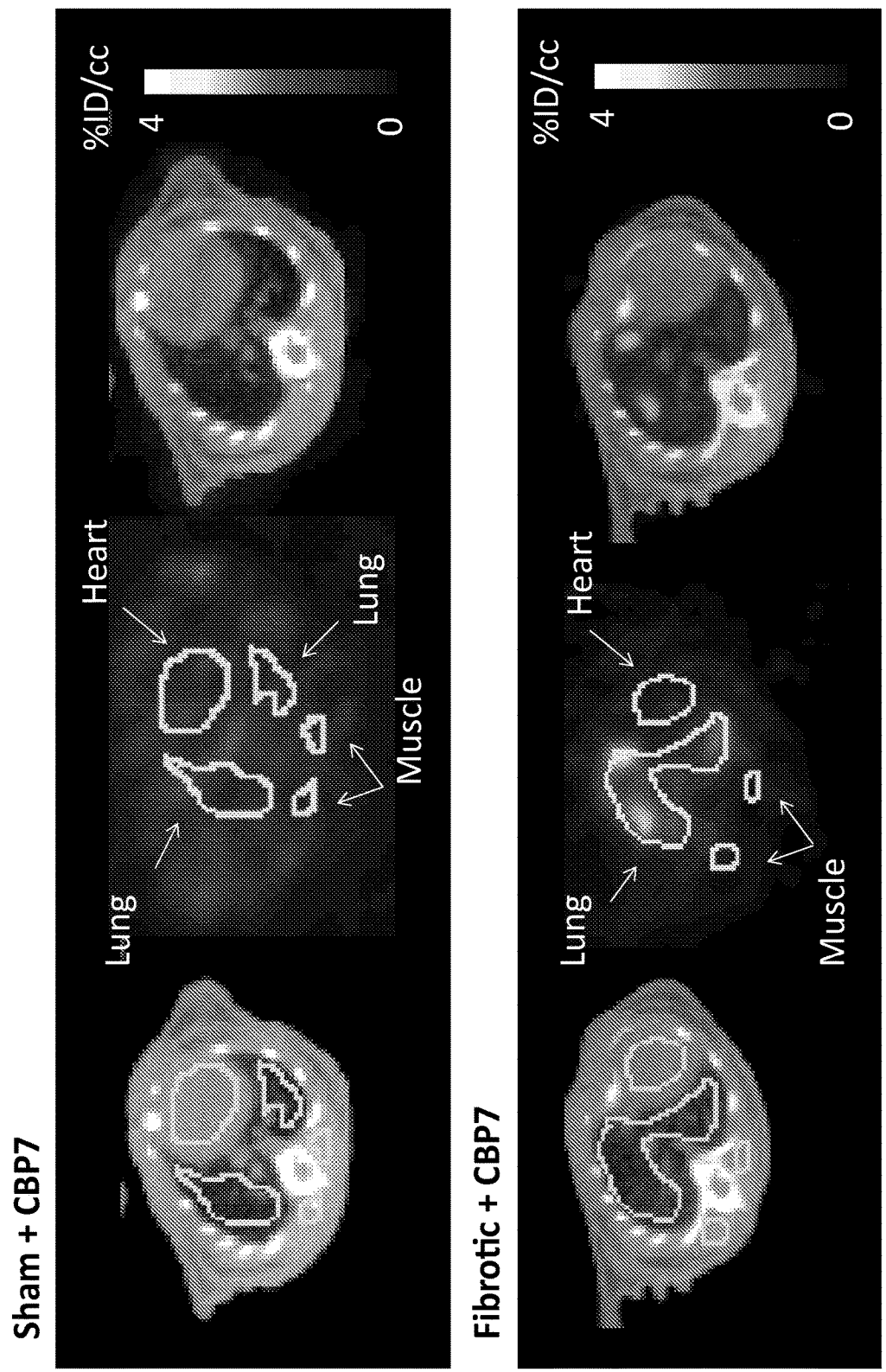
FIG. 4F is a set of CT, PET and fused PET-CT images 120 post injection of CBP7 in a sham and a bleomycin-treated mice (injection of bleomycin, 2.5 U/kg in PBS 13 days before imaging, sham received only PBS).
Figure 5:
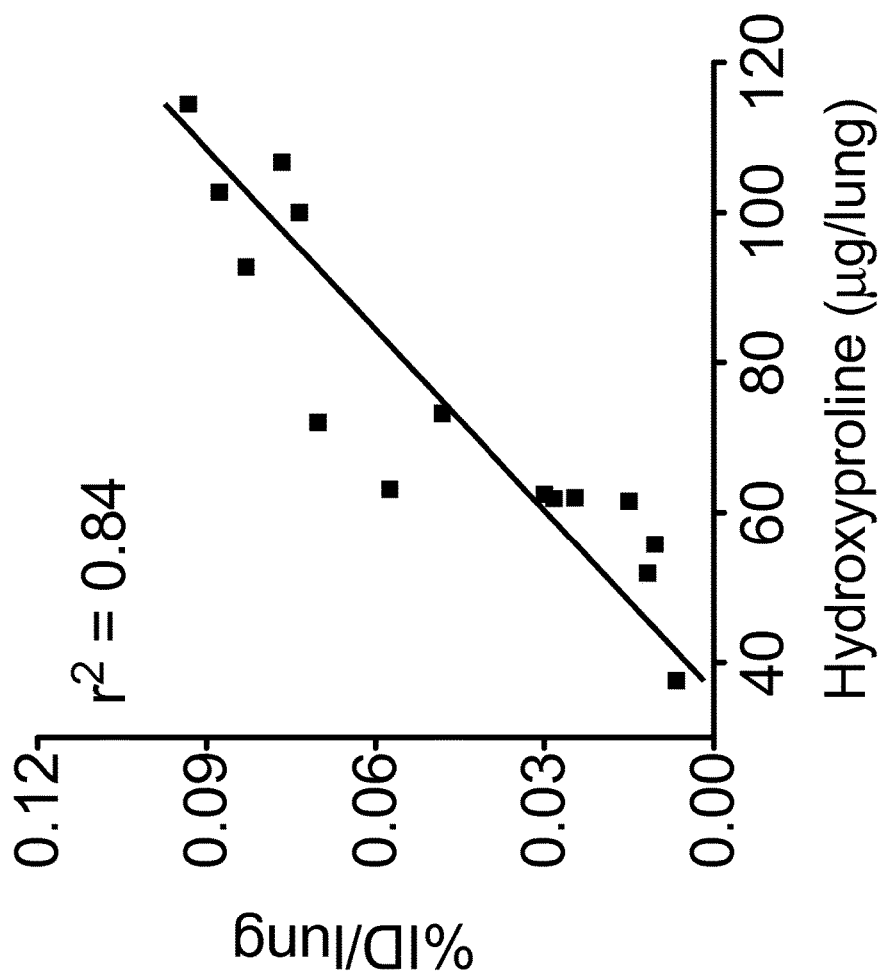
FIG. 5 is a graph showing correlation of ex-vivo lung uptake (AD/lung) of CBP8 with hydroxyproline (collagen) content of the lung in sham and bleomycin-treated mouse (injection of bleomycin, 2.5 U/kg in PBS 13 days before imaging, sham received only PBS).
Figure 6:
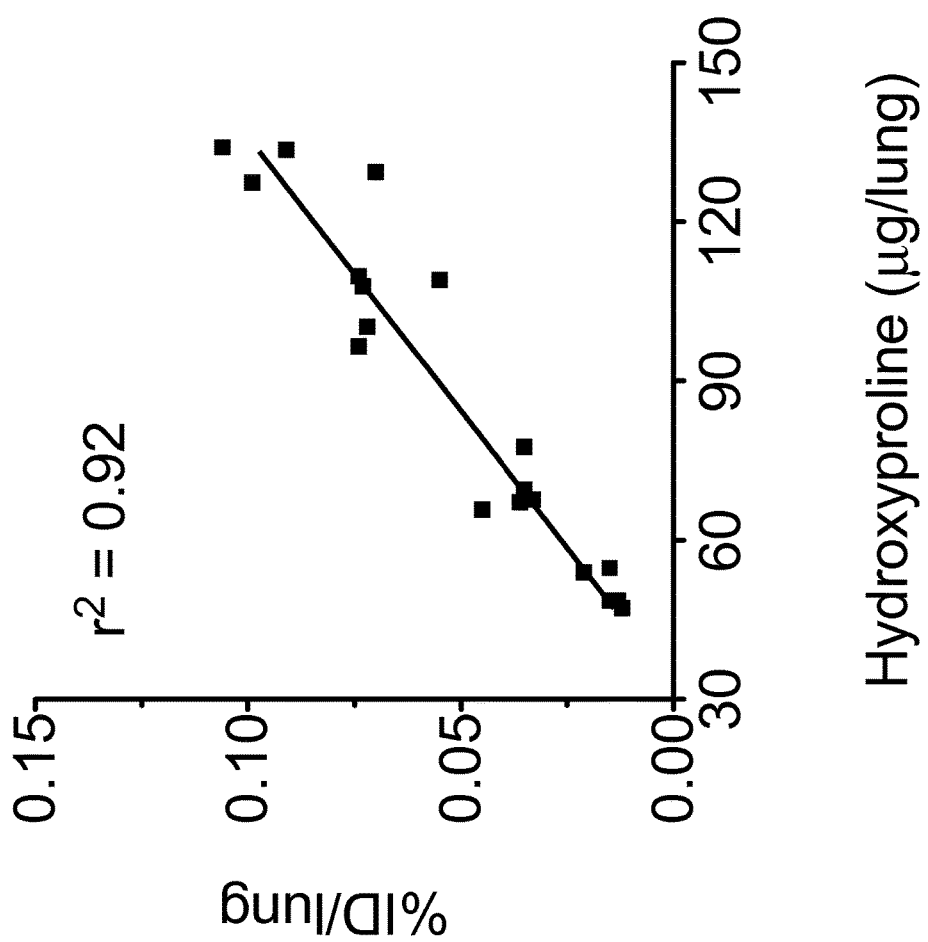
FIG. 6 is a graph showing correlation of ex-vivo lung uptake (AD/lung) of CBP8 with hydroxyproline (collagen) content of the lung in three cohorts FTY-, (LD BM)- and (FTY+LD)-treated animals.
Figure 7:
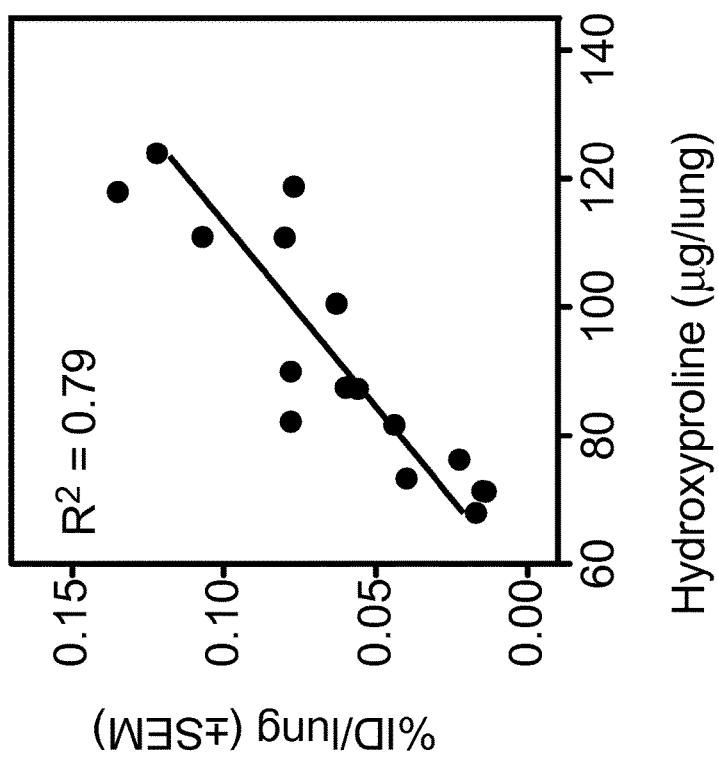
FIG. 7 is a graph showing correlation of ex-vivo lung uptake (AD/lung) of CBP8 with hydroxyproline (collagen) content of the lung in three cohorts (FTY+LD+3G9)-, (LD BM+1E6)- and 3G9-treated mice.

The CPB1 peptide (see FIG. 2A) was prepared on resin and synthesized by standard Fmoc chemistry using solid-phase peptide synthesis on a OEM microwave peptide synthesizer (Matthews, N.C.) on a 0.1 mmol scale using microwave assisted solid phase synthesis using Rink amide MBHA resin (EMD Millipore), FMOC protected amino acids (Novabiochem) and 2-(1H-benzotriazole-1-yl)-1,1,3,3-tetramethyl-uronium hexafluorophosphate (HBTU) coupling chemistry. Side chain protections of the amino acids used were the following: glutamine, cysteine, histidine: trityl; arginine: 2,2,4,6,7-pentamethyldihydro-benzofuran-5-sulfonyl; aspartic acid: tert-butyl; lysine, tryptophane: tert-butoxycarbonyl; and threonine: tert-butyl. The protected amino acids were dissolved in dimethylformamide (DMF), (0.2 M) the activator HBTU solution was prepared in DMF (0.45 M) and the activator base, diisopropylethylamine (DIPEA), was prepared in N-Methylpyridinone NMP (2M). The deprotection mix was prepared as a 20% v/v solution of piperidine in DMF with 0.1 M 1-hydroxybenzotriazole (HOBt) hydrate. The synthesis was accomplished using the OEM Liberty Microwave Peptide synthesis system. The microwave synthesis begins with transfer of Rink amide resin (167 mg, 0.1 mmol) in ca. 10 mL of DMF to the reaction vessel where the solvent was filtered and the resin was washed with DMF (7 mL) followed by dichloromethane (DCM) (7 mL) for 3 cycles. A wait time of 900 seconds allows the resin to swell. The resin was then subjected to the deprotection solvent (20% piperidine in DMF, 7 mL) and was irradiated by microwave at 75° C. using 20 watts for 300 seconds. The solution was filtered, washed with DMF (5 mL) and again subjected to the deprotection solvent and irradiated at 75° C. for 300 seconds. The solution was filtered, washed with DMF (4*7 mL) and filtered. The first Fmoc-protected amino acid was added (10 equiv., 2.5 mL), followed by the activator solution (HBTU in DMF, 10 equiv., 1.0 mL) and finally the activator base (35% DIPEA in NMP, 10 equiv., 0.5 mL). The reaction vessel was heated to 75° C. (only 50° C. for histidine and cysteine) using microwave irradiation at 20 watts for 300 seconds. The resin was filtered and washed with DMF (3*7 mL). Each amino acid was added sequentially from the C-terminus to the N-terminus using the same procedure. Upon completion of the sequence, the filtered resin was transferred back to the 50 mL Falcon tube using DCM as the carrier solvent (3*7 mL). The resin was filtered through a medium porosity Büchner funnel and transferred back to the Falcon tube. The peptides were cleaved with a cocktail comprising TFA/MSA (70% in H$_2$O)/TIPS/DDT, then precipitated in diethyl ether, and purified on semi-preparative HPLC using Method 1. The purity of each fraction was assessed by LC-MS (Method 3). The pure fractions (purity>99%) were then collected and lyophilized to give the products as white powders. Pep(1):

Molecular weight for $C_{99}H_{126}N_{26}O_{23}S_2$, MS(ESI) calc: 1057.1 [(M+2H)/2]$^{2+}$; found: 1057.0.

cPep(1).

The linear peptide, about 30 mg, was dissolved in a solution of DMSO/H$_2$O (1/15, 16 mL) and the solution was adjusted to pH 5.5 using a 0.1 M solution of sodium hydroxide. The cyclization reaction was stirred at room temperature for 24 h and monitored by LC-MS using Method 3, and the reaction mixture was purified by preparative HPLC using Method 1. The product eluted from the column at approximately 34-40% of solvent B. The pure fractions (purity>99%) were collected and lyophilized to give the products as white powders (yield>90%). cPep(1): Molecular weight for $C_{99}H_{124}N_{26}O_{23}S_2$, MS(ESI) calc: 1056.1 [(M+2H)/2]$^{2+}$; found: 1056.5.

($^t$Bu)NODAGA-Pep(1).

One equiv. of ($^t$Bu)NODAGA-NHS was added to a solution of cPep(1) in 1 mL DMF. The pH of the solution was adjusted to 6.5 by using DIPEA and the mixture was stirred at room temperature for 24 hours. The reaction mixture was purified separately by preparative HPLC using method 2. The product eluted from the column at approximately 33-36% B. ($^t$Bu)NODAGA-cPep(1): Molecular weight for $C_{126}H_{171}N_{29}O_{30}S_2$. MS(ESI): calc: 1319.0 [(M+2H)/2]$^{2+}$; found: 1318.0.

NODAGA-Pep(1).

($^t$Bu)NODAGA-Pep(1) was deprotected in a 1 mL solution of TFA, methanesulfonic acid, 1-dodecanethiol and H$_2$O (92:3:3:2). The reaction mixture was stirred for 2 hours. Cold diethylether was added to precipitate a solid. The mixture was centrifuged, and the supernatant removed. The solid was washed with diethylether and dried to give a product as a white solid. NODAGA-cPep(1): Molecular weight for $C_{114}H_{147}N_{29}O_{30}S_2$. MS(ESI): calc: 1234.9 [(M+2H)/2]$^{2+}$; found: 1234.6.

$^{64}$Cu-CBP1.

$^{64}$CuCl$_2$ (0.1-0.4 mCi, in 30 μL) was diluted with 90 μL of pH 5.1 ammonium acetate (40 mM). A sample of 10 μL of a 0.1 mM NODAGA-cPep(1) solution (in sodium acetate pH 4.1) was added and the reaction mixture was heated at 60° C. for 15 min. The radiochemical purity of the final solution was ≥99% as determined by radio-HPLC using method 5: retention time of 7.54 minutes for CBP1. The pH was adjusted to 7.4 using PBS and diluted in sucrose (18 mM in water) before injection into animals.

Example 2

Synthesis of $^{64}$Cu-CBP3

Pep(3).

The CPB3 peptide (see FIG. 2A) was prepared using the same conditions as in Example 1. Pep(3): Molecular weight for $C_{98}H_{124}N_{26}O_{23}S_2$, MS(ESI) calc: 1050.2 [(M+2H)/2]$^{2+}$; found: 1050.5.

cPep(3).

The linear Pep(3) peptide, about 30 mg, was cyclized and purified using the same conditions as in Example 1, (yield>90%, purity 99%). cPep(3): Molecular weight for $C_{98}H_{122}N_{26}O_{23}S_2$, MS(ESI) calc: 1049.2 [(M+2H)/2]$^{2+}$; found: 1049.2.

($^t$Bu)NODAGA-Pep(3).

($^t$Bu)NODAGA-NHS was conjugated to the N-terminus of cPep(3) using the same conditions as in Example 1. The product eluted from the column at approximately 33-36% B.

($^t$Bu)NODAGA-cPep(3): Molecular weight for $C_{125}H_{169}N_{29}O_{30}S_2$. MS(ESI): calc: 1312.0 [(M+2H)/2]$^{2+}$; found: 1311.3.

NODAGA-Pep(3).

($^t$Bu)NODAGA-Pep(3) was deprotected using the same conditions as in Example 1. NODAGA-cPep(3): Molecular weight for $C_{113}H_{145}N_{29}O_{30}S_2$. MS(ESI): calc: 1227.9 [(M+2H)/2]$^{2+}$; found: 1227.1. $^{64}$Cu-CBP3. $^{64}$CuCl$_2$ (0.1-0.4 mCi, in 30 μL) was diluted with 90 μL of pH 5.1 ammonium acetate (40 mM). A sample of 10 μL of a 0.1 mM NODAGA-cPep(3) solution (in sodium acetate pH 4.1) was added and the reaction mixture was heated at 60° C. for 15 min. The radiochemical purity of the final solution was ≥99% as determined by radio-HPLC using method 5: retention time of 8.02 minutes for CBP1. The pH was adjusted to 7.4 using PBS and diluted in sucrose (18 mM in water) before injection into animals.

Example 3

Synthesis of $^{64}$Cu-CBP5

Pep(5).

The CPB5 peptide (see FIG. 2A) was prepared using the same conditions as in Example 1. Pep(5): Molecular weight for $C_{99}H_{127}N_{29}O_{22}S_2$, MS(ESI) calc: 1070.7 [(M+2H)/2]$^{2+}$; found: 1070.2.

cPep(5).

The linear Pep(5) peptide, about 30 mg, was cyclized and purified using the same conditions as in Example 1, (yield>90%, purity 99%). cPep(5): Molecular weight for $C_{99}H_{125}N_{29}O_{22}S_2$, MS(ESI) calc: 1069.7 [(M+2H)/2]$^{2+}$; found: 1069.6.

($^t$Bu)NODAGA-Pep(5).

($^t$Bu)NODAGA-NHS was conjugated to the N-terminus of cPep(5) using the same conditions as in Example 1. The product eluted from the column at approximately 33-36% B. ($^t$Bu)NODAGA-cPep(5): Molecular weight for $C_{126}H_{172}N_{32}O_{29}S_2$. MS(ESI): calc: 1332.5 [(M+2H)/2]$^{2+}$; found: 1331.7.

($^t$Bu)NODAGA-Pep(5).

($^t$Bu)NODAGA-Pep(5) was deprotected using the same conditions as in Example 1. NODAGA-cPep(5): Molecular weight for $C_{114}H_{148}N_{32}O_{29}S_2$. MS(ESI): calc: 1248.4 [(M+2H)/2]$^{2+}$; found: 1247.5.

$^{64}$Cu-CBP5.

$^{64}$CuCl$_2$ (0.1-0.4 mCi, in 30 μL) was diluted with 90 μL of pH 5.1 ammonium acetate (40 mM). A sample of 10 μL of a 0.1 mM NODAGA-cPep(5) solution (in sodium acetate pH 4.1) was added and the reaction mixture was heated at 60° C. for 15 min. The radiochemical purity of the final solution was ≥99% as determined by radio-HPLC using method 5: retention time of 7.18 minutes for CBP1. The pH was adjusted to 7.4 using PBS and diluted in sucrose (18 mM in water) before injection into animals.

Example 4

Synthesis of $^{64}$Cu-CBP6

Pep(6).

The CPB6 peptide (see FIG. 2A) was prepared using the same conditions as in Example 1. Pep(6): Molecular weight for $C_{101}H_{130}N_{26}O_{22}S_2$, MS(ESI) calc: 1063.2 [(M+2H)/2]$^{2+}$; found: 1063.0.

cPep(6).

The linear Pep(6) peptide, about 30 mg, was cyclized and purified using the same conditions as in Example 1, (yield>90%, purity 99%). cPep(6): Molecular weight for $C_{101}H_{128}N_{26}O_{22}S_2$, MS(ESI) calc: 1062.2 [(M+2H)/2]$^{2+}$; found: 1061.6.

($^t$Bu)NODAGA-Pep(6).

($^t$Bu)NODAGA-NHS was conjugated to the N-terminus of cPep(6) using the same conditions as in Example 1. The product eluted from the column at approximately 33-36% B. ($^t$Bu)NODAGA-cPep(6): Molecular weight for $C_{128}H_{175}N_{29}O_{29}S_2$. MS(ESI): calc: 1325.0 [(M+2H)/2]$^{2+}$; found: 1331.7.

NODAGA-Pep(6).

($^t$Bu)NODAGA-Pep(6) was deprotected using the same conditions as in Example 1. NODAGA-cPep(6): Molecular weight for $C_{116}H_{151}N_{29}O_{29}S_2$. MS(ESI): calc: 1240.8 [(M+2H)/2]$^{2+}$; found: 1233.7. $^{64}$Cu-CBP6. $^{64}$CuCl$_2$ (0.1-0.4 mCi, in 30 µL) was diluted with 90 µL of pH 5.1 ammonium acetate (40 mM). A sample of 10 µL of a 0.1 mM NODAGA-cPep(6) solution (in sodium acetate pH 4.1) was added and the reaction mixture was heated at 60° C. for 15 min. The radiochemical purity of the final solution was ≥99% as determined by radio-HPLC using method 5: retention time of 7.96 minutes for CBP1. The pH was adjusted to 7.4 using PBS and diluted in sucrose (18 mM in water) before injection into animals.

Example 5

Synthesis of $^{64}$Cu-CBP7

Pep(7).

The CPB7 peptide (see FIG. 2A) was prepared using the same conditions as in Example 1. Pep(7): Molecular weight for $C_{110}H_{143}N_{27}O_{21}S_2$, MS(ESI) calc: 748.8 [(M+3H)/3]$^{3+}$; found: 749.0.

cPep(7).

The linear Pep(7) peptide, about 30 mg, was cyclized and purified using the same conditions as in Example 1, (yield>90%, purity 99%). cPep(7): Molecular weight for $C_{110}H_{141}N_{27}O_{21}S_2$, MS(ESI) calc: 748.2 [(M+3H)/3]$^{3+}$; found: 749.0.

($^t$Bu)NODAGA-Pep(7).

Three equiv. of ($^t$Bu)NODAGA-NHS were added on a solution of cPep(7) in 1 mL DMF. The pH of the solution was adjusted to 6.5 by using DIPEA and the mixture was stirred at room temperature for 24 hours. The reaction mixture was purified by preparative HPLC using method 1 (elution at 45% B with a retention time of 34 minutes). ($^t$Bu)NODAGA-cPep(7): Molecular weight for $C_{193}H_{285}N_{37}O_{43}S_2$. MS(ESI): calc: 970.0[(M+4H)/4]$^{4+}$; found: 969.9.

NODAGA-Pep(7).

($^t$Bu)NODAGA-Pep(7) was deprotected using the same conditions as in Example 1. NODAGA-cPep(7): Molecular weight for $C_{157}H_{213}N_{37}O_{43}S_2$. MS(ESI): calc: 843.8 [(M+4H)/4]$^{4+}$; found: 843.4. $^{64}$Cu-CBP7. $^{64}$CuCl$_2$ was diluted with 90 µL of pH 8 sodium citrate (10 mM). A sample of 10 µL of a 0.1 mM NODAGA-cPep(7) solution (in HEPES pH 7.4) was added and the reaction mixture was stirred at room temperature for 5 minutes. The radiochemical purity of the final solution was ≥99% as determined by radio-HPLC using method 5: retention time of 7.54 minutes for CBP7. The pH was adjusted to 7.4 using PBS and the solution diluted in sucrose (18 mM in water) before injection into animals.

Example 6

Synthesis of $^{68}$Ga-CBP8

$^{68}$GaCl$_3$ (10 mCi, in 0.5 mL HCl (0.6 M)) was diluted with 200 µL of pH 5 sodium acetate (3 M) to reach pH 4.1. A sample of 180 µL of the $^{68}$GaCl$_3$ solution was combined to 10 µL of a 0.1 mM NODAGA-cPep(7) solution (in sodium acetate pH 4.1) and the reaction mixture was heated at 60° C. for 5 minutes and purified by Sep-Pak 18 cartridge (Waters) to remove any radiometal impurities (traces of $^{68}$Ge). The radiochemical purity of the final solution was ≥99% as determined by radio-HPLC using method 5: retention time of 7.9 min for CBP8. The pH was adjusted to 7.4 using PBS and the radio-labeled CBP8 was diluted in sucrose (80 mM in water) before injection into animals.

Example 7

Synthesis of Al$^{18}$F-CBP9

Na$^{18}$F in 2 mL of water was loaded onto a Sep-Pak Light, Waters Accell QMA Plus Cartridge that was prewashed with 10 mL of 0.4 M KHCO$_3$, followed by 10 mL of water. After loading the $^{18}$F$^-$ onto the cartridge, it was washed with 5 mL of water to remove any dissolved metal and radiometal impurities. The isotope was then eluted with about 1 mL of 0.4 M KHCO$_3$ in several fractions to isolate the fraction with the highest concentration of activity. The eluted fractions were acidified to pH 4.7 with glacial acetic acid. Then, 15 µL of a 2.5 mM solution of NODAGA-cPep(7) in DMF was mixed with 6 nmol of AlCl$_3$ (2 mM solution in 0.1 M sodium acetate buffer, pH=4.7) and approximately 7 mCi of $^{18}$F$^-$, heated for 15 minutes at 104° C. and purified by Sep-Pak 18 cartridge (Waters). The radiochemical purity of the final solution was ≥99% as determined by radio-HPLC using method 5: retention time of 8.1. The pH was adjusted to 7.4 using PBS and the radio-labeled CBP9 was diluted in sucrose (18 mM in water) before injection into animals.

Example 8

Synthesis of Al$^{18}$F-CBP10

NOTA-cPep(7).

Three equivalents of ($^t$Bu)$_2$NOTA-NHS were added to a solution of cPep(7) in 1 mL DMF. The pH of the solution was adjusted to 6.5 using DIPEA and the mixture was stirred at room temperature for 24 hours. ($^t$Bu)$_2$NOTA-cPep(7) was purified by preparative HPLC using Method 1 (elution at 33% of solvent B with a retention time of 21 minutes). ($^t$Bu)$_2$NOTA-cPep(7): Molecular weight for $C_{172}H_{249}N_{37}O_{37}S_2$. MS(ESI) calc: 873.8 [(M+4H)/4]$^{4+}$; found: 873.4. ($^t$Bu)$_2$NOTA-cPep(7) was deprotected in a 1 mL solution of TFA, methanesulfonic acid, 1-dodecanethiol and H$_2$O (92:3:3:2). the reaction mixture was stirred for 2 hours. Cold diethyl ether was added to precipitate out the solids. The mixture was centrifuged, and the supernatant removed. The solid was washed with diethyl ether and dried to give the product as a white solid. NOTA-cPep(7): Molecular weight for $C_{148}H_{201}N_{37}O_{37}S_2$, MS(ESI) calc: 789.6 [(M+4H)/4]$^{4+}$; found: 789.3.

Al$^{18}$F-NOTA-cPep(7)=Al$^{18}$F-CBP10.

Na$^{18}$F in 2 mL of water was loaded onto a Sep-Pak Light, Waters Accell QMA Plus Cartridge that was prewashed with 10 mL of 0.4 M KHCO$_3$, followed by 10 mL of water. After loading the $^{18}$F$^-$ onto the cartridge, it was washed with 5 mL of water to remove any dissolved metal and radiometal impurities. The isotope was then eluted with about 1 mL of 0.4 M KHCO$_3$ in several fractions to isolate the fraction with the highest concentration of activity. The eluted fractions were acidified to pH 4.7 with glacial acetic acid. Then, 15 µL of a 2.5 mM solution of NOTA-cPep(7) in DMF were mixed with 6 nmol of AlCl$_3$ (2 mM solution in 0.1 M sodium acetate buffer, pH=4.7) and approximately 7 mCi of $^{18}$F$^-$, heated for 15 minutes at 104° C., yielding CBP10 in 72% yield. After purification by Sep-Pak 18 cartridge (Waters), the radiochemical purity of the final solution was ≥99% as determined by radio-HPLC using method 4: retention time of 8.0 for CBP10. The pH was adjusted to 7.4 using PBS and the radiolabeled CBP10 was diluted in sucrose (80 mM in water) before injection into animals.

Example 9

Synthesis of $^{64}$Cu-CBP11

Pep(1).
The CPB11 peptide (G•K(G)•W•H•DCys•T•T•K—F•P•H—H•Y•C•L•Y•BIP) was prepared using the same conditions as in Example 1. Pep(11): Molecular weight for C$_{110}$H$_{143}$N$_{27}$O$_{21}$S$_2$, MS(ESI) calc: 748.8 [(M+3H)/3]$^{3+}$; found: 749.0.

cPep(11).
The linear Pep(11) peptide, about 30 mg, was cyclized and purified using the same conditions as in Example 1, (yield>90%, purity 99%). cPep(11): Molecular weight for C$_{110}$H$_{141}$N$_{27}$O$_{21}$S$_2$, MS(ESI) calc: 748.2 [(M+3H)/3]$^{3+}$; found: 749.0.

($^t$Bu)NODAGA-Pep(11).
Three equiv. of ($^t$Bu)NODAGA-NHS were added on a solution of cPep(11) in 1 mL DMF. The pH of the solution was adjusted to 6.5 by using DIPEA and the mixture was stirred at room temperature for 24 hours. The reaction mixture was purified by preparative HPLC using method 1 (elution at 45% B with a retention time of 34 minutes). ($^t$Bu)NODAGA-cPep(11): Molecular weight for C$_{103}$H$_{285}$N$_{37}$O$_{43}$S$_2$. MS(ESI): calc: 970.0[(M+4H)/4]$^{4+}$; found: 969.9.

NODAGA-Pep(11).
($^t$Bu)NODAGA-Pep(11) was deprotected using the same conditions as in Example 1. NODAGA-cPep(11): Molecular weight for C$_{157}$H$_{213}$N$_{37}$O$_{43}$S$_2$, MS(ESI) calc: 843.8 [(M+4H)/4]$^{4+}$; found: 843.4.

$^{64}$Cu-CBP11.
$^{64}$CuCl$_2$ was diluted with 90 µL of pH 8 sodium citrate (10 mM). A sample of 10 µL of a 0.1 mM NODAGA-cPep(11) solution (in HEPES pH 7.4) was added and the reaction mixture was stirred at room temperature for 5 minutes. The radiochemical purity of the final solution was ≥99% as determined by radio-HPLC using method 5: retention time of 8.2 minutes for CBP11. The pH was adjusted to 7.4 using PBS and the solution diluted in sucrose (18 mM in water) before injection into animals.

Example 10

Synthesis of $^{68}$Ga-CBP12

$^{68}$GaCl$_3$ (10 mCi, in 0.5 mL HCl (0.6 M)) was diluted with 200 µL of pH 5 sodium acetate (3 M) to reach pH 4.1.

A sample of 180 µL of the $^{68}$GaCl$_3$ solution was combined to 10 µL of a 0.1 mM NODAGA-cPep(11) solution (in sodium acetate pH 4.1) and the reaction mixture was heated at 60° C. for 5 minutes and purified by Sep-Pak 18 cartridge (Waters) to remove any radiometal impurities (traces of $^{68}$Ge). The radiochemical purity of the final solution was ≥99% as determined by radio-HPLC using method 5: retention time of 7.4 min for CBP12. The pH was adjusted to 7.4 using PBS and the radio-labeled CBP12 was diluted in sucrose (80 mM in water) before injection into animals.

Example 11

Synthesis of $^{64}$Cu-CBP15

Pep(15).
The CPB15 peptide (G•Q•W•H•C•T•T•E•F•P•H•H•Y•C•L•Y•BIP) was prepared using the same conditions as in Example 1. Pep(15): Molecular weight for C$_{108}$H$_{134}$N$_{26}$O$_{24}$S$_2$, MS(ESI) calc: 1123.0 [(M−2H)/2]$^{2+}$; found: 1123.0.

cPep(15).
The linear Pep(15) peptide, about 30 mg, was cyclized and purified using the same conditions as in Example 1, (yield>90%, purity 99%). cPep(15): Molecular weight for C$_{108}$H$_{132}$N$_{26}$O$_{24}$S$_2$, MS(ESI) calc: 1122.2 [(M+2H)/2]$^{2+}$; found: 1121.7.

($^t$Bu)NODAGA-Pep(15).
($^t$Bu)NODAGA-NHS was conjugated to the N-terminus of cPep(15) using the same conditions as in Example 1. The product eluted from the column at approximately 33-36% B. ($^t$Bu)NODAGA-Pep(15) was deprotected using the same conditions as in Example 1.

$^{64}$Cu-CBP15.
$^{64}$CuCl$_2$ (0.1-0.4 mCi, in 30 µL) was diluted with 90 µL of pH 5.1 ammonium acetate (40 mM). A sample of 10 µL of a 0.1 mM NODAGA-cPep(15) solution (in sodium acetate pH 4.1) was added and the reaction mixture was heated at 60° C. for 15 min. The radiochemical purity of the final solution was ≥99% as determined by radio-HPLC using method 5.

Example 12

Synthesis of Non-Radioactive Analogs of CBP1, CBP3, CBP5, CBP6, and CBP7

$^{63/65}$Cu-NODAGA-cPep(n) (n=1, 3, 5, 6, 7).
In separate reaction vessels each of NODAGA-Pep(n) (n=1, 3, 5, 6, 7) was dissolved in ca. 1 mL of 10 mM sodium acetate (pH=5.5). After addition of a small excess of $^{63/65}$CuSO$_4$ into the solution (1.1 equiv. for NODAGA-Pep (n), (n=1, 3, 5, 6) and 3.3 equiv. for NODAGA-Pep(7)), the reaction was stirred at 60° C. for 1 hour. To scavenge the excess of Cu$^{2+}$ ion, five equiv. of diethylenetriamine were added in the mixture. The reaction mixtures of $^{63/65}$Cu-CBP (n) (n=1, 3, 5, 6, 7) were purified separately by preparative HPLC using method 2. The fractions were collected, lyophilized, and then redissolved in water where the final concentration of each $^{63/65}$Cu-CBP(n) solution was determined using ICP-MS. The masses of all three products were confirmed by LC-MS with the expected isotopic ratios. $^{63/65}$Cu-CBP(1): Molecular weight for C$_{114}$H$_{145}$CuN$_{29}$O$_{30}$S$_2$. MS(ESI): calc: 1265.6 [(M+2H)/2]$^{2+}$; found: 1265.5. $^{63/65}$Cu-CBP(3): Molecular weight for C$_{113}$H$_{143}$CuN$_{29}$O$_{30}$S$_2$. MS(ESI): calc: 1258.6 [(M+2H)/2]$^{2+}$; found: 1258.1. $^{63/65}$Cu-CBP(5): Molecular weight for C$_{114}$H$_{146}$ $CuN_{32}O_{29}S_2$. MS(ESI): calc: 1279.1 $[(M+2H)/2]^{2+}$; found: 1279.1. $^{63/65}Cu$-CBP(6): Molecular weight for $C_{116}H_{149}CuN_{29}O_{29}S_2$. MS(ESI): calc: 1271.5 $[(M+2H)/2]^{2+}$; found: 1271.6. $^{63/65}Cu$-CBP(7) and $^{63/65}Cu$-CBP(11): Molecular weight for $C_{157}H_{207}Cu_3N_{37}O_{43}S_2$. MS(ESI): calc: 1186.0 $[(M+3H)/3]^{3+}$; found: 1186.5.

Example 13

Collagen Binding Affinity

Binding isotherms were obtained by following a method previously reported. (Caravan, P., Das, B., Dumas, S., Epstein, F. H., Helm, P. A., Jacques, V., Koerner, S., Kolodziej, A., Shen, L., Sun, W., Zhang, Z., *Angewandte Chemie*, 2007, 119(43), 8319-8321.) Briefly, increasing concentrations of a mixture of $^{63/65}Cu$-CBP(n) and $^{64}Cu$-CBP(n) were added to collagen containing wells. Wells that did not contain collagen were used to control for non-specific binding to plate. An aliquot of each solution was reserved as a measure of the total concentration. The plates were incubated on a shaker table (300 rpm) for 2 hours at room temperature to allow the compound to bind. After 2 hours, the supernatant from each well (with or without collagen) was assayed for $^{64}Cu$ content. The relative amount of free, unbound compound in the sample supernatants and the amount of compound in the reserved (total) sample were determined by using a gamma counter. The bound concentration is [Total]−[Free]. The concentration of $^{63/65}Cu$-CBP(n) was less than the collagen concentration and the data were fit to a model of a single binding site with dissociation constant, Kd.

TABLE 1

Kd values (µM) determined for collagen-binding probes CBP1, CBP3, CBP5, CBP6, CBP7 through a rat tail collagen-binding assay

| | Kd (µM) |
|---|---|
| CBP1 | 1.6 ± 1.1 |
| CBP3 | 4.4 ± 1.0 |
| CBP5 | 7.2 ± 5.2 |
| CBP6 | 14.6 ± 5.8 |
| CBP7 | 2.4 ± 1.5 |

Example 14

Generalities on PET In Vivo Imaging

Animal Model

All experiments were performed in accordance with National Institutes of Health guidelines for the care and use of laboratory animals, and were approved by the institution's animal care and use committee.

Standard-Dose Bleomycin Model.

Pulmonary fibrosis was induced in 7-8-week-old male C57/BL6 mice by transtracheal administration of bleomycin (BM; 2.5 U/kg) in 50 µL of PBS under direct vision using a small cervical incision. Sham animals received only PBS.

Low Dose Bleomycin Model Associated with a Vascular Leak Agent (Shea et al. 2010).

Adult male C57Bl/6 mice were administered a single intratracheal dose of low dose bleomycin at 0.1 U/kg (low dose), in a total volume of 50 µl sterile saline. FTY720 was administered intraperitoneally to the mice at 1 mg/kg three times a week.

Treatment Model.

To effect treatment in the low dose bleomycin, vascular leak model, the therapeutic murine antibody 3G9 (alpha-v-beta6 blocking antibody) and 1E6 (matched isotype control antibody) were used. Antibodies were injected into mice intraperitoneally three times week at a concentration of 1 mg/kg. All administrations of FTY720 and antibodies were initiated on day 0, ~30 minutes before bleomycin challenge and continued throughout the duration of the experiments.

Small Animal PET-CT Imaging Studies

Animals were placed in a small-animal PET/SPECT/CT scanner (Triumph; TriFoil Imaging), equipped with inhalation anesthesia and heating pad. Each animal was anesthetized with isoflurane (4% for induction, 1-1.5% for maintenance in medical air). After placement of an in-dwelling catheter in the femoral vein for probe administration, mice were positioned in the PET-CT and the probe was given as a bolus as the PET acquisition began. Mice were imaged continuously by PET for 120 minutes. A whole body CT was obtained either immediately before or immediately after the PET acquisition, and the mice were then euthanized at 150 minutes post injection and the organs taken for biodistribution analysis (vide supra). Instrument calibration was performed with phantoms containing small known amounts of radioactivity. Isotropic (0.3 mm) CT images were acquired over 6 minutes with 512 projections with 3 frames per projection (exposure time per frame, ~200 msec; peak tube voltage, 70 kV; tube current, 177 mA). PET and CT images were reconstructed using the LabPET software (TriFoil Imaging) and the CT data were used to provide attenuation correction for the PET reconstructions. The PET data were reconstructed using a maximum-likelihood expectation-maximization (MLEM) algorithm run over 30 iterations to a voxel size of 0.5×0.5×0.6 mm³. For the pharmacokinetic analyses, the PET data were reconstructed in 1 minute (first 10 frames), 3 min (next 10 frames), and 10 minutes (last 8-10 frames) intervals out to 120 minutes post injection. Reconstructed PET/CT data were quantitatively evaluated using AMIDE software package (Loening and Gambhir, 2003). For each PET scan, volumes of interest (VOIs) were drawn over major organs on decay-corrected whole body coronal images. The radioactivity concentration within organs was obtained from mean pixel values within the VOI volume and converted to counts per milliliter per minute and then divided by the injected dose (ID) to obtain an imaging VOI-derived percentage of the injected radioactive dose per cubic centimeter of tissue (% ID/cc). When comparing data on a % ID/cc basis we assumed that only 20% of the lungs were tissue and we corrected the value obtained from the PET data by a factor of 5.

Biodistribution Protocol

Animals were placed in a small-animal PET/SPECT/CT scanner (Triumph; TriFoil Imaging), equipped with inhalation anesthesia and heating pad. Each animal was anesthetized with isoflurane (4% for induction, 2-2.5% for maintenance in medical air) and body temperature was kept at 37-38° C. using a heating pad. The femoral vein was cannulated for intravenous delivery of the PET agent. Each mouse was injected with approximately 0.1 mL and 20-50 µCi of $^{64}Cu$-CBP(n), 0.1 mL and 20-50 µCi of $^{68}Ga$-CBP(n) and 0.1 mL and 10-20 µCi of $Al^{18}F$-CBP(n) in a 18 mM solution of sucrose in water, followed by saline flush. Each animal was imaged with PET/CT and euthanized 2 hours post injection. The lungs, blood, urine, heart, liver, left rectus femoris muscle, spleen, small intestine, kidneys, left femur bone were collected from all animals. The tissues were weighed, and radioactivity in each tissue was measured on a gamma counter (CobraII Auto gamma; Packard). The radioactivity in the lung was reported as percent injected dose per gram corrected with the average sham weight, which was calculated by dividing the counts of $^{64}$Cu per average sham tissue weight in gram by the total of counts of the injected dose. The radioactivity in every other tissue was reported as percent injected dose per gram (% ID/g), which was calculated by dividing the counts of $^{64}$Cu per gram of tissue by the total of counts of the injected dose. A p-value of less than 0.05 was considered significant. Uncertainties are expressed as the standard error of the mean.

Pharmacokinetics and Metabolic Stability

The pharmacokinetics and metabolic stability of the probes were evaluated in Adult male Wistar rats. The right femoral vein was cannulated for intravenous delivery of the PET agent and the right femoral artery was cannulated for blood sampling. Each animal was injected with approximately 50-70 µCi of $^{64}$Cu-CBP(n) diluted in 0.2-0.3 mL with an 18 mM solution of sucrose in water, followed by saline flush. After probe injection, several blood draws were collected at 0, 2, 5, 10, 15, 30, 60 and 120 minutes post injection into ethylenediaminetetraacetic acid (EDTA) blood tubes. Blood was weighed, and radioactivity in the blood was measured on a gamma counter to assess clearance of total $^{64}$Cu. The serum was isolated by centrifugation of the blood (10 minutes, 4950 rpm) and proteins were precipitated with a mixture of cold methanol/acetonitrile (1/1). Solids were removed by centrifugation and the supernatant was injected onto an analytic HPLC column. The eluent was collected every 30 seconds, and the activity of each fraction was measured using a gamma counter. The result was compared with standards of pure probe and probe immediately isolated from plasma (t=0 sample).

MicroPET Imaging Studies

Instrument calibration was performed with phantoms containing small known amount of radioactivity. Isotropic (0.3 mm) CT images were acquired over 6 minutes with 512 projections with 3 frames per projection (exposure time per frame, ~200 msec; peak tube voltage, 70 kV; tube current, 177 mA). PET and CT images were reconstructed using the LabPET software (TriFoil Imaging) and the CT data were used to provide attenuation correction for the PET reconstructions. The PET data were reconstructed using a maximum-likelihood expectation-maximization (MLEM) algorithm run over 30 iterations to a voxel size of 0.5×0.5×0.6 mm$^3$. For the pharmacokinetic analyses, the PET data were reconstructed in 1 minute (first 10 frames), 3 minutes (next 10 frames), and 10 minutes (last 8-10 frames) intervals out to 120 minutes post injection.

Tissue Analysis

The right lung was inflated and fixed with 10% formalin, embedded in paraffin, cut into 5-µm-thick sections and stained with Hematoxylin and Eosin, Trichrome, and Sirius red with a counterstain of Fast Green. The left lung was digested with 6 M HCl for hydroxyproline (Hyp) analysis. Hydroxyproline is a surrogate for collagen content. Hydroxyproline in tissue was quantified by HPLC analysis after a two-step derivatization process of samples. (Hutson, P. R., Crawford, M. E., Sorkness, R. L. *Journal of Chromatography B*, 2003, 791(1), 427-430). Hydroxyproline is expressed as amount per organ.

Example 15

Evaluation of $^{64}$Cu-CBP1 in the Standard BM Model of Pulmonary Fibrosis.

$^{64}$Cu-CBP1 was administered intravenously to mice 14 days after bleomycin or sham treatment. After 2.5 hours, the mice were euthanized and the organs harvested, weighed, and assayed for radioactivity in a gamma counter. $^{64}$Cu-CBP1 showed greater lung uptake in BM-treated mice (fibrotic) compared to controls Apart from the lungs, the probe showed a similar non-target uptake in control and BM-treated animals. The probe was excreted mainly through the kidneys.

TABLE 2

Biodistribution Data in % ID/g for CBP1 in sham and in bleomycin mice at 120 post probe injection. Uncertainty is represented as standard error of mean.

| | SHAM | | BM | |
|---|---|---|---|---|
| | % ID/g | N | % ID/g | N |
| blood | 0.100 ± 0.020 | 2 | 0.093 ± 0.019 | 3 |
| lungs | 0.433 ± 0.112 | 2 | 0.839 ± 0.138 | 3 |
| heart | 0.080 ± 0.010 | 2 | 0.073 ± 0.003 | 3 |
| liver | 0.715 ± 0.005 | 2 | 0.777 ± 0.124 | 3 |
| muscle | 0.060 ± 0.010 | 2 | 0.150 ± 0.059 | 3 |
| spleen | 0.145 ± 0.005 | 2 | 0.133 ± 0.009 | 3 |
| sm. intestine | 0.420 ± 0.120 | 2 | 0.330 ± 0.064 | 3 |
| kidney | 13.445 ± 1.825 | 2 | 13.417 ± 1.725 | 3 |
| bone | 0.115 ± 0.045 | 2 | 0.283 ± 0.172 | 3 |

Example 16

Evaluation of $^{64}$Cu-CBP3 in the Standard BM Model of Pulmonary Fibrosis.

$^{64}$Cu-CBP3 was administered intravenously to mice 14 days after bleomycin or sham treatment. After 2.5 hours, the mice were euthanized and the organs harvested, weighed, and assayed for radioactivity in a gamma counter. $^{64}$Cu-CBP3 showed greater lung uptake in BM-treated mice (fibrotic) compared to controls (Table 3), and this difference was statistically significant P<0.0001. Apart from the lungs, the probe showed a similar non-target uptake in sham and BM-treated animals. The probe was excreted mainly through the kidneys.

TABLE 3

Biodistribution Data in % ID/g for CBP3 in sham and in bleomycin mice at 120 post probe injection. Uncertainty is represented as standard error of mean.

| | SHAM | | BM | |
|---|---|---|---|---|
| | % ID/g | N | % ID/g | N |
| blood | 0.167 ± 0.015 | 4 | 0.490 ± 0.312 | 6 |
| lungs | 0.359 ± 0.006 | 4 | 1.479 ± 0.262 | 6 |
| heart | 0.103 ± 0.005 | 4 | 0.163 ± 0.038 | 6 |
| liver | 2.014 ± 0.074 | 4 | 2.567 ± 0.236 | 6 |
| muscle | 0.050 ± 0.004 | 4 | 0.135 ± 0.045 | 6 |

TABLE 3-continued

Biodistribution Data in % ID/g for CBP3 in sham and in bleomycin mice at 120 post probe injection. Uncertainty is represented as standard error of mean.

|  | SHAM | | BM | |
|---|---|---|---|---|
|  | % ID/g | N | % ID/g | N |
| spleen | 0.210 ± 0.020 | 4 | 0.975 ± 0.242 | 6 |
| sm. intestine | 0.692 ± 0.085 | 4 | 1.042 ± 0.346 | 6 |
| kidney | 13.021 ± 0.494 | 4 | 14.593 ± 1.559 | 6 |
| bone | 0.128 ± 0.009 | 4 | 0.292 ± 0.125 | 6 |

Example 17

Evaluation of $^{64}$Cu-CBP5 in the Standard BM Model of Pulmonary fibrosis.

$^{64}$Cu-CBP5 was administered intravenously to mice 14 days after bleomycin or sham treatment. After 2.5 hours, the mice were euthanized and the organs harvested, weighed, and assayed for radioactivity in a gamma counter. $^{64}$Cu-CBP5 showed greater lung uptake in BM-treated mice (fibrotic) compared to controls Apart from the lungs, the probe showed a similar non-target uptake in control and BM-treated animals. The probe was excreted mainly through the kidneys.

TABLE 4

Biodistribution Data in % ID/g for CBP5 in sham and in bleomycin mice at 120 post probe injection. Uncertainty is represented as standard error of mean.

|  | SHAM | | BM | |
|---|---|---|---|---|
|  | % ID/g | N | % ID/g | N |
| blood | 0.110 ± 0.018 | 4 | 0.121 ± 0.028 | 6 |
| lungs | 0.318 ± 0.135 | 4 | 0.623 ± 0.320 | 6 |
| heart | 0.075 ± 0.009 | 4 | 0.094 ± 0.013 | 6 |
| liver | 2.630 ± 0.146 | 4 | 3.836 ± 0.770 | 6 |
| muscle | 0.473 ± 0.406 | 4 | 0.030 ± 0.005 | 6 |
| spleen | 0.815 ± 0.420 | 4 | 1.588 ± 0.546 | 6 |
| sm. intestine | 0.513 ± 0.100 | 4 | 0.431 ± 0.089 | 6 |
| kidney | 30.488 ± 2.008 | 4 | 18.368 ± 1.909 | 6 |
| bone | 0.703 ± 0.343 | 4 | 0.490 ± 0.237 | 6 |

Example 18

Evaluation of $^{64}$Cu-CBP6 in the Standard BM Model of Pulmonary Fibrosis.

$^{64}$Cu-CBP6 was administered intravenously to mice 14 days after bleomycin or sham treatment. After 2.5 hours, the mice were euthanized and the organs harvested, weighed, and assayed for radioactivity in a gamma counter. $^{64}$Cu-CBP6 showed greater lung uptake in BM-treated mice (fibrotic) compared to controls Apart from the lungs, the probe showed a similar non-target uptake in control and BM-treated animals. The probe was excreted mainly through the kidneys.

TABLE 5

Biodistribution Data in % ID/g for CBP6 in sham and in bleomycin mice at 120 post probe injection. Uncertainty is represented as standard error of mean.

|  | SHAM | | BM | |
|---|---|---|---|---|
|  | % ID/g | N | % ID/g | N |
| blood | 0.147 ± 0.010 | 2 | 0.279 ± 0.096 | 6 |
| lungs | 0.013 ± 0.002 | 2 | 0.019 ± 0.003 | 6 |
| heart | 0.121 ± 0.017 | 2 | 0.156 ± 0.016 | 6 |
| liver | 2.643 ± 0.144 | 2 | 2.503 ± 0.218 | 6 |
| muscle | 0.303 ± 0.243 | 2 | 0.137 ± 0.069 | 6 |
| spleen | 0.669 ± 0.030 | 2 | 0.775 ± 0.084 | 6 |
| sm. intestine | 0.747 ± 0.168 | 2 | 0.938 ± 0.164 | 6 |
| kidney | 13.366 ± 1.225 | 2 | 14.008 ± 0.727 | 6 |
| bone | 0.150 ± 0.020 | 2 | 0.366 ± 0.049 | 6 |

Example 19

Evaluation of $^{64}$Cu-CBP3 in the Standard BM Model of Pulmonary Fibrosis.

$^{64}$Cu-CBP7 was administered intravenously to mice 14 days after bleomycin or sham treatment. After 2.5 hours, the mice were euthanized and the organs harvested, weighed, and assayed for radioactivity in a gamma counter. $^{64}$Cu-CBP7 showed 8-fold greater lung uptake in BM-treated mice (fibrotic) compared to controls (Table 3), and this difference was statistically significant P<0.001. Apart from the lungs, the probe showed a similar non-target uptake in sham and BM-treated animals. The probe was excreted mainly through the kidneys.

TABLE 6

Biodistribution Data in % ID/g for CBP7 in sham and in bleomycin mice at 120 post probe injection. Uncertainty is represented as standard error of mean.

|  | SHAM | | BM | |
|---|---|---|---|---|
|  | % ID/g | N | % ID/g | N |
| blood | 0.275 ± 0.034 | 6 | 0.624 ± 0.062 | 7 |
| lungs | 0.477 ± 0.094 | 6 | 3.641 ± 0.724 | 7 |
| heart | 0.188 ± 0.026 | 6 | 0.413 ± 0.072 | 7 |
| liver | 2.093 ± 0.583 | 6 | 2.824 ± 0.744 | 7 |
| muscle | 0.097 ± 0.018 | 6 | 0.179 ± 0.033 | 7 |
| spleen | 0.985 ± 0.282 | 6 | 1.937 ± 0.612 | 7 |
| sm. intestine | 0.853 ± 0.246 | 6 | 0.877 ± 0.077 | 7 |
| kidney | 67.763 ± 4.944 | 6 | 56.891 ± 6.402 | 7 |
| bone | 0.212 ± 0.022 | 6 | 0.456 ± 0.049 | 7 |

Example 20

Comparison of $^{64}$Cu-CBP(n) Biodistribution in the Standard BM Model of Pulmonary Fibrosis.

Table 7 summarizes the uptake of 5 $^{64}$Cu-CBP(n) probes in the standard bleomycin model, 14 days after bleomycin or sham treatment. The data are presented as % injected dose per lung. The order of efficacy, as assessed by comparing the ratio of lung uptake in the BM-treated animals to lung uptake in sham animals was $^{64}$Cu-CBP7>$^{64}$Cu-CBP3>$^{64}$Cu-CBP6>$^{64}$Cu-CBP5~$^{64}$Cu-CBP1. $^{64}$Cu-CBP7 also had the highest uptake in the lungs of BM-treated animals overall and this was significantly higher than the other probes, P<0.05.

TABLE 7

Biodistribution Data in % ID/lung for CBP1, CBP3, CBP5, CBP6 and CBP7 in sham and in bleomycin mice at 120 post probe injection. Uncertainty is represented as standard error of mean.

|      | SHAM          |   | BM            |   |
|------|---------------|---|---------------|---|
|      | % ID/lung     | N | % ID/lung     | N |
| CBP1 | 0.032 ± 0.008 | 2 | 0.061 ± 0.010 | 3 |
| CBP3 | 0.013 ± 0.001 | 4 | 0.052 ± 0.009 | 6 |
| CBP5 | 0.016 ± 0.007 | 4 | 0.032 ± 0.016 | 6 |
| CBP6 | 0.015 ± 0.001 | 2 | 0.041 ± 0.009 | 6 |
| CBP7 | 0.016 ± 0.003 | 6 | 0.123 ± 0.026 | 7 |

Example 21

Comparison of $^{64}$Cu-CBP7 Lung Uptake in BM-Treated and Sham Mice as Assessed by PET Imaging.

Mean PET lung activity values for CBP7, in sham and BM-treated mice from data 50-80 minutes after injection are shown in Table 8 for the two groups of mice. Mean PET lung activity in heart and muscle was not significantly different between groups. There was a 3-fold higher uptake in the mean PET lung activity in the bleomycin-treated group compared to sham-treated mice for CBP7 (P<0.001).

TABLE 8

Mean PET lung activity values for CBP7 in sham and BM-treated mice from data 50-80 min after injection.

|        | SHAM (N = 7)   | BM (N = 5)    |
|        | % ID/cc        | % ID/cc       |
|--------|----------------|---------------|
| lung   | 3.078 ± 0.198  | 7.716 ± 1.050 |
| heart  | 0.711 ± 0.033  | 1.126 ± 0.108 |
| muscle | 0.377 ± 0.025  | 0.502 ± 0.056 |

Example 22

Comparison of $^{64}$Cu-CBP(n) Blood Plasma Pharmacokinetics and Metabolic Stability in Wistar Rats.

The pharmacokinetics and metabolic stability of the probes were evaluated in adult male Wistar rats by sampling blood at various intervals for 2 h post injection. By measuring the total radioactivity in blood at different time points, it was observed that the copper-64 blood clearance profile was very similar for all five probes. There was a rapid clearance of activity from the blood in the first 20 min, which then slowed over the next 90 min. The elimination blood half-lives were calculated from a biexponential fit to the clearance data and ranged from 18 to 23 min. Radio-HPLC analyses of rat serum at different time points post-injection was performed and these HPLC traces were compared to pure probe spiked into serum (t=0 sample), see Table 9. The metabolism was extremely rapid for CBP1, CBP3 and CBP5, less than 50% of intact probe was detected in the blood 15 min post injection. CBP6 was still largely intact at 15 min post probe injection (percentage of intact probe >80) and was then metabolized in the next 45 min. CBP7 was completely intact in the serum at 60 min post injection and in indeed highly stable over time: more than 80% of the circulating activity is intact probe at 120 min post probe injection.

CBP7 with three NODAGA chelators is more metabolically stable than the other CBP(n) probes with a single NODAGA chelator. This higher metabolic stability correlates positively with the greater efficacy of CBP7 in detecting fibrotic lung tissue, e.g. Table 7.

TABLE 9

Metabolic stability of CBP1, CBP3, CBP5, CBP6, CBP7 in rats estimated from HPLC analysis of blood samples.

| Time pi (min) | CBP1 | CBP3 | CBP5 | CBP6 | CBP7 |
|               |      | % Intact probe |      |      |      |
|---------------|------|------|------|------|------|
| 15            | 49   | 37   | 10   | 75   | 99   |
| 60            | 7    | 5    | 0    | 25   | >95  |

Example 23

$^{68}$Ga-CBP8 Detection and Quantification of Pulmonary Fibrosis in the Standard BM Model.

The probe $^{68}$Ga-CBP8 was administrated intravenously to mice 14 days after bleomycin or sham treatment. Mice were imaged 50-80 min post injection. After 2.5 hours, the mice were euthanized and the organs harvested, weighed, and assayed for radioactivity in a gamma counter. From PET data analysis, activity in the lungs was compared between the 2 groups of animals using a two-sided t-test. Mean PET lung activity values for CBP8, in sham and BM-treated mice from data 50-80 minutes after injection are shown in Table 10 for the two groups of mice. Mean PET lung activity in heart and muscle was not significantly different between groups. There was a 3-fold higher uptake in the mean PET lung activity in the bleomycin-treated group compared to controls for CBP8 (P<0.05). Biodistribution data were compared between the 2 groups of animals using a two-sided t-test. The biodistribution data is shown in Table 11 for the two groups of mice. Organ uptake was not significantly different between groups, except for the lungs were there was a 6-fold higher uptake in the bleomycin-treated group (P<0.001). The lung uptake of CBP8 was found to correlate linearly (Pearson coefficient $R^2$=0.84) with the amount of hydroxyproline in the lung. Hydroxyproline is a measure of total collagen and a marker of fibrosis.

TABLE 10

Mean PET lung activity values for CBP8 in sham and BM-treated mice from data 50-80 min after injection.

|        | SHAM (N = 4)  | BM (N = 5)     |
|        | % ID/cc       | % ID/cc        |
|--------|---------------|----------------|
| lung   | 3.874 ± 0.344 | 9.752 ± 2.090  |
| heart  | 0.947 ± 0.078 | 1.869 ± 0.359  |
| muscle | 0.481 ± 0.050 | 0.842 ± 0.167  |

TABLE 11

Biodistribution in % ID/g of CBP8 in sham and BM-treated animals, 2.5 hour post CBP8 injection. Uncertainty is represented as standard error of mean.

|             | SHAM (N = 6)  | BM (N = 10)   |
|             | % ID/g        | % ID/g        |
|-------------|---------------|---------------|
| blood       | 0.512 ± 0.181 | 0.569 ± 0.102 |
| lung        | 0.470 ± 0.091 | 2.265 ± 0.265 |
| heart       | 0.242 ± 0.059 | 0.340 ± 0.032 |
| liver       | 0.950 ± 0.127 | 1.189 ± 0.113 |
| muscle      | 0.567 ± 0.247 | 0.927 ± 0.422 |
| spleen      | 0.462 ± 0.047 | 0.659 ± 0.141 |
| sm. intest  | 0.420 ± 0.086 | 0.830 ± 0.197 |

TABLE 11-continued

Biodistribution in % ID/g of CBP8 in sham and BM-treated animals, 2.5 hour post CBP8 injection. Uncertainty is represented as standard error of mean.

|  | SHAM (N = 6)<br>% ID/g | BM (N = 10)<br>% ID/g |
| --- | --- | --- |
| kidney | 30.033 ± 4.591 | 41.063 ± 5.830 |
| bone | 1.108 ± 0.594 | 1.117 ± 0.347 |

Example 24

$^{68}$Ga-CBP8 Detection and Quantification of Pulmonary Fibrosis in the Low Dose BM+Vascular Leak Mouse Model of Pulmonary Fibrosis.

Three different cohorts of mice were studied: (FTY720+ low dose bleomycin (FTY+LD group, causes pulmonary fibrosis)-, low dose bleomycin (LD, no pulmonary fibrosis)- and FTY720 (no pulmonary fibrosis)-treated mice. $^{68}$Ga-CBP8 was administrated intravenously to mice 14 days after bleomycin or sham treatment. FTY720 was administered intraperitoneally to the mice at 1 mg/kg three times a week. 2.5 hour after CBP8 injection, the mice were euthanized and the organs harvested, weighed, and assayed for radioactivity in a gamma counter. Biodistribution data were compared between the 3 groups of animals using ANOVA, followed by Bonferroni post hoc test. The biodistribution data is shown in Table 12 for the three groups of mice. Organ uptake was not significantly different between groups, except for the lungs were there was a 5-fold higher uptake in the (FTY+LD)-treated group compared to the FTY-treated group (P<0.01) and a 3-fold higher uptake in the (FTY+LD)-treated group compared to the (LD)-treated group (P<0.05). The difference in lung uptake between the (LD)- and the FTY-treated groups was not statistically significant. The lung uptake of $^{68}$Ga-CBP8 was found to correlate linearly (Pearson coefficient $R^2$=0.87) with the amount of hydroxyproline in the lung. This data demonstrates that $^{68}$Ga-CBP8 can detect pulmonary fibrosis in a second animal model of disease and that $^{68}$Ga-CBP8 uptake correlates with extent of disease as assessed by hydroxyproline measurements.

TABLE 12

Biodistribution in % ID/g of $^{68}$Ga-CBP8 in FTY-, (LD BM)- and (FTY + LD)-treated mice 2.5 hour post $^{68}$Ga-CBP8 injection. Uncertainty is represented as standard error of mean.

|  | FTY (N = 3)<br>% ID/g | LD (N = 4)<br>% ID/g | FTY + LD (N = 14)<br>% ID/g |
| --- | --- | --- | --- |
| blood | 0.347 ± 0.017 | 0.523 ± 0.062 | 0.472 ± 0.066 |
| lungs | 0.407 ± 0.077 | 0.568 ± 0.097 | 1.173 ± 0.130 |
| heart | 0.293 ± 0.024 | 0.340 ± 0.038 | 0.333 ± 0.049 |
| liver | 1.437 ± 0.108 | 1.998 ± 0.117 | 1.227 ± 0.154 |
| muscle | 0.107 ± 0.007 | 0.263 ± 0.097 | 0.327 ± 0.111 |
| spleen | 0.470 ± 0.045 | 0.925 ± 0.126 | 0.631 ± 0.109 |
| small intest. | 0.477 ± 0.052 | 0.690 ± 0.064 | 0.757 ± 0.127 |
| kidney | 42.67 ± 1.418 | 50.36 ± 2.756 | 41.76 ± 2.148 |
| bone | 0.290 ± 0.012 | 0.840 ± 0.392 | 0.464 ± 0.067 |

Example 25

$^{68}$Ga-CBP8-PET can Monitor Treatment Response in Pulmonary Fibrosis.

$^{68}$Ga-CBP8 was administered to three cohorts of mice followed by PET imaging and then biodistribution. Cohort 1 received FTY720+low dose bleomycin+therapeutic anti-alphaV-beta6 antibody 3G9 (therapeutic treatment cohort) and denoted as (FTY+LD+3G9). Cohort 2 received FTY720+low dose bleomycin+irrelevant anti-1E6 (control treatment cohort) and denoted as (FTY+LD+1E6). Cohort 3 had no lung injury and just received the 3G9 antibody and denoted (3G9). $^{68}$Ga-CBP8 was administered intravenously to mice 14 days after bleomycin or sham treatment. FTY720 was administered intraperitoneally to the mice at 1 mg/kg three times a week. 3G9 (alpha-v-beta-6 blocking antibody) and 1E6 (control antibody) were injected into the mice intraperitoneally three times week at a concentration of 1 mg/kg. 2.5 hour after injection of CBP8, the mice were euthanized and the organs harvested, weighed, and assayed for radioactivity in a gamma counter. Biodistribution data were compared between the 3 groups of animals using ANOVA, followed by Bonferroni post hoc test. Organ uptake, quantification of PET data and hydroxyproline level are shown in Table 13 for the three groups of mice. Organ uptake was not significantly different between groups, except for the lungs were there was a 3-fold higher uptake in the (FTY+LD+1E6)-treated group compared to the (FTY+LD+3G9)-treated group (P<0.01) and a 6-fold higher uptake in the (FTY+LD+1E6)-treated group compared to the (3G9)-treated group (P<0.01). The lung uptake was not statistically different between the (FTY+LD+3G9)-treated group and the (3G9)-treated group. PET imaging data showed the same result as the biodistribution data where the highest lung signal was in the (FTY+LD+1E6)-treated group (lung injury with no treatment). Treatment of the lung injury group with 3G9 (FTY+LD+3G9) resulted in less probe uptake indicating that $^{68}$Ga-CBP8 could monitor treatment response. The effect of treatment is shown in the lung hydroxyproline values for the three cohorts (Table 13) and these hydroxyproline values also correlate with the $^{68}$Ga-CBP8 PET imaging and biodistribution. The lung uptake of $^{68}$Ga-CBP8 was found to correlate linearly (Pearson coefficient $R^2$=0.79) with the amount of hydroxyproline in the lung.

TABLE 13

Biodistribution in % ID/lung at 2.5 hour post CBP8 injection of 3 cohorts (3G9-, FTY + LD + 3G9-, and, FTY + LD + 1E6-treated animals), mean lung PET activity values CBP8 in the 3 cohorts from data 50-110 min after injection and hydroxyproline content in the left lung of the 3 cohorts. Uncertainty is represented as standard error of mean.

|  | N | % ID/lung | % ID/cc | Hydroxyproline (µg/lung) |
| --- | --- | --- | --- | --- |
| 3G9 | 3 | 0.043 ± 0.001 | 2.07 ± 0.53 | 72.69 ± 1.31 |
| FTY + LD + 3G9 | 7 | 0.061 ± 0.006 | 3.31 ± 0.32 | 80.84 ± 2.94 |
| FTY + LD + 1E6 | 5 | 0.082 ± 0.006 | 5.63 ± 0.46 | 104.80 ± 6.16 |

Example 26

Evaluation of Al$^{18}$F-CBP9 in the Standard Bleomycin Mouse Model of Pulmonary Fibrosis.

Biodistribution of Al$^{18}$F-CBP9 in bleomycin-treated mice and sham-treated mice. Al$^{18}$F-CBP9 was administered intravenously to mice 14 days after bleomycin or sham treatment. After 2.5 hours, the mice were euthanized and the organs harvested, weighed, and assayed for radioactivity in a gamma counter. Biodistribution data were compared between the 2 groups of animals using a two-sided t-test. The biodistribution data is shown in Table 14 for the two groups of mice. Organ uptake was not significantly different between groups, including in the lungs.

TABLE 14

Biodistribution Data in % ID/g for CBP9 in sham and in bleomycin mice at 120 post probe injection. Uncertainty is represented as standard error of mean.

|  | SHAM | | BM | |
| --- | --- | --- | --- | --- |
|  | % ID/g | N | % ID/g | N |
| blood | 0.543 ± 0.106 | 2 | 0.511 ± 0.025 | 2 |
| lungs | 0.625 ± 0.155 | 2 | 2.120 ± 0.230 | 2 |
| heart | 0.466 ± 0.119 | 2 | 0.352 ± 0.001 | 2 |
| liver | 1.262 ± 0.005 | 2 | 9.193 ± 1.276 | 2 |
| muscle | 0.238 ± 0.049 | 2 | 0.179 ± 0.019 | 2 |
| spleen | 0.552 ± 0.041 | 2 | 13.232 ± 0.352 | 2 |
| sm. intestine | 0.706 ± 0.050 | 2 | 0.570 ± 0.078 | 2 |
| kidney | 23.369 ± 2.056 | 2 | 29.664 ± 2.274 | 2 |
| bone | 8.155 ± 0.136 | 2 | 9.653 ± 0.357 | 2 |

Example 27

Evaluation of Al$^{18}$F-CBP10 in the Standard Bleomycin Mouse Model of Pulmonary Fibrosis.

Biodistribution of Al$^{18}$F-CBP10 in bleomycin-treated mice and sham-treated mice. Al$^{18}$F-CBP0 was administered intravenously to mice 14 days after bleomycin or sham treatment. After 2.5 hours, the mice were euthanized and the organs harvested, weighed, and assayed for radioactivity in a gamma counter. Biodistribution data were compared between the 2 groups of animals using a two-sided t-test. The biodistribution data is shown in Table 15 for the two groups of mice. Organ uptake was not significantly different between groups, including in the lungs.

TABLE 15

Biodistribution in % ID/g of CBP10 in sham and BM-treated animals, 2.5 hour post CBP10 injection. Uncertainty is represented as standard error of mean.

|  | SHAM (N = 4) | BM (N = 4) |
| --- | --- | --- |
|  | % ID/g | % ID/g |
| blood | 0.405 ± 0.075 | 1.294 ± 0.668 |
| lungs | 4.263 ± 0.572 | 12.905 ± 3.113 |
| heart | 0.280 ± 0.031 | 1.146 ± 0.367 |
| liver | 14.040 ± 1.000 | 27.231 ± 0.995 |
| muscle | 0.145 ± 0.024 | 0.345 ± 0.141 |
| spleen | 11.160 ± 2.356 | 39.951 ± 17.550 |
| sm. intest. | 1.123 ± 0.480 | 1.492 ± 0.542 |
| kidney | 26.243 ± 4.853 | 44.170 ± 16.811 |
| bone | 2.533 ± 0.735 | 2.963 ± 0.716 |

Example 28

$^{64}$Cu-CBP7 is Specific for Pulmonary Fibrosis: Comparison with Non-Binding Isomer $^{64}$Cu-CBP11 in the Standard Bleomycin Mouse Model of Pulmonary Fibrosis.

The replacement of one L-cysteine amino acid in CBP7 with a D-cysteine to give CBP11 results in loss of collagen affinity by the D-Cys peptide (Caravan, P., Das, B., Dumas, S., Epstein, F. H., Helm, P. A., Jacques, V., Koerner, S., Kolodziej, A., Shen, L., Sun, W., Zhang, Z., *Angewandte Chemie*, 2007, 119(43), 8319-8321.) Biodistribution of $^{64}$Cu-CBP11 was assessed in bleomycin-treated mice and sham-treated mice. $^{64}$Cu-CBP11 was administered intravenously to mice 14 days after bleomycin or sham treatment. After 2.5 hours, the mice were euthanized and the organs harvested, weighed, and assayed for radioactivity in a gamma counter. Mean PET activity in lung, heart and muscle was not significantly different between groups (Table 16). Biodistribution data were compared between the 2 groups of animals using a two-sided t-test. The biodistribution data is shown in Table 17 for the two groups of mice. Organ uptake was not significantly different between groups, including in the lungs. This data is in contrast to the data collected with $^{64}$Cu-CBP7 where there was significantly higher probe uptake in fibrotic lungs measured either by biodistribution (Table 6) or PET imaging (Table 8). Taken together, the data indicate that $^{64}$Cu-CBP7 is specific for pulmonary fibrosis.

TABLE 16

Mean PET lung activity values for CBP11 in sham and BM-treated mice from data 50-80 min after injection.

|  | SHAM (N = 4) | BM (N = 5) |
| --- | --- | --- |
|  | % ID/cc | % ID/cc |
| lung | 1.011 ± 0.103 | 1.091 ± 0.040 |
| heart | 0.212 ± 0.020 | 0.224 ± 0.015 |
| muscle | 0.094 ± 0.009 | 0.123 ± 0.015 |

TABLE 17

Biodistribution in % ID/g of CBP11 in sham and BM-treated animals, 2.5 hours post CBP10 injection. Uncertainty is represented as standard error of mean.

|  | SHAM (N = 4) | BM (N = 4) |
| --- | --- | --- |
|  | % ID/g | % ID/g |
| blood | 0.210 ± 0.017 | 0.373 ± 0.180 |
| lungs | 0.665 ± 0.336 | 0.572 ± 0.091 |
| heart | 0.143 ± 0.008 | 0.170 ± 0.044 |
| liver | 1.303 ± 0.086 | 0.953 ± 0.069 |
| muscle | 0.178 ± 0.101 | 0.105 ± 0.027 |
| spleen | 0.408 ± 0.015 | 0.475 ± 0.063 |
| sm. intestine | 0.578 ± 0.057 | 0.925 ± 0.178 |
| kidney | 57.683 ± 4.197 | 51.728 ± 4.203 |
| bone | 0.288 ± 0.138 | 0.223 ± 0.060 |

Example 29

$^{68}$Ga-CBP8 is Specific for Pulmonary Fibrosis: Comparison with Non-Binding Isomer $^{68}$Ga-CBP12 in the Standard Bleomycin Mouse Model of Pulmonary Fibrosis.

The replacement of one L-cysteine amino acid in CBP8 with a D-cysteine to give CBP12 results in loss of collagen affinity by the D-Cys peptide (Caravan, P., Das, B., Dumas, S., Epstein, F. H., Helm, P. A., Jacques, V., Koerner, S., Kolodziej, A., Shen, L., Sun, W., Zhang, Z., *Angewandte Chemie*, 2007, 119(43), 8319-8321.) $^{68}$Ga-CBP12 was administered intravenously to mice 14 days after bleomycin or sham treatment. After 2.5 hours, the mice were euthanized and the organs harvested, weighed, and assayed for radioactivity in a gamma counter. Mean PET lung activity values for CBP12, in sham and BM-treated mice from data 50-80 minutes after injection are shown in Table 218 for the two groups of mice. Mean PET lung activity in lung, heart and muscle was not significantly different between groups. Biodistribution data were compared between the 2 groups of animals using a two-sided t-test. The biodistribution data is shown in Table 19 for the two groups of mice. Organ uptake was not significantly different between groups, including in the lungs. This data is in contrast to the data collected with $^{68}$Cu-CBP8 where there was significantly higher probe uptake in fibrotic lungs measured either by biodistribution (Table 11) or PET imaging (Table 10). Taken together, the data indicate that $^{68}$Cu-CBP8 is specific for pulmonary fibrosis.

TABLE 18

Mean PET lung activity values for CBP12 in sham and BM-treated mice from data 50-80 min after injection.

|  | SHAM (N = 4) % ID/cc | BM (N = 4) % ID/cc |
|---|---|---|
| lung | 3.465 ± 0.288 | 3.718 ± 0.648 |
| heart | 0.715 ± 0.140 | 0.711 ± 0.097 |
| muscle | 0.324 ± 0.066 | 0.308 ± 0.062 |

TABLE 19

Biodistribution Data in % ID/g for CBP12 in sham and in bleomycin mice at 150 post probe injection. Uncertainty is represented as standard error of mean.

|  | SHAM % ID/g | BM % ID/g |
|---|---|---|
| blood | 0.225 ± 0.021 | 0.343 ± 0.086 |
| lungs | 0.240 ± 0.004 | 0.555 ± 0.152 |
| heart | 0.140 ± 0.010 | 0.140 ± 0.014 |
| liver | 1.035 ± 0.159 | 1.183 ± 0.078 |
| muscle | 0.503 ± 0.274 | 0.378 ± 0.288 |
| spleen | 0.710 ± 0.291 | 0.573 ± 0.177 |

TABLE 19-continued

Biodistribution Data in % ID/g for CBP12 in sham and in bleomycin mice at 150 post probe injection. Uncertainty is represented as standard error of mean.

|  | SHAM % ID/g | BM % ID/g |
|---|---|---|
| sm. intestine | 0.455 ± 0.127 | 0.873 ± 0.171 |
| kidney | 29.580 ± 4.621 | 28.245 ± 2.942 |
| bone | 0.345 ± 0.077 | 0.625 ± 0.455 |

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the embodiments contained herein.

REFERENCES

[1] S. G. Levy, V. Jacques, K. L. Zhou, S. Kalogeropoulos, K. Schumacher, J. C. Amedio, J. E. Scherer, S. R. Witowski, R. Lombardy and K. Koppetsch, *Org. Process Res. Dev.* 2009, 13, 535-542.

[2] B. S. Shea, S. F. Brooks, B. A. Fontaine, J. Chun, A. D. Luster and A. M. Tager, *Am J Respir Cell Mol Biol* 2010, 43, 662-673.

[3] A. M. Loening and S. S. Gambhir, Mol. Imaging 2003, 2, 131-137.

[4] Zhang Z, Kolodziej A F, Qi J, Nair S A, Wang X, Case A W, Greenfield M T, Graham P B, McMurry T J, Caravan P., "Effect of Peptide-Chelate Architecture on Metabolic Stability of Peptide-based MRI Imaging reporters", *New journal of chemistry.* 2010, 34, 611-616.

The citation of any document or reference is not to be construed as an admission that it is prior art with respect to the present invention.

What is claimed is:

1. A cyclic polypeptide of formula (I):

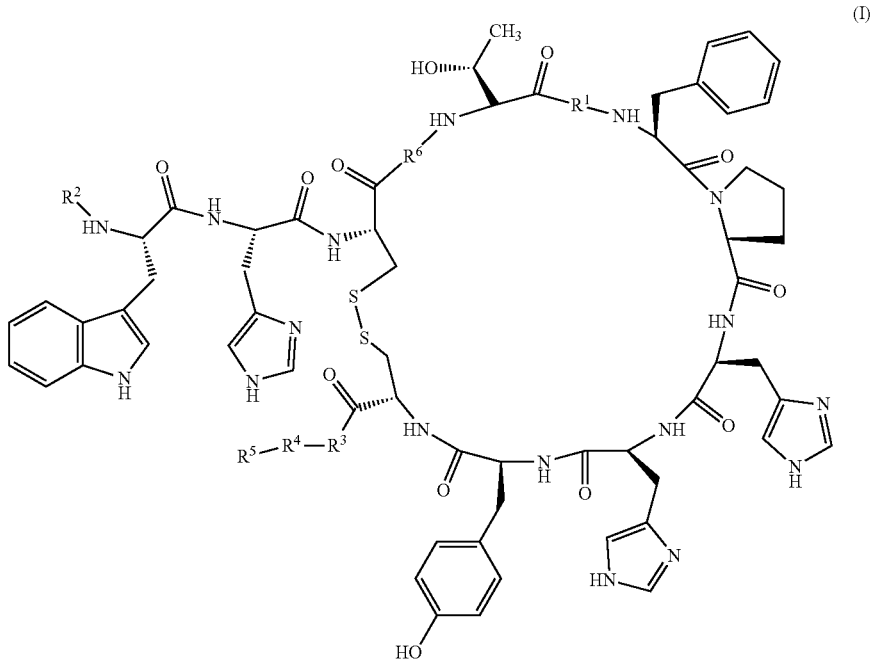

wherein $R^1$ is selected from the group consisting of lysine (K), tyrosine (Y), glutamic acid (E), aspartic acid (D), arginine (R) and leucine (L);

wherein $R^2$ is selected from the group consisting of -glycine (G)-tryptophan (W) and -glycine (G)-lysine (K)[glycine (G)];

wherein $R^3$ is selected from the group consisting of leucine (L) and phenylalanine (F);

wherein $R^4$ is selected from the group consisting of tyrosine (Y) and 2-Nal (2-naphthylalanine);

wherein $R^5$ is selected from the group consisting of glycine (G) and BIP (L-4,4'-biphenylalanine);

wherein $R^6$ is selected from the group consisting of threonine (T) and tyrosine (Y); and wherein the cyclic polypeptide further comprises a linker that is capable of linking an imaging reporter; or a cyclic polypeptide of formula (I):

wherein:

$R^1$ is lysine (K)-NODAGA, $R^2$ is NODAGA-glycine (G)-lysine (K)[glycine (G)-NODAGA], $R^3$ is leucine (L), $R^4$ is tyrosine (Y), $R^5$ is 4,4-biphenylalanine (BIP), and $R^6$ is threonine (T), and wherein the cyclic polypeptide comprises an imaging reporter; or a cyclic peptide of formula (I):

wherein:

$R^1$ is tyrosine (Y), $R^2$ is NODAGA-glycine (G)-glutamine(Q), $R^3$ is leucine (L), $R^4$ is tyrosine (Y), $R^5$ is glycine (G), and $R^6$ is threonine (T), and wherein the cyclic polypeptide comprises an imaging reporter; or a cyclic peptide of formula (I):

wherein:

$R^1$ is aspartic acid (D), $R^2$ is NODAGA-glycine (G)-glutamine(Q), $R^3$ is leucine (L), $R^4$ is 2-naphthylalanine (2-Nal), $R^5$ is glycine (G), and $R^6$ is threonine (T), and wherein the cyclic polypeptide comprises an imaging reporter; or a cyclic polypeptide of formula (I):

wherein:

$R^1$ is arginine (R), $R^2$ is NODAGA-glycine (G)-glutamine(Q), $R^3$ is phenylalanine (F), $R^4$ is tyrosine (Y), $R^5$ is glycine (G), and $R^6$ is threonine (T), and wherein the cyclic polypeptide comprises an imaging reporter; or a cyclic polypeptide of formula (I):

wherein:

$R^1$ is leucine (L), $R^2$ is NODAGA-glycine (G)-glutamine(Q), $R^3$ is leucine (L), $R^4$ is tyrosine (Y), $R^5$ is glycine (G), and $R^6$ is tyrosine (Y), and wherein the cyclic polypeptide comprises an imaging reporter; or a cyclic polypeptide of formula (I):

wherein:

$R^1$ is glutamic acid (E), $R^2$ is NODAGA-glycine (G)-glutamine(Q), $R^3$ is leucine (L), $R^4$ is tyrosine (Y), $R^5$ is 4,4-biphenylalanine (BIP), and $R^6$ is threonine (T), and wherein the cyclic polypeptide comprises an imaging reporter.

2. The cyclic polypeptide of claim 1, wherein the imaging reporter is $^{68}$Ga or $^{64}$Cu.

3. A compound having the following structure:

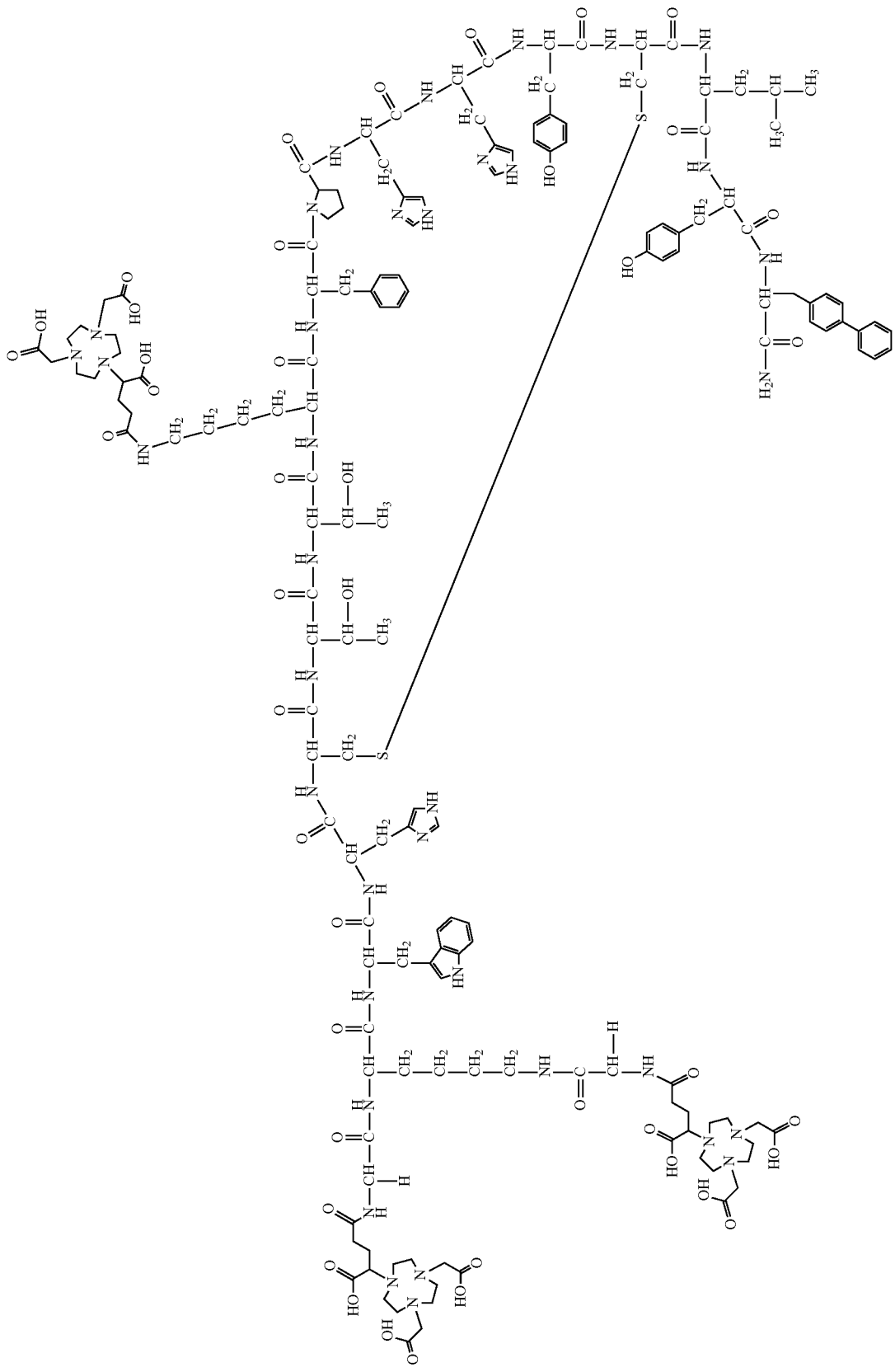

or pharmaceutically acceptable salt thereof.

4. The compound of claim 3, wherein said compound is complexed to one or more positron emitting metal ion isotopes or said compound is complexed to one or more gamma-ray emitting metal ion isotopes.

5. The cyclic polypeptide of claim 1, wherein the cyclic polypeptide is a cyclic polypeptide of formula (I):

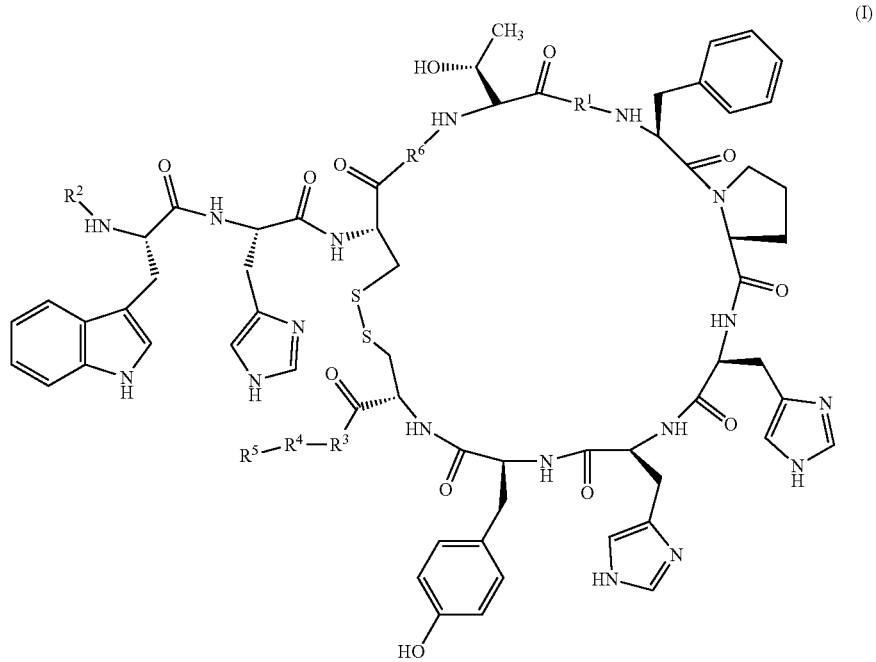

wherein $R^1$ is selected from the group consisting of lysine (K), tyrosine (Y), glutamic acid (E), aspartic acid (D), arginine (R) and leucine (L);

wherein $R^2$ is selected from the group consisting of -glycine (G)-tryptophan (W) and -glycine (G)-lysine (K)[glycine (G)];

wherein $R^3$ is selected from the group consisting of leucine (L) and phenylalanine (F);

wherein $R^4$ is selected from the group consisting of tyrosine (Y) and 2-Nal (2-naphthylalanine);

wherein $R^5$ is selected from the group consisting of glycine (G) and BIP (L-4,4'-biphenylalanine);

wherein $R^6$ is selected from the group consisting of threonine (T) and tyrosine (Y); and wherein the cyclic polypeptide further comprises a metal chelating group capable of binding an imaging reporter, the metal chelating group being covalently linked directly to a cyclic body or a branch of the cyclic polypeptide, or the metal chelating group being linked to the body or a branch of the cyclic polypeptide via a linker.

6. The cyclic polypeptide of claim 5, wherein the imaging reporter is a positron emitter or a photon emitter.

7. The cyclic polypeptide of claim 5, wherein the metal chelating group includes at least one group selected from the group consisting of methylene phosponic acid groups, methylene phospinic acid groups, methylene carbohydroxamine acid groups, carboxyethylidene groups, and carboxymethylene groups.

8. A method for in vivo imaging of a subject, the method comprising:

(a) administering to the subject the cyclic polypeptide of claim 1;

(b) allowing the cyclic polypeptide to accumulate at a tissue site to be imaged; and (c) imaging tissues with a non-invasive imaging technique.

9. A method of imaging a subject by emission tomography, the method comprising:

(a) administering the cyclic polypeptide of claim 1 to the subject, wherein the cyclic polypeptide includes an imaging reporter that emits gamma rays;

(b) detecting gamma rays emitted from the subject using a plurality of detectors; and (c) reconstructing from the detected gamma rays a series of medical images of a region of interest of the subject.

10. An imaging method comprising acquiring an image of a human patient to whom a detectable amount of the cyclic polypeptide of claim 1 has been administered.

11. A method for diagnosing a fibrotic disease in a subject, the method comprising:

(a) administering to the subject the cyclic polypeptide of claim 1;

(b) allowing the cyclic polypeptide to accumulate at a tissue site to be imaged; and (c) imaging tissues with a non-invasive imaging technique.

12. A method for staging a fibrotic disease in a subject, the method comprising:

(a) administering to the subject the cyclic polypeptide of claim 1;

(b) allowing the cyclic polypeptide to accumulate at a tissue site to be imaged;

(c) imaging tissues with a non-invasive imaging technique; and (d) comparing an amount of an imaging signal to a threshold.

13. A method for monitoring treatment of a fibrotic disease in a subject, the method comprising:
(a) administering to the subject the cyclic polypeptide of claim 1;
(b) allowing the cyclic polypeptide to accumulate at a tissue site to be imaged;
(c) imaging tissues with a non-invasive imaging technique to create a first image;
(d) repeating steps (a) and (b);
(e) imaging tissues with the non-invasive imaging technique to create a second image; and
(f) comparing the first image and the second image;
wherein the subject has received treatment for the fibrotic disease between steps (c) and (d).

14. A method of imaging a subject by emission tomography, the method comprising:
(a) administering the cyclic polypeptide of claim 3 to the subject, wherein the cyclic polypeptide includes an imaging reporter that emits gamma rays;
(b) detecting gamma rays emitted from the subject using a plurality of detectors; and
(c) reconstructing from the detected gamma rays a series of medical images of a region of interest of the subject.

15. An imaging method comprising acquiring an image of a human patient to whom a detectable amount of the cyclic polypeptide of claim 3 has been administered.

16. A method for diagnosing a fibrotic disease in a subject, the method comprising:
(a) administering to the subject the cyclic polypeptide of claim 3;
(b) allowing the cyclic polypeptide to accumulate at a tissue site to be imaged; and
(c) imaging tissues with a non-invasive imaging technique.

17. A method for staging a fibrotic disease in a subject, the method comprising:
(a) administering to the subject the cyclic polypeptide of claim 3;
(b) allowing the cyclic polypeptide to accumulate at a tissue site to be imaged;
(c) imaging tissues with a non-invasive imaging technique; and
(d) comparing an amount of an imaging signal to a threshold.

18. A method for monitoring treatment of a fibrotic disease in a subject, the method comprising:
(a) administering to the subject the cyclic polypeptide of claim 3;
(b) allowing the cyclic polypeptide to accumulate at a tissue site to be imaged;
(c) imaging tissues with a non-invasive imaging technique to create a first image;
(d) repeating steps (a) and (b);
(e) imaging tissues with the non-invasive imaging technique to create a second image; and
(f) comparing the first image and the second image;
wherein the subject has received treatment for the fibrotic disease between steps (c) and (d).

19. The method of claim 8, wherein the cyclic polypeptide is allowed to accumulate at the tissue site to be imaged for about 30 minutes to about 8 hours.

20. The method of claim 11, wherein the cyclic polypeptide is allowed to accumulate at the tissue site to be imaged for about 30 minutes to about 8 hours.

21. The method of claim 12, wherein the cyclic polypeptide is allowed to accumulate at the tissue site to be imaged for about 30 minutes to about 8 hours.

22. The method of claim 13, wherein the cyclic polypeptide is allowed to accumulate at the tissue site to be imaged for about 30 minutes to about 8 hours.

23. The method of claim 16, wherein the cyclic polypeptide is allowed to accumulate at the tissue site to be imaged for about 30 minutes to about 8 hours.

24. The method of claim 17, wherein the cyclic polypeptide is allowed to accumulate at the tissue site to be imaged for about 30 minutes to about 8 hours.

25. The method of claim 18, wherein the cyclic polypeptide is allowed to accumulate at the tissue site to be imaged for about 30 minutes to about 8 hours.

26. The cyclic polypeptide of claim 1, wherein:
$R^1$ is lysine (K)-NODAGA;
$R^2$ is NODAGA-glycine (G)-lysine (K)[glycine (G)-NODAGA];
$R^3$ is leucine (L);
$R^4$ is tyrosine (Y);
$R^5$ is 4,4-biphenylalanine (BIP); and
$R^6$ is threonine (T); and
wherein the cyclic polypeptide comprises an imaging reporter.

27. The cyclic polypeptide of claim 1, wherein:
$R^1$ is tyrosine (Y);
$R^2$ is NODAGA-glycine (G)-glutamine(Q);
$R^3$ is leucine (L);
$R^4$ is tyrosine (Y);
$R^5$ is glycine (G);
$R^6$ is threonine (T); and
wherein the cyclic polypeptide comprises an imaging reporter.

28. The cyclic polypeptide of claim 1, wherein:
$R^1$ is aspartic acid (D);
$R^2$ is NODAGA-glycine (G)-glutamine(Q);
$R^3$ is leucine (L);
$R^4$ is 2-naphthylalanine (2-Nal);
$R^5$ is glycine (G); and
$R^6$ is threonine (T); and
wherein the cyclic polypeptide comprises an imaging reporter.

29. The cyclic polypeptide of claim 1, wherein:
$R^1$ is arginine (R);
$R^2$ is NODAGA-glycine (G)-glutamine(Q);
$R^3$ is phenylalanine (F);
$R^4$ is tyrosine (Y);
$R^5$ is glycine (G); and
$R^6$ is threonine (T); and
wherein the cyclic polypeptide comprises an imaging reporter.

30. The cyclic polypeptide of claim 1, wherein:
$R^1$ is leucine (L);
$R^2$ is NODAGA-glycine (G)-glutamine(Q);
$R^3$ is leucine (L);
$R^4$ is tyrosine (Y);
$R^5$ is glycine (G); and
$R^6$ is tyrosine (Y); and
wherein the cyclic polypeptide comprises an imaging reporter.

31. The cyclic polypeptide of claim 1, wherein:
$R^1$ is glutamic acid (E);
$R^2$ is NODAGA-glycine (G)-glutamine(Q);
$R^3$ is leucine (L);
$R^4$ is tyrosine (Y);
$R^5$ is 4,4-biphenylalanine (BIP); and
$R^6$ is threonine (T); and
wherein the cyclic polypeptide comprises an imaging reporter.

* * * * *

UNITED STATES PATENT AND TRADEMARK OFFICE
CERTIFICATE OF CORRECTION

PATENT NO. : 10,471,162 B2
APPLICATION NO. : 15/320112
DATED : November 12, 2019
INVENTOR(S) : Desogere et al.

Page 1 of 1

It is certified that error appears in the above-identified patent and that said Letters Patent is hereby corrected as shown below:

In the Claims

In Column 63, Line 62, Claim 7, delete "phosponic" and insert -- phosphonic --,

In Column 63, Line 63, Claim 7, delete "phospinic" and insert -- phosphinic --.

Signed and Sealed this
Fifth Day of May, 2020

Andrei Iancu
*Director of the United States Patent and Trademark Office*